United States Patent
Williams et al.

(10) Patent No.: US 9,062,076 B2
(45) Date of Patent: Jun. 23, 2015

(54) FUSED RING ANALOGUES OF ANTI-FIBROTIC AGENTS

(75) Inventors: Spencer John Williams, Coburg (AU);
Steven Zammit, Templestowe (AU);
Darren James Kelly, Wonga Park (AU)

(73) Assignee: Fibrotech Therapeutics PTY LTD, Wonga Park (AU)

( * ) Notice: Subject to any disclaimer, the term of this patent is extended or adjusted under 35 U.S.C. 154(b) by 46 days.

(21) Appl. No.: 13/503,160

(22) PCT Filed: Oct. 21, 2010

(86) PCT No.: PCT/AU2010/001398
§ 371 (c)(1),
(2), (4) Date: Jul. 9, 2012

(87) PCT Pub. No.: WO2011/047432
PCT Pub. Date: Apr. 28, 2011

(65) Prior Publication Data
US 2012/0270863 A1    Oct. 25, 2012
US 2013/0338151 A9    Dec. 19, 2013

Related U.S. Application Data

(60) Provisional application No. 61/253,889, filed on Oct. 22, 2009.

(51) Int. Cl.
| C07D 487/04 | (2006.01) |
| --- | --- |
| C07D 513/04 | (2006.01) |
| C07C 235/40 | (2006.01) |
| C07C 235/56 | (2006.01) |
| C07D 235/12 | (2006.01) |
| C07D 239/91 | (2006.01) |
| C07D 241/44 | (2006.01) |
| C07D 263/56 | (2006.01) |
| C07D 265/22 | (2006.01) |
| C07D 277/64 | (2006.01) |
| C07D 471/04 | (2006.01) |
| C07D 495/04 | (2006.01) |
| C07D 498/04 | (2006.01) |

(52) U.S. Cl.
CPC ............ *C07D 513/04* (2013.01); *C07C 235/40* (2013.01); *C07C 235/56* (2013.01); *C07D 235/12* (2013.01); *C07D 239/91* (2013.01); *C07D 241/44* (2013.01); *C07D 263/56* (2013.01); *C07D 265/22* (2013.01); *C07D 277/64* (2013.01); *C07D 471/04* (2013.01); *C07D 495/04* (2013.01); *C07D 498/04* (2013.01)

(58) Field of Classification Search
CPC .. C07D 487/00; C07D 487/04; C07D 498/00; C07D 498/04; C07D 513/00; C07D 513/04; C07D 515/00; C07D 515/04
See application file for complete search history.

(56) References Cited

U.S. PATENT DOCUMENTS

| 4,769,384 A | 9/1988 | Kise et al. |
| --- | --- | --- |
| 5,026,705 A | 6/1991 | Prucher et al. |
| 5,622,977 A | 4/1997 | Warrellow et al. |
| 2009/0012031 A1 | 1/2009 | Chinnaiyan et al. |

FOREIGN PATENT DOCUMENTS

| CN | 101423503 | 5/2009 |
| --- | --- | --- |
| CN | 101423503 A | 5/2009 |
| EP | 0193013 A2 | 9/1986 |
| EP | 0937722 A1 | 8/1999 |
| EP | 1460067 A1 | 9/2004 |
| EP | 1864972 A1 | 12/2007 |
| JP | 52083428 A | 7/1977 |
| JP | 08-113567 | 5/1996 |
| JP | 8113567 A | 5/1996 |
| JP | 08-337523 | 12/1996 |
| WO | WO 96/11917 | 4/1996 |
| WO | WO 96/39391 | 12/1996 |
| WO | WO 96/39391 A1 | 12/1996 |
| WO | WO 98/11438 A1 | 3/1998 |
| WO | WO 01/74810 A2 | 10/2001 |
| WO | WO 2004/096757 A1 | 11/2004 |
| WO | WO 2006/094235 A1 | 9/2006 |
| WO | WO 2008/003141 A1 | 1/2008 |
| WO | WO 2009/079011 A1 | 6/2009 |
| WO | WO 2010/103130 A2 | 9/2010 |

OTHER PUBLICATIONS

Database Registry [Online]; Chemical Abstracts Service, Columbus, Ohio, CAS Registry File RN 925402-95-5, STN Entry Date: Mar. 7, 2007.
Database Registry [Online]; Chemical Abstracts Service, Columbus, Ohio, CAS Registry File RN 81381-70-6, STN Entry Date: Nov. 16, 1984.
Database Registry [Online]; Chemical Abstracts Service, Columbus, Ohio, CAS Registry File RN 865272-13-5, STN Entry Date: Oct. 14, 2005.
Database Registry [Online]; Chemical Abstracts Service, Columbus, Ohio, CAS Registry File RN 340996-04-5, STN Entry Date: Jun. 14, 2001.
Database Registry [Online]; Chemical Abstracts Service, Columbus, Ohio, CAS Registry File RN 1025584-02-4, STN Entry Date: Jun. 5, 2008.
Database Registry [Online]; Chemical Abstracts Service, Columbus, Ohio, CAS Registry File RN 1004255-12-2, STN Entry Date: Feb. 18, 2008.
Database Registry [Online]; Chemical Abstracts Service, Columbus, Ohio, CAS Registry File RN 577770-02-6, STN Entry Date: Sep. 2, 2003.

(Continued)

*Primary Examiner* — Wu-Cheng Winston Shen
*Assistant Examiner* — Christopher R Stone
(74) *Attorney, Agent, or Firm* — Wolf, Greenfield & Sacks, P.C.; C. Hunter Baker; Renée C. Fuller

(57) ABSTRACT

The present invention relates to arylcarbonyl and heteroarylcarbonyl anthranilate compounds that may be useful as anti-fibrotic agents. The present invention also relates to methods for their preparation, pharmaceutical compositions containing these compounds and uses of these compounds in the treatment disorders.

8 Claims, 6 Drawing Sheets

(56) References Cited

OTHER PUBLICATIONS

Database Registry [Online]; Chemical Abstracts Service, Columbus, Ohio, CAS Registry File RN 881944-33-8, STN Entry Date: Apr. 26, 2006.
Database Registry [Online]; Chemical Abstracts Service, Columbus, Ohio, CAS Registry File RN 1013293-13-4, STN Entry Date: Apr. 10, 2008.
Database Registry [Online]; Chemical Abstracts Service, Columbus, Ohio, CAS Registry File RN 457607-17-9, STN Entry Date: Oct. 1, 2002.
Database Registry [Online]; Chemical Abstracts Service, Columbus, Ohio, CAS Registry File RN 848904-62-1, STN Entry Date: Apr. 21, 2005.
Extended European Search Report, EP10824314, Mar. 19, 2013.
Lozano et al., "Cytotoxic anionic tribomo platinum (II) complexes containing benzothiazole and benzoxazole donors: synthesis, characterization, and structure-activity correlation," Inorganica Chimica Acta 271, (1998), 137-144.
Messiha et al. "Synthesis of Some Benzoxazin-4-ones, Quinazolin-4-ones and the Related Products," Indian Journal of Chemistry, (1975), 13: 326-328.
First Office Action mailed on Jan. 3, 2014 in Chinese Appl. No. 201080047294.3.
Search Report and Written Opinion; Singapore Application. No. 201202623-3; Aug. 20, 2013.

FUSED RING ANALOGUES OF ANTI-FIBROTIC AGENTS

RELATED APPLICATIONS

This application is a national stage filing under 35 U.S.C. §371 of International Application No. PCT/AU2010/001398, filed Oct. 21, 2010, which was published under PCT Article 21(2) in English, and which claims priority under 35 U.S.C. §119 from U.S. Provisional Application Ser. No. 61/253,889, filed Oct. 22, 2009, the entire contents of both of which are incorporated by reference herein.

FIELD OF THE INVENTION

The present invention relates to compounds that may be useful in the treatment of medical conditions associated with tissue fibrosis. More particularly, the present invention relates to fused ring derivatives of 2-{[(2E)-3-(3,4-dimethoxyphenyl)prop-2-enoyl]amino}benzoic acid, pharmaceutical compositions containing these derivative compounds, and uses of the derivative compounds in the treatment of certain conditions associated with tissue fibrosis.

BACKGROUND OF THE INVENTION

Fibrosis occurs when excess fibrous connective tissue forms or develops in an organ or tissue. Fibrosis can occur as a part of the wound-healing process following tissue damage resulting from physical injury, inflammation, infection, exposure to toxins, and other causes. Examples of conditions associated with tissue fibrosis include dermal scar formation, keloids, liver fibrosis, kidney fibrosis (including diabetic nephropathy), hepatic cirrhosis, pulmonary interstitial fibrosis, glomerulonephritis, heart failure (ischaemic and non-ischaemic), diabetic nephropathy, scleroderma, excessive scar tissue post surgery or device insertion, progressive, kidney disease, hypertension, heart failure due to ischaemic heart disease, valvular heart disease, hypertensive heart disease, and hypertrophic scars.

The elaboration of extracellular matrix also has a role in fibroproliferative tumor progression and metastasis. Accordingly, strategies that reduce the accumulation of extracellular matrix have been advocated as potential therapies for the treatment and prevention of heart failure in both diabetic and nondiabetic states.

At present the pathogenic mechanism of fibrosis is not completely understood. In general, the proliferation and function of fibroblasts are closely controlled in normal conditions. However, in pathological states in which inflammation or tissue injury is serious or sustained, the tissue repair mechanism goes into overdrive and the control mechanism is abrogated. Excessive tissue repair is caused by over-production of connective tissue protein probably due to abnormal proliferation of fibroblasts and extracellular matrix dysbolism. The cytokines causing such a phenomenon include, fibroblast growth factor (FGF family), transforming growth factor (TGF-β), platelet derived growth factor (PDGF), etc.

Anti-inflammatory agents have been used to treat fibrosis with the aim of suppressing chronic inflammation, but such treatments can be unsatisfactory in terms of efficacy and side effects. Numerous studies have been performed to obtain substances that inhibit the production or the activity of the cytokines thought to be involved in fibrosis. Tranilast (n-[3,4-dimethoxycinnamoyl]anthranilic acid) is an anti-fibrotic agent used in Japan for the treatment of fibrotic skin disorders such as keloids and scleroderma. Although the precise mechanisms and mode of action of tranilast are incompletely understood, its ability to inhibit ERK phosphorylation, a major intermediate in the TGF-β signalling pathway, may underlie its antifibrotic effects, with known actions of tranilast including the inhibition of TGF-β-induced extracellular matrix production in a range of cell types. Tranilast has also been shown to attenuate TGF-β-induced collagen synthesis in cardiac fibroblasts, using an experimental model of diabetic cardiac disease, and to reduce inflammation in allergic diseases, such as allergic rhinitis and bronchial asthma, etc. In addition, tranilast has been shown to have anti-proliferative activity.

However, it has recently been shown that genetic factors in certain patients may confer susceptibility to tranilast-induced hyperbilirubinemia. One possibility for how this may arise is the presence of Gilbert's syndrome polymorphisms of the glucuronosyltransferase UGT1A1, which leads to increased susceptibility to tranilast-induced hyperbilirubinemia. Such hyperbilirubinemia may result from the low level of UGT1A1 glucuronosyltransferase present in individuals with this syndrome. Tranilast itself, and its major metabolite N3 (4-desmethyl-tranilast), have been shown to be inhibitors of UGT1A1, potentially leading to aberrant metabolism of bilirubin and its accumulation.

Accordingly, compounds that are based on tranilast have the potential to provide further biologically active compounds that would be expected to have useful, improved pharmaceutical properties with potential anti-fibrotic, anti-inflammatory, and anti-proliferative or anti-neoplastic activity for the treatment or prevention of diseases associated with fibrosis, diseases characterised by inflammation or neoplastic disease (both benign and malignant), and as alternatives/adjuncts to tranilast.

SUMMARY OF THE INVENTION

In one aspect, the present invention provides a compound of Formula (I)

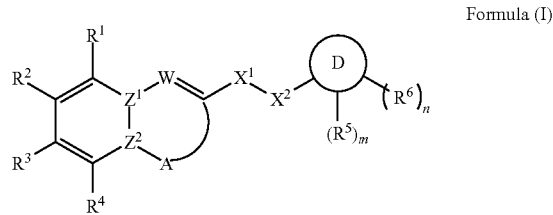

Formula (I)

or a pharmaceutically acceptable salt or prodrug thereof, wherein:

W is selected from the group consisting of: $CR^7$ and N;

A is selected from the group consisting of: $-(CR^8R^9)_p-(Y)_q-(C(O))_r-(CR^{10}R^{11})_s-$ and $-(CR^8R^9)_p-(C(O))_r-(Y)_q-(CR^{10}R^{11})_s-$, wherein Y is selected from the group consisting of: O, S, $NR^{12}$, each p and s are an integer independently selected from the group consisting of 0, 1, and 2, each q and r are an integer independently selected from the group consisting of 0 and 1, and p+q+r+s is an integer selected from the group consisting of 1, 2, and 3;

$Z^1-Z^2$ is selected from the group consisting of N—C= and C=C;

$X^1$ is selected from the group consisting of: C=O, $CF_2$ or $SO_2$, $PO_2$;

$X^2$ is selected from the group consisting of: $NR^{13}$ and $(CH_2)_t$ wherein t is an integer selected from the group consisting of: 0 and 1;

D is selected from the group consisting of: a cycloalkyl, heterocycloalkyl, cycloalkenyl, heterocycloalkenyl, aryl or heteroaryl ring;

$R^1$, $R^4$, $R^5$, $R^6$, $R^7$, $R^8$, $R^9$, $R^{10}$, and $R^{11}$ are each independently selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_8$-$C_{18}$ aryloxy, optionally substituted $C_1$-$C_{18}$ heteroaryloxy, optionally substituted $C_1$-$C_{12}$ alkylamino, $SR^{14}$, $SO_3H$, $SO_2NR^{15}R^{16}$, $SO_2R^{14}$, $SONR^{15}R^{16}$, $SOR^{14}$, $COR^{14}$, COOH, $COOR^{14}$, $CONR^{15}R^{15}R^{16}$, $NR^{15}COR^{14}$, $NR^{15}COOR^{14}$, $NR^{15}SO_2R^{14}$, $NR^{15}CONR^{15}R^{15}R^{16}$, $NR^{15}R^{16}$, and acyl;

$R^2$ and $R^3$, are each independently selected from the group consisting of: H, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_6$-$C_{18}$ heteroaryloxy, optionally substituted $C_1$-$C_{12}$ alkylamino, $SR^{14}$, $SO_3H$, $SO_2NR^{15}R^{16}$, $SO_2R^{14}$, $SONR^{15}R^{16}$, $SOR^{14}$, $COR^{14}$, COOH, $COOR^{14}$, $CONR^{15}R^{16}$, $NR^{15}COR^{14}$, $NR^{15}COOR^{14}$, $NR^{15}SO_2R^{14}$, $NR^{15}CONR^{16}R^{17}$, $NR^{15}R^{16}$, and acyl; or $R^2$ and $R^3$ may be fused to form a 5 or 6 membered cycloalkyl, heterocycloalkyl, aryl or heteroaryl ring each of which may be optionally substituted;

$R^{12}$, $R^{13}$, $R^{15}$, $R^{16}$, and $R^{17}$ are each independently selected from the group consisting of: H, an N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

$R^{14}$ is selected from the group consisting of H, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

m is an integer selected from the group consisting of 0, 1, 2, 3, and 4;

n is an integer selected from the group consisting of 1, 2, 3, 4, and 5; and m+n is an integer selected from the group consisting of 1, 2, 3, 4, and 5.

As with any group of structurally related compounds which possess a particular utility, certain embodiments of variables of the compounds of the Formula (I), may be particularly useful in their end use application.

In some embodiments of the first aspect of the invention, $R^2$ is —$X^3$—$R^{18}$ and $R^3$ is —$X^4$—$R^{19}$, wherein:

$R^{18}$ and $R^{19}$ are the same or different and are selected from the group consisting of: H, halogen, $C_{1\text{-}10}$ alkyl, $C_3$-$C_{10}$ cyclokalkyl, $C_3$-$C_{10}$ cycloalkylmethyl, $C_3$-$C_{10}$ alkene, $C_3$-$C_{10}$ alkyne, aryl, $C_5$-$C_{20}$ alkaryl, fused $C_5$-$C_{20}$ aryl or alkaryl and a hydrocarbon chain containing a heterocyclic or fused ring, any of which may be optionally substituted;

$X^3$ and $X^4$ are the same or different and are selected from the group consisting of: a bond $CR^{20}R^{21}$, O, $NR^{22}$ and S;

$R^{20}$ and $R^{21}$ are the same or different and are selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{14}$, $SO_3H$, $SO_2NR^{15}R^{16}$, $SO_2R^{14}$, $SONR^{15}R^{16}$, $SOR^{14}$, $COR^4$, COOH, $COOR^{14}$, $CONR^{15}R^{16}$, $NR^{15}COR^{14}$, $NR^{15}COOR^{14}$, $NR^{15}SO_2R^{14}$, $NR^{15}CONR^{16}R^{17}$, $NR^{15}R^{16}$, and acyl; and $R^{22}$ is selected from the group consisting of: H, an N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl.

This provides compounds of Formula (Ia):

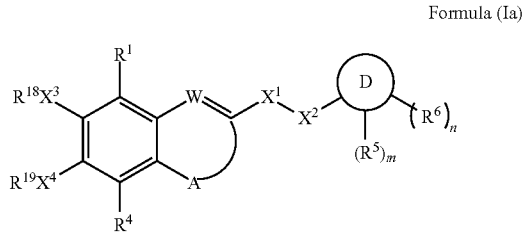

Formula (Ia)

In some embodiments of the first aspect of the invention, $R^{18}$ and $R^{19}$ are fused to form a 5 or 6 membered cycloalkyl, heterocycloalkyl, cycloalkenyl, heterocycloalkenyl, aryl or heteroaryl ring, each of which may be optionally substituted.

In some embodiments of the first aspect of the invention, D is selected from the group consisting of: phenyl, $C_3$-$C_6$ cycloalkyl, $C_2$-$C_5$ heterocycloalkyl, $C_2$-$C_5$ heteroaryl.

In some embodiments of the first aspect of the invention, $R^5$ is selected from the group consisting of: $COOR^{14}$, $COR^{14}$, $CONR^{15}R^{16}$, $NR^{15}R^{16}$, $SO_2R^{14}$ and $SONR^{15}R^{16}$. For example, $R^5$ may be selected from the group consisting of: COOH, $CONH_2$, $CONHCH_3$, CONHOH, $NH_2$, $SO_2CH_3$, $SO_2NH_2$, $SONHCH_3$, and $SON(CH_3)_2$.

In some embodiments of the first aspect of the invention, D is selected from the group consisting of phenyl and $C_2$-$C_5$ heteroaryl and the $R^5$ substituent is ortho to $X^2$. In some other embodiments, D is selected from the group consisting of $C_3$-$C_6$ cycloalkyl and $C_2$-$C_5$ heterocycloalkyl and the $R^5$ substituent is either geminal or vicinal to $X^2$.

In some embodiments of the first aspect of the invention, $R^5$ is selected from the group consisting of: H and halogen.

In some embodiments of the first aspect of the invention, $X^1$ is selected from the group consisting of: C=O and $SO_2$.

In some embodiments of the first aspect of the invention, $X^2$ is $NR^{13}$.

In some embodiments of the first aspect of the invention, $R^{13}$ is selected from the group consisting of: H and optionally substituted $C_1$-$C_{12}$ alkyl.

In some embodiments of the first aspect of the invention, W is $CR^7$.

In some embodiments of the first aspect of the invention, $R^7$ is H.

In some embodiments of the first aspect of the invention, A is selected from the group consisting of: CH, $CH_2CH_2$, CH=CH, O, OC(O), OC(S), $OCH_2$, C(O)O, C(S)O, $SCH_2$, SC(O), SC(S), S, $SO_2CH_2$, $SO_2$, C(O)S, C(O)NH, C(S)S, NH, NH(CO), N, N=CH, and $NHCH_2$.

In some embodiments of the first aspect of the invention, $R^2$ and $R^3$ are each independently selected from the group consisting of: optionally substituted $C_1$-$C_{12}$ alkyloxy and optionally substituted $C_2$-$C_{12}$ alkynyloxy.

In some embodiments of the first aspect of the invention, the optionally substituted $C_1$-$C_{12}$ alkyloxy is $C_1$-$C_{12}$ fluoroalkyloxy.

In some embodiments of the first aspect of the invention, the optionally substituted $C_2$-$C_{12}$ alkynyloxy is $C_2$-$C_{12}$ alkynylalkyloxy.

In some embodiments of the first aspect of the invention, $R^1$ is selected from the group consisting of: H and optionally substituted $C_1$-$C_6$ alkoxy.

In some embodiments of the first aspect of the invention, $R^2$ is selected from the group consisting of: $H_3CO$, $F_2HCF_2CO$, $F_2HCO$, $F_3CO$, and $CHCCH_2O$.

In some embodiments of the first aspect of the invention, $R^3$ is selected from the group consisting of: $H_3CO$, $F_2HCF_2CO$, $F_2HCO$, $F_3CO$, and $CHCCH_2O$.

In some embodiments of the first aspect of the invention, $R^4$ is selected from the group consisting of: H and optionally substituted $C_1$-$C_6$ alkoxy.

In some embodiments of the first aspect of the invention, $R^2$ and $R^3$ together are selected from the group consisting of: $OCF_2CF_2CO$, $OCH_2CH_2O$, $OCF_2O$, and $OCH_2O$.

In some embodiments of the first aspect of the invention, the compound of Formula (I) is selected from the group consisting of:

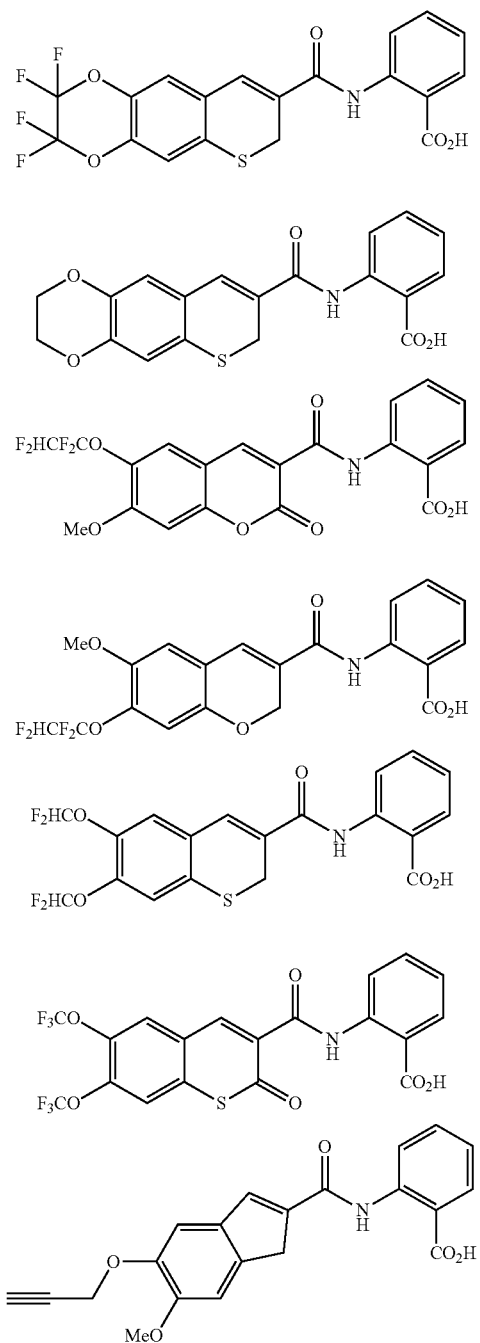

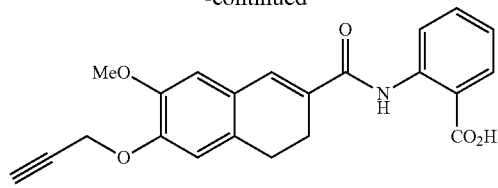
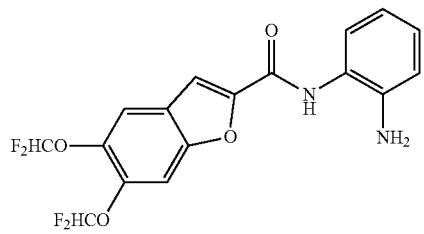
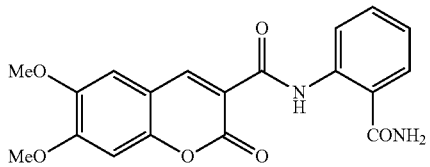
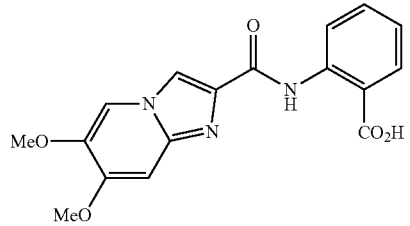
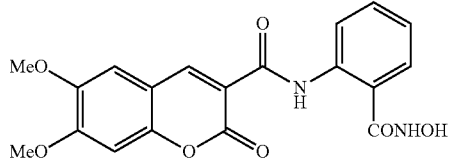
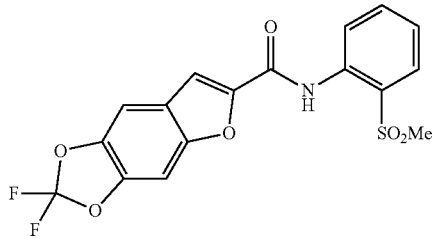
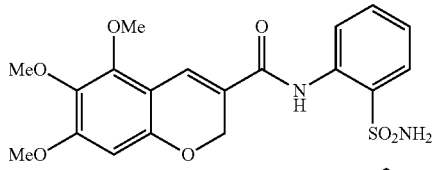
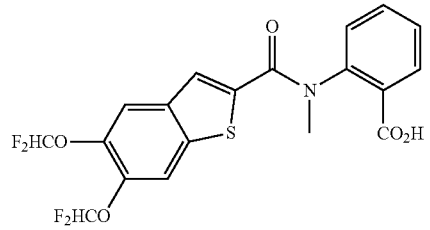
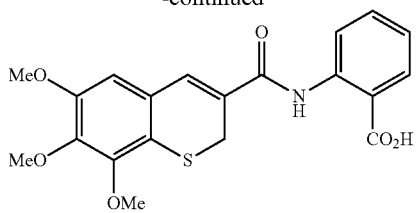
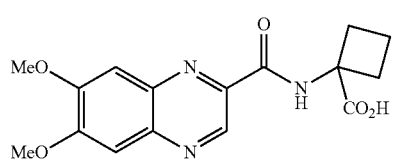
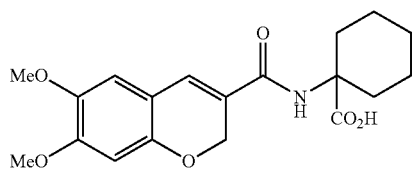
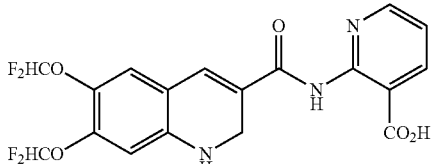
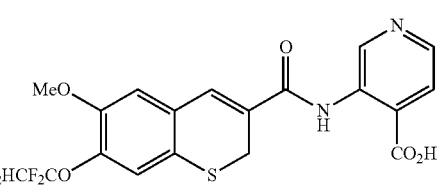
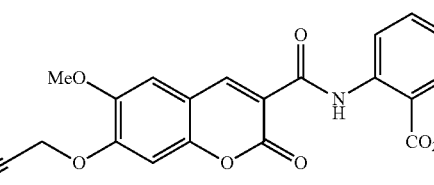
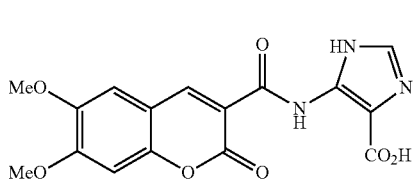
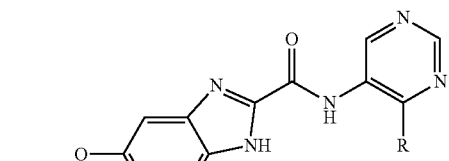
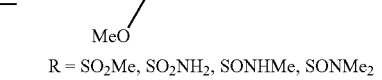
R = SO₂Me, SO₂NH₂, SONHMe, SONMe₂

-continued

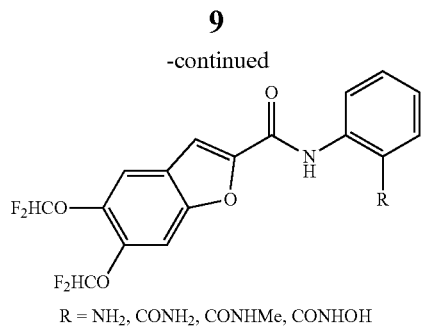

R = NH₂, CONH₂, CONHMe, CONHOH

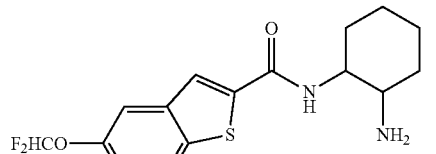

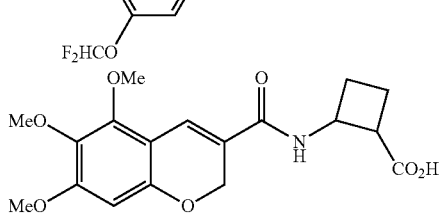

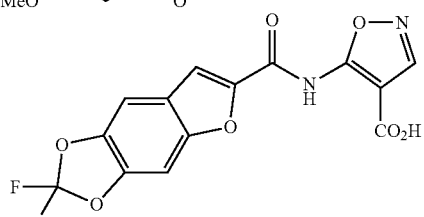

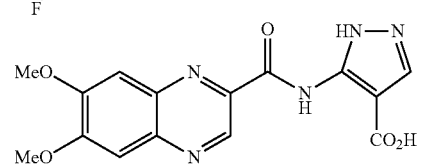

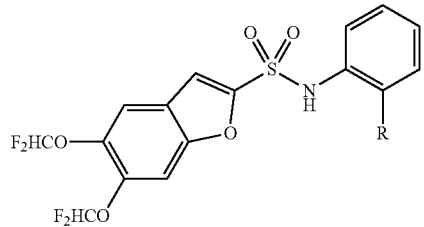

R = SO₂Me, SO₂NH₂, SONHMe, SONMe₂

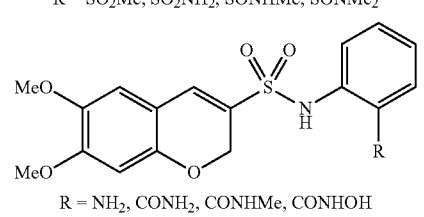

R = NH₂, CONH₂, CONHMe, CONHOH

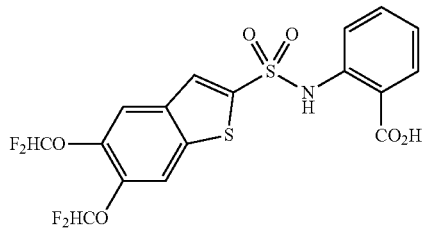

-continued

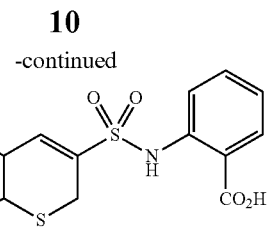

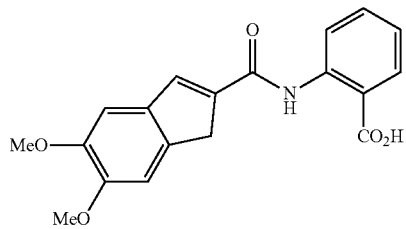

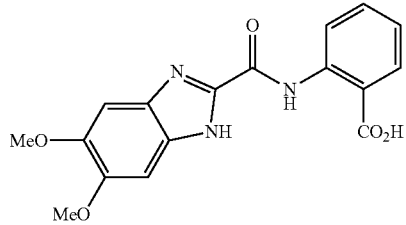

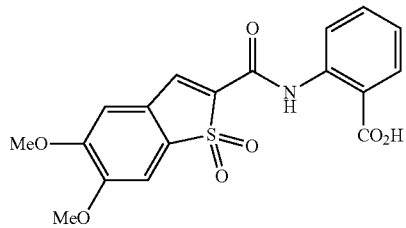

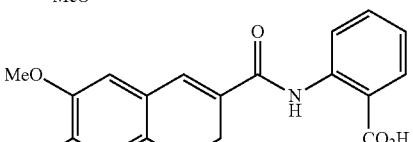

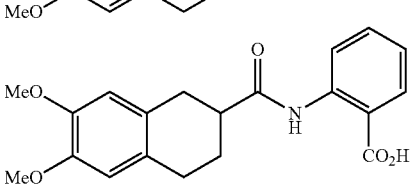

or a pharmaceutically acceptable salt or prodrug thereof.

In a second aspect, the present invention provides a compound of Formula (II)

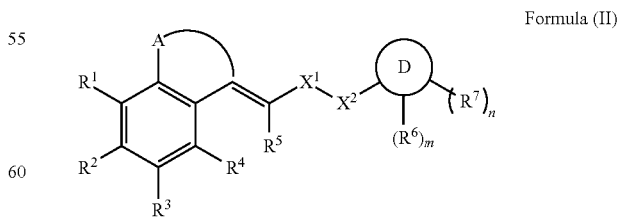

Formula (II)

or a pharmaceutically acceptable salt or prodrug thereof, wherein:

A is selected from the group consisting of: —(CR⁸R⁹)$_p$—(Y)$_q$—(C(O))$_r$—(CR¹⁰R¹¹)$_s$— and —(CR⁸R⁹)$_p$—(C $(O))_r$—$(Y)_q$—$(CR^{10}R^{11})_s$—, wherein Y is selected from the group consisting of: O, S, and $NR^{12}$, each p and s are an integer independently selected from the group consisting of: 0, 1, and 2, each q and r are an integer independently selected from the group consisting of: 0 and 1, and p+q+r+s is an integer selected from the group consisting of: 1, 2, and 3;

$X^1$ is selected from the group consisting of: C=O, $CF_2$, and $SO_2$, $PO_2$;

$X^2$ is selected from the group consisting of: $NR^{13}$ or $(CH_2)_t$, wherein t is an integer selected from the group consisting of: 0 and 1;

D is selected from the group consisting of: a cycloalkyl, heterocycloalkyl, cycloalkenyl, heterocycloalkenyl, aryl or heteroaryl ring;

$R^1$, $R^2$ and $R^3$, are each independently selected from the group consisting of: H, OH, $NO_2$, CN, $NH_2$, optionally substituted. $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{14}$, $SO_3H$, $SO_2NR^{15}R^{16}$, $SO_2R^{14}$, $SONR^{15}R^{16}$, $SOR^{14}$, $COR^{14}$, COOH, $COOR^{14}$, $CONR^{15}R^{16}$, $NR^{15}COR^{14}$, $NR^{15}COOR^{14}$, $NR^{15}SO_2R^{14}$, $NR^{15}CONR^{16}R^{17}$, $NR^{15}R^{16}$, and acyl; or $R^2$ and $R^3$ may be fused to form a 5 or 6 membered cycloalkyl, heterocycloalkyl, aryl or heteroaryl ring each of which may be optionally substituted;

$R^4$, $R^5$, $R^6$, $R^7$, $R^8$, $R^9$, $R^{10}$ and $R^{11}$ are each independently selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{14}$, $SO_3H$, $SO_2NR^{15}R^{16}$, $SO_2R^{14}$, $SONR^{15}R^{16}$, $SOR^{14}$, $COR^{14}$, COOH, $COOR^{14}$, $CONR^{15}R^{16}$, $NR^{15}COR^{14}$, $NR^{15}COOR^4$, $NR^{15}SO_2R^{14}$, $NR^{15}CONR^{16}R^{17}$, $NR^{15}R^{16}$, and acyl;

$R^{12}$, $R^{13}$, $R^{15}$, $R^{16}$, and $R^{17}$ are each independently selected from the group consisting of: H, a N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

$R^{14}$ is selected from the group consisting of H, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally, substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

m is an integer selected from the group consisting of: 0, 1, 2, 3, and 4;

n is an integer selected from the group consisting of: 1, 2, 3, 4, and 5; and m+n is an integer selected from the group consisting of: 1, 2, 3, 4, and 5.

In some embodiments of the second aspect of the invention, $R^1$ is —$X^3$—$R^{18}$ and $R^2$ is —$X^4$—$R^{19}$, wherein:

$R^{18}$ and $R^{19}$ are the same or different and are selected from the group consisting of: H, halogen, $C_{1-10}$ alkyl, $C_3$-$C_{10}$ cyclokalkyl, $C_3$-$C_{10}$ cycloalkylmethyl, $C_3$-$C_{10}$ alkene, $C_3$-$C_{10}$ alkyne, aryl, $C_5$-$C_{20}$ alkaryl, fused $C_5$-$C_{20}$ aryl or alkaryl and a hydrocarbon chain containing a heterocyclic or fused ring, any of which may be optionally substituted;

$X^3$ and $X^4$ are the same or different and are selected from the group consisting of: a bond $CR^{20}R^{21}$, O, $NR^{22}$, and S;

$R^{20}$ and $R^{21}$ are the same or different and are selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{14}$, $SO_3H$, $SO_2NR^{15}R^{16}$, $SO_2R^{14}$, $SONR^{15}R^{16}$, $SOR^4$, $COR^{14}$, COOH, $COOR^{14}$, $CONR^{15}R^{16}$, $NR^{15}COR^{14}$, $NR^{15}COOR^{14}$, $NR^{15}SO_2R^{14}$, $NR^{15}CONR^{16}R^{17}$, $NR^{15}R^{16}$, and acyl; and $R^{22}$ is selected from the group consisting of: H, an N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl.

This provides compounds of Formula (IIa):

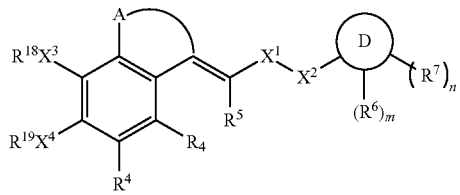

Formula (IIa)

In some embodiments of the second aspect of the invention, $R^2$ is —$X^3$—$R^{18}$ and $R^3$ is —$X^4$—$R^{19}$, wherein:

$R^{18}$ and $R^{19}$ are the same or different and are selected from the group consisting of: H, halogen, $C_{1-10}$ alkyl, $C_3$-$C_{10}$ cyclokalkyl, $C_3$-$C_{10}$ cycloalkylmethyl, $C_3$-$C_{10}$ alkene, $C_3$-$C_{10}$ alkyne, aryl, $C_5$-$C_{20}$ alkaryl, fused $C_5$-$C_{20}$ aryl or alkaryl and a hydrocarbon chain containing a heterocyclic or fused ring, any of which may be optionally substituted;

$X^3$ and $X^4$ are the same or different and are selected from the group consisting of: a bond $CR^{20}R^{21}$, O, $NR^2$, and S;

$R^{20}$ and $R^{21}$ are the same or different and are selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{14}$, $SO_3H$, $SO_2NR^{15}R^{16}$, $SO_2R^{14}$, $SONR^{15}R^{16}$, $SOR^{14}$, $COR^{14}$, COOH, $COOR^{14}$, $CONR^{15}R^{16}$, $NR^{15}COR^{14}$, $NR^{15}COOR^{14}$, $NR^{15}SO_2R^{14}$, $NR^{15}CONR^{16}R^{17}$, $NR^{15}R^{16}$, and acyl; and $R^{22}$ is selected from the group consisting of: H, an N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl.

This provides compounds of Formula (IIb):

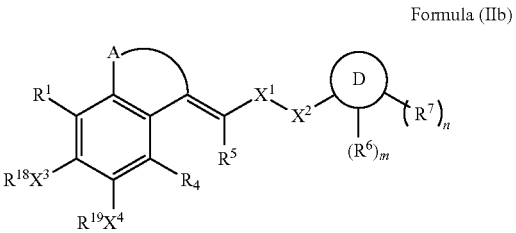

Formula (IIb)

In some embodiments of the second aspect of the invention, $R^{18}$ and $R^{19}$ are fused to form a 5 or 6 membered cycloalkyl, heterocycloalkyl, aryl or heteroaryl ring, each of which may be optionally substituted.

In some embodiments of the second aspect of the invention, D is selected from the group consisting of: phenyl, $C_3$-$C_6$ cycloalkyl, $C_2$-$C_5$ heteroaryl.

In some embodiments of the second aspect of the invention, $R^5$ is selected from the group consisting of: H, CN, $NO_2$, and $C_1$-$C_6$alkyl.

In some embodiments of the second aspect of the invention, $R^6$ is selected from the group consisting of: $COOR^{14}$, $COR^{14}$, $CONR^{15}R^{16}$, $NR^{15}R^{16}$, and $SO_2R^{14}$ and $SONR^{15}R^{16}$.

In some embodiments of the second aspect of the invention, $R^6$ is selected from the group consisting of: COOH, $CONH_2$, CONHOH, $CONHCH_3$, $NH_2$, $SO_2CH_3$, $SO_2NH_2$, $SONHCH_3$, and $SON(CH_3)_2$.

In some embodiments of the second aspect of the invention, D is selected from the group consisting of phenyl and $C_2$-$C_5$ heteroaryl and the $R^6$ substituent is ortho to $X^2$.

In some embodiments of the second aspect of the invention, D is selected from the group consisting of $C_3$-$C_6$ cycloalkyl and $C_2$-$C_5$ heterocycloalkyl and the $R^6$ substituent is either geminal or vicinal to $X^2$.

In some embodiments of the second aspect of the invention, $R^7$ is selected from the group consisting of H and halogen.

In some embodiments of the second aspect of the invention, $X^1$ is selected from the group consisting of: C=O and $SO_2$.

In some embodiments of the second aspect of the invention, $X^2$ is $NR^{13}$.

In some embodiments of the second aspect of the invention, $R^{13}$ is selected from the group consisting of: H and optionally substituted $C_1$-$C_{12}$ alkyl.

In some embodiments of the second aspect of the invention, A is selected from the group consisting of: $CH_2CH_2$, CH=CH, C(O)O, C(O)S, $C(O)NR^{12}$, OC(O), SC(O), $NR^{12}C(O)$, $CH_2CH_2CH_2$, CH=$CHCH_2$, $CH_2CH$=CH, $OCH_2CH_2$, $SCH_2CH_2$, $NR^{12}CH_2CH_2$, $CH_2CH_2O$, $CH_2CH_2S$, $CH_2CH_2NR^{12}$, $C(O)OCH_2$, $C(O)SCH_2$, $C(O)NR^{12}CH_2$, $CH_2OC(O)$, $CH_2SC(O)$, and $CH_2NR^{12}C(O)$.

In some embodiments of the second aspect of the invention, $R^1$, $R^2$ and $R^3$ are each independently selected from the group consisting of: optionally substituted $C_1$-$C_{12}$ alkyloxy and optionally substituted $C_2$-$C_{12}$ alkynyloxy.

In some embodiments of the second aspect of the invention, the optionally substituted $C_1$-$C_{12}$ alkyloxy is $C_1$-$C_{12}$ fluoroalkyloxy.

In some embodiments of the second aspect of the invention, the optionally substituted $C_2$-$C_{12}$ alkynyloxy is $C_2$-$C_{12}$ alkynylalkyloxy.

In some embodiments of the second aspect of the invention, $R^1$ is selected from the group consisting of: $H_3CO$, $F_2HCF_2CO$, $F_2HCO$, $F_3CO$, and $CHCCH_2O$.

In some embodiments of the second aspect of the invention, $R^2$ is selected from the group consisting of: $H_3CO$, $F_2HCF_2CO$, $F_2HCO$, $F_3CO$, and $CHCCH_2O$.

In some embodiments of the second aspect of the invention, $R^3$ is selected from the group consisting of: $H_3CO$, $F_2HCF_2CO$, $F_2HCO$, $F_3CO$, and $CHCCH_2O$.

In some embodiments of the second aspect of the invention, $R^1$ and $R^2$ together are selected from the group consisting of: $OCF_2CF_2CO$, $OCH_2CH_2O$, $OCF_2O$, and $OCH_2O$.

In some embodiments of the second aspect of the invention, $R^2$ and $R^3$ together are selected from the group consisting of: $OCF_2CF_2CO$, $OCH_2CH_2O$, $OCF_2O$, and $OCH_2O$.

In some embodiments of the second aspect of the invention, the compound of Formula (II) is selected from the group consisting of:

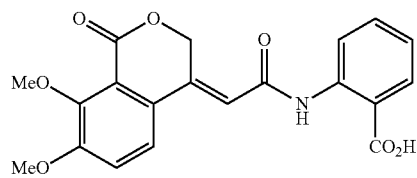

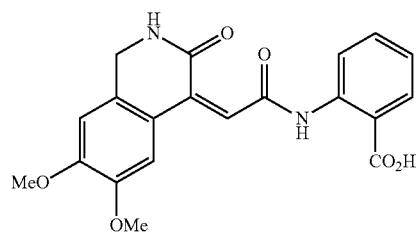

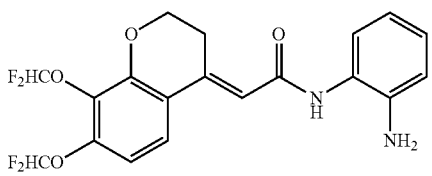

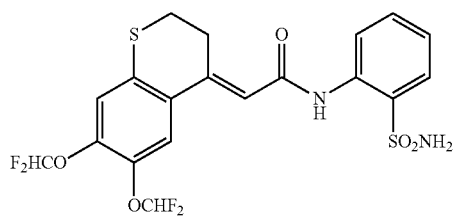

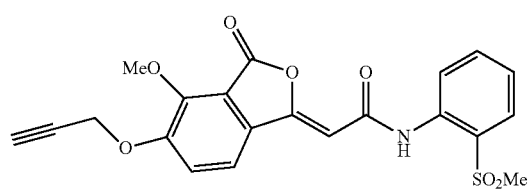

-continued

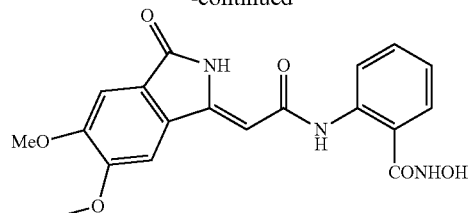

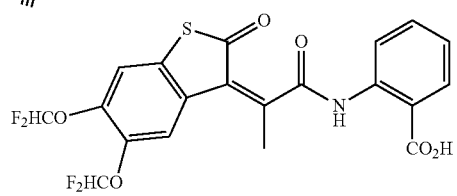

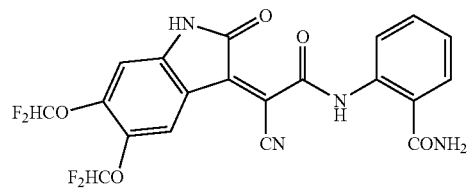

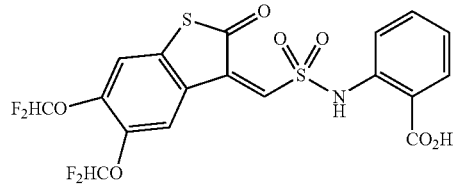

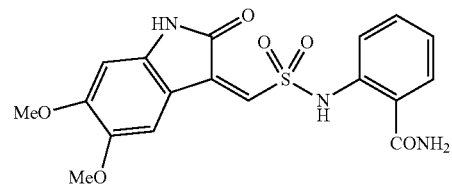

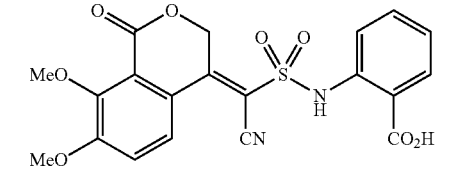

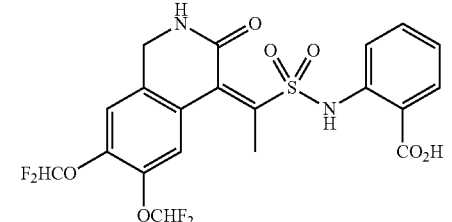

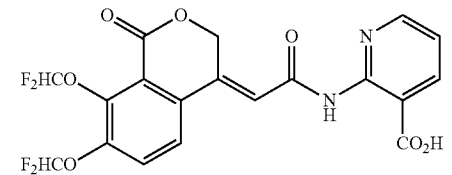

-continued

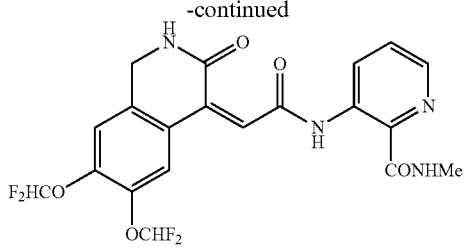

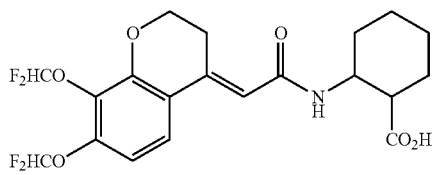

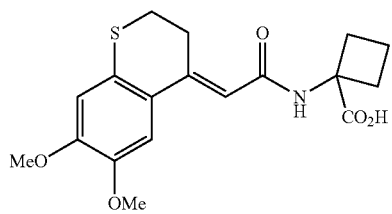

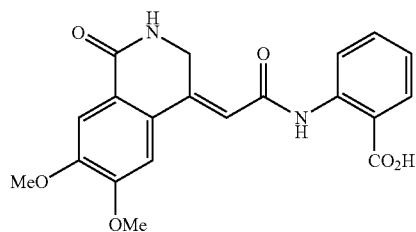 [SMILES: COc1cc2c(cc1OC)/C(=C/C(=O)Nc1ccccc1C(=O)O)CNC2=O]

or a pharmaceutically acceptable salt or prodrug thereof.

In a third aspect, the present invention provides a compound of Formula (III)

Formula (III)

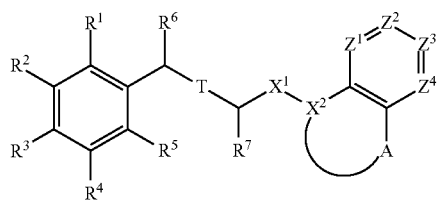

or a pharmaceutically acceptable salt or prodrug thereof, wherein:

A is selected from the group consisting of: —(CR$^9$R$^{10}$)$_p$—(Y)$_q$—(C(O))$_r$(CR$^{11}$R$^{12}$)$_s$— and —(CR$^9$R$^{10}$)$_p$—(C(O))$_r$—(Y)$_q$—(CR$^{11}$R$^{12}$)$_s$—, wherein Y is selected from the group consisting of: O, S, NR$^{13}$, each p and s are an integer independently selected from the group consisting of: 0, 1, and 2, each q and r are an integer independently selected from the group consisting of: 0 and 1, and p+q+r+s is an integer selected from the group consisting of: 1, 2, and 3;

T is selected from the group consisting of: a single bond, a double bond, a triple bond and

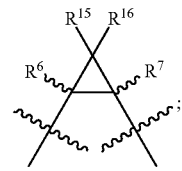

$X^1$ is selected from the group consisting of: C=O, CF$_2$ or SO$_2$, PO$_2$;

$X^2$ is selected from the group consisting of: CR$^{17}$ and N;

$Z^1$, $Z^2$, $Z^3$, and $Z^4$ are each independently selected from the group consisting of CR$^8$ and N;

R$^1$, R$^4$, R$^5$, R$^8$, R$^9$, R$^{10}$, R$^{11}$, R$^{12}$, R$^{15}$, R$^{16}$ and R$^{17}$ are each independently selected from the group consisting of: H, halogen, OH, NO$_2$, CN, NH$_2$, optionally substituted C$_1$-C$_{12}$ alkyl, optionally substituted C$_2$-C$_{12}$ alkenyl, optionally substituted C$_2$-C$_{12}$ alkynyl, optionally substituted C$_1$-C$_{10}$ heteroalkyl, optionally substituted C$_3$-C$_{12}$ cycloalkyl, optionally substituted C$_3$-C$_{12}$ cycloalkenyl, optionally substituted C$_2$-C$_{12}$ heterocycloalkyl, optionally substituted C$_2$-C$_{12}$ heterocycloalkenyl, optionally substituted C$_6$-C$_{18}$ aryl, optionally substituted C$_1$-C$_{18}$ heteroaryl, optionally substituted C$_1$-C$_{12}$ alkyloxy, optionally substituted C$_2$-C$_{12}$ alkenyloxy, optionally substituted C$_2$-C$_{12}$ alkynyloxy, optionally substituted C$_1$-C$_{10}$ heteroalkyloxy, optionally substituted C$_3$-C$_{12}$ cycloalkyloxy, optionally substituted C$_3$-C$_{12}$ cycloalkenyloxy, optionally substituted C$_1$-C$_{12}$ heterocycloalkyloxy, optionally substituted C$_1$-C$_{12}$ heterocycloalkenyloxy, optionally substituted C$_6$-C$_{18}$ aryloxy, optionally substituted C$_1$-C$_{18}$ heteroaryloxy, optionally substituted C$_1$-C$_{12}$ alkylamino, SR$^{11}$, SO$_3$H, SO$_2$NR$^{19}$R$^{20}$, SO$_2$R$^{18}$, SONR$^{19}$R$^{20}$, SOR$^{18}$, COR$^{11}$, COOH, COOR$^{18}$, CONR$^{19}$R$^{20}$, NR$^{19}$COR$^{20}$, NR$^{19}$COOR$^{18}$, NR$^{19}$SO$_2$R$^{18}$, NR$^{19}$CONR$^{20}$R$^{21}$, NR$^{19}$R$^{20}$, and acyl;

R$^2$ and R$^3$, are each independently selected from the group consisting of: H, OH, NO$_2$, CN, NH$_2$, optionally substituted C$_1$-C$_{12}$ alkyl, optionally substituted C$_2$-C$_{12}$ alkenyl, optionally substituted C$_2$-C$_{12}$ alkynyl, optionally substituted C$_1$-C$_{10}$ heteroalkyl, optionally substituted C$_3$-C$_{12}$ cycloalkyl, optionally substituted C$_3$-C$_{12}$ cycloalkenyl, optionally substituted C$_2$-C$_{12}$ heterocycloalkyl, optionally substituted C$_2$-C$_{12}$ heterocycloalkenyl, optionally substituted C$_6$-C$_{18}$ aryl, optionally substituted C$_1$-C$_{18}$ heteroaryl, optionally substituted C$_1$-C$_{12}$ alkyloxy, optionally substituted C$_2$-C$_{12}$ alkenyloxy, optionally substituted C$_2$-C$_{12}$ alkynyloxy, optionally substituted C$_1$-C$_{10}$ heteroalkyloxy, optionally substituted C$_3$-C$_{12}$ cycloalkyloxy, optionally substituted C$_3$-C$_{12}$ cycloalkenyloxy, optionally substituted C$_1$-C$_{12}$ heterocycloalkyloxy, optionally substituted C$_1$-C$_{12}$ heterocycloalkenyloxy, optionally substituted C$_6$-C$_{18}$ aryloxy, optionally substituted C$_1$-C$_{18}$ heteroaryloxy, optionally substituted C$_1$-C$_{12}$ alkylamino, SR$^{18}$, SO$_3$H, SO$_2$NR$^{19}$R$^{20}$, SO$_2$R$^{18}$, SONR$^{11}$R$^{20}$, SOR$^{18}$, COR$^{18}$, COOH, COOR$^{18}$, CONR$^{19}$R$^{20}$, NR$^{19}$COR$^{18}$, NR$^{19}$COOR$^{18}$, NR$^{19}$SO$_2$R$^{18}$, NR$^{19}$CONR$^{20}$R$^{21}$, NR$^{19}$R$^{20}$, and acyl; or R$^2$ and R$^3$ may be fused to form a 5 or 6 membered cycloalkyl, heterocycloalkyl, aryl or heteroaryl ring, each of which may be optionally substituted;

R$^6$ and R$^7$ are present when T is a single bond, a double bond or

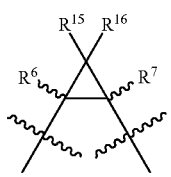

but not when T is a triple bond, each $R^6$ and $R^7$ being independently selected from the group consisting of: H, $NO_2$, CN, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{18}$, $SO_3H$, $SO_2NR^{19}R^{20}$, $SO_2R^{18}$, $SONR^{19}R^{20}$, $SOR^{18}$, $COR^{18}$, COOH, $COOR^{18}$, $CONR^{19}R^{20}$, $NR^{19}COR^{18}$, $NR^{19}COOR^{18}$, $NR^{11}SO_2R^8$, $NR^{19}CONR^{20}R^{21}$, $NR^{19}R^{20}$, and acyl;

$R^{13}$, $R^{19}$, $R^2$ and $R^{21}$ are each independently selected from the group consisting of: H; a N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

$R^{18}$ is selected from the group consisting of H, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl; and n is an integer selected from the group consisting of: 0, 1, 2, 3, and 4.

In some embodiments of the third aspect of the invention, $R^2$ is —$X^3$—$R^{22}$ and $R^3$ is —$X^4$—$R^{23}$, wherein:

$R^{22}$ and $R^{23}$ are the same or different and are selected from the group consisting of: H, halogen, $C_{1-10}$ alkyl, $C_3$-$C_{10}$ cyclokalkyl, $C_3$-$C_{10}$ cycloalkylmethyl, $C_3$-$C_{10}$ alkene, $C_3$-$C_{10}$ alkyne, aryl, $C_5$-$C_{20}$ alkaryl, fused $C_5$-$C_{20}$ aryl or alkaryl and a hydrocarbon chain containing a heterocyclic or fused ring, any of which may be optionally substituted;

$X^3$ and $X^4$ are the same or different and are selected from the group consisting of: a bond $CR^{24}R^{25}$, O, $NR^{26}$, and S;

$R^{24}$ and $R^{25}$ are the same or different and are selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{14}$, $SO_3H$, $SO_2NR^{15}R^{16}$, $SO_2R^{14}$, $SONR^{15}R^{16}$, $SOR^{14}$, $COR^{14}$, COOH, $COOR^{14}$, $CONR^{15}R^{16}$, $NR^{15}COR^{14}$, $NR^{15}COOR^{14}$, $NR^{15}SO_2R^{14}$, $NR^{15}CONR^{16}R^{17}$, $NR^{15}R^{16}$, and acyl; and $R^{26}$ is selected from the group consisting of: H, an N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl.

In some embodiments of the third aspect of the invention, $R^{22}$ and $R^{23}$ are fused to form a 5 or 6 membered cycloalkyl, cycloalkenyl, heterocycloalkyl, heterocycloalkenyl, aryl or heteroaryl ring, each of which may be optionally substituted:

In some embodiments of the third aspect of the invention, $X^1$ is selected from the group consisting of: C=O and $SO_2$.

In some embodiments of the third aspect of the invention, $X^2$ is N.

In some embodiments of the third aspect of the invention, A is selected from the group consisting of: $CH_2CH_2CH_2$, $CH_2CH_2O$, $CH_2CH_2S$, $CH_2CH_2NR^{13}$, $CH_2CH=CH$, CH=CHCH$_2$, CH=CHC(O), C(O)CH=CH, C=NC(O), $CH_2OC(O)$, C(O)OC(O), $CH_2SC(O)$, C(O)SC(O), C(O)OCH$_2$, C(O)SCH$_2$, C(O)CH$_2NR^{13}$, C(O)CH$_2$S, C(O)CH$_2$O, C(S)CH$_2$O, OC(O), CH$_2$O, C(O)O, CH$_2$S, CH$_2NR^{13}$, CH$_2$CH$_2$, SC(O), C(S)O, C(O)S, C(S)S, C(O)NR$^{13}$, C(S)NR$^{13}$.

In some embodiments of the third aspect of the invention, $R^2$ and $R^3$ are each independently selected from the group consisting of: optionally substituted $C_1$-$C_{12}$ alkyloxy and optionally substituted $C_2$-$C_{12}$ alkynyloxy.

In some embodiments of the third aspect of the invention, the optionally substituted $C_1$-$C_{12}$ alkyloxy is $C_1$-$C_{12}$ fluoroalkyloxy.

In some embodiments of the third aspect of the invention, the optionally substituted $C_2$-$C_{12}$ alkynyloxy is $C_2$-$C_{12}$ alkynylalkyloxy.

In some embodiments of the third aspect of the invention, $R^2$ is selected from the group consisting of: $H_3CO$, $F_2HCF_2CO$, $F_2HCO$, $F_3CO$, and $CHCCH_2O$.

In some embodiments of the third aspect of the invention, $R^3$ is selected from the group consisting of: $H_3CO$, $F_2HCF_2CO$, $F_2HCO$, $F_3CO$, and $CHCCH_2O$.

In some embodiments of the third aspect of the invention, $R^2$ and $R^3$ together are selected from the group consisting of: $OCF_2CF_2CO$, $OCH_2CH_2O$, $OCF_2O$, and $OCH_2O$.

In some embodiments of the third aspect of the invention, T is selected from the group consisting of: a double bond and

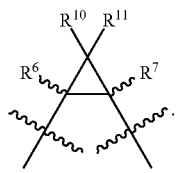

In some embodiments of the third aspect of the invention, $R^6$ is selected from the group consisting of: H and $C_1$-$C_6$ alkyl.

In some embodiments of the third aspect of the invention, $R^7$ is selected from the group consisting of: H, CN, $NO_2$ and $C_1$-$C_6$ alkyl.

In some embodiments of the third aspect of the invention, $R^1$ is selected from the group consisting of: H and optionally substituted $C_1$-$C_6$ alkoxy.

In some embodiments of the third aspect of the invention, $R^4$ is selected from the group consisting of: H and optionally substituted $C_1$-$C_6$ alkoxy.

In some embodiments of the third aspect of the invention, $R^5$ is H.

In some embodiments of the third aspect of the invention, $R^8$ is selected from the group consisting of: H, halogen, $COOR^{18}$, $COR^{18}$, $CONR^{19}R^{20}$, $R^{19}R^{20}$, $SO_2R^{18}$, and $SONR^{19}R^{20}$.

In some embodiments of the third aspect of the invention, $R^8$ is selected from the group consisting of: H, halogen, COOH, $CONH_2$, $CONHCH_3$, CONHOH, $NH_2$, $SO_2CH_3$, $SO_2NH_2$, $SONHCH_3$, and $SON(CH_3)_2$.

In some embodiments of the third aspect of the invention, n is 1.

In some embodiments of the third aspect of the invention the compound of Formula (III) is selected from the group consisting of:

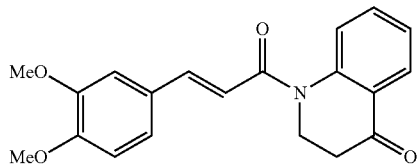

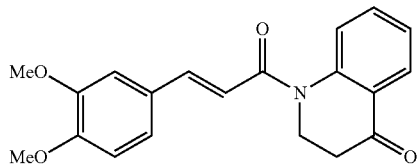

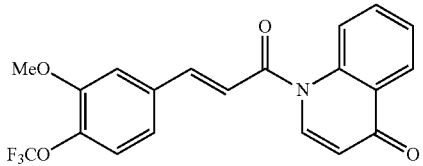

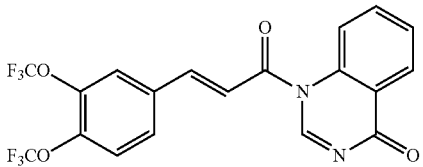

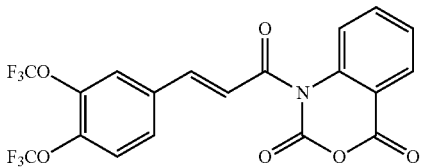

-continued

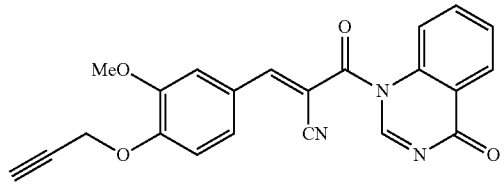

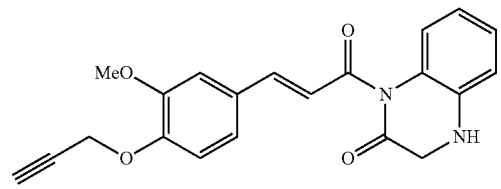

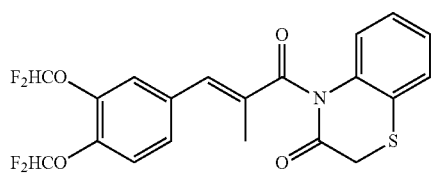

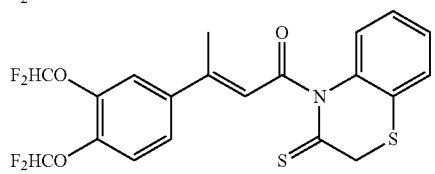

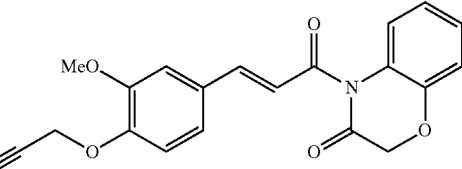

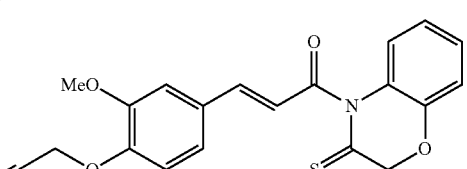

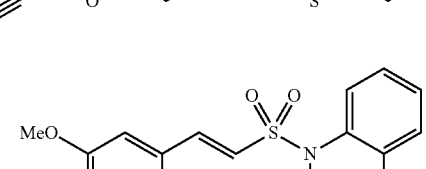

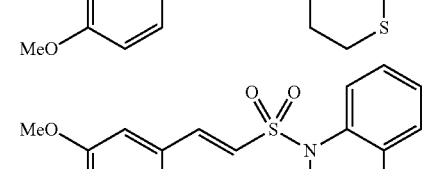

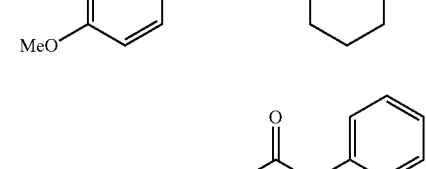

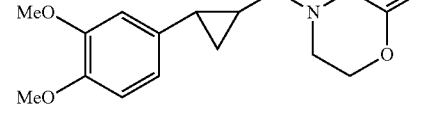

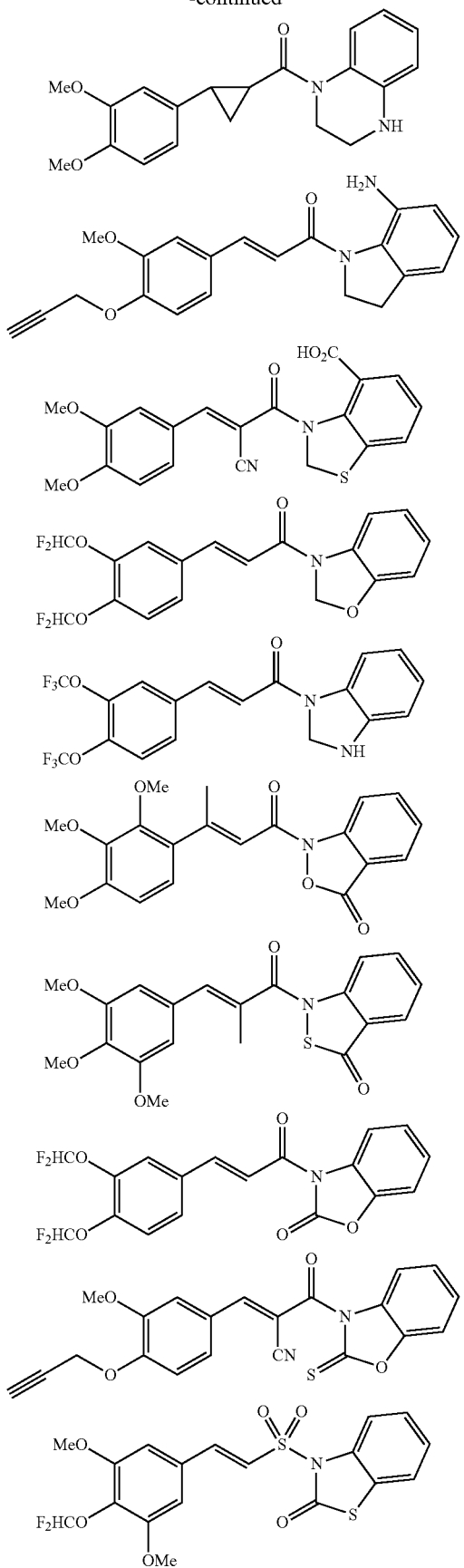
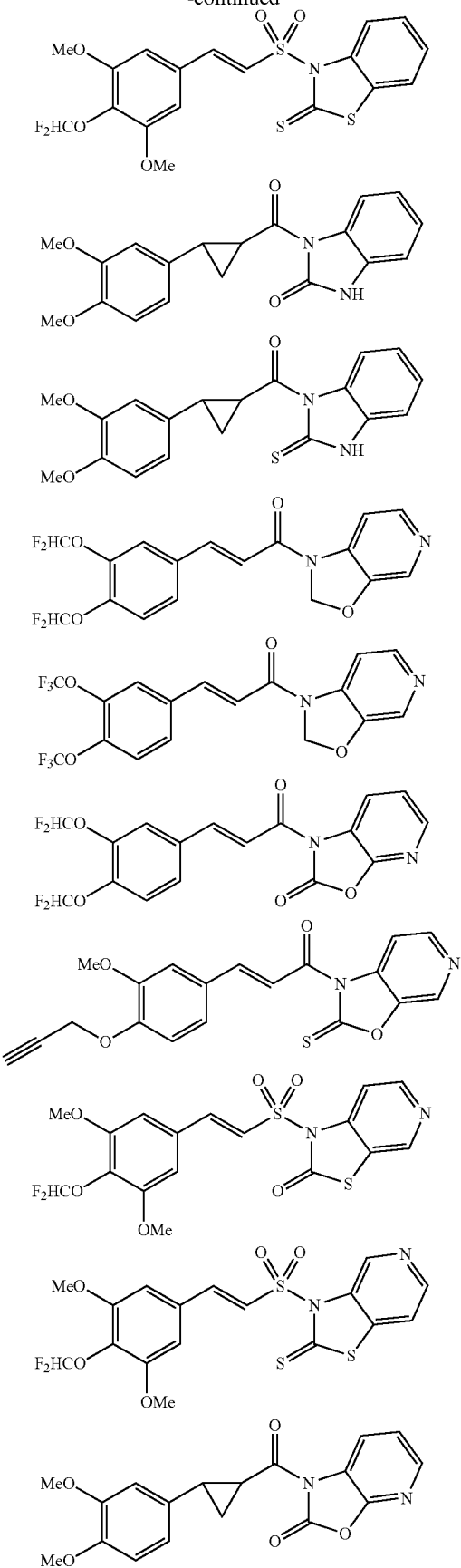

25

-continued

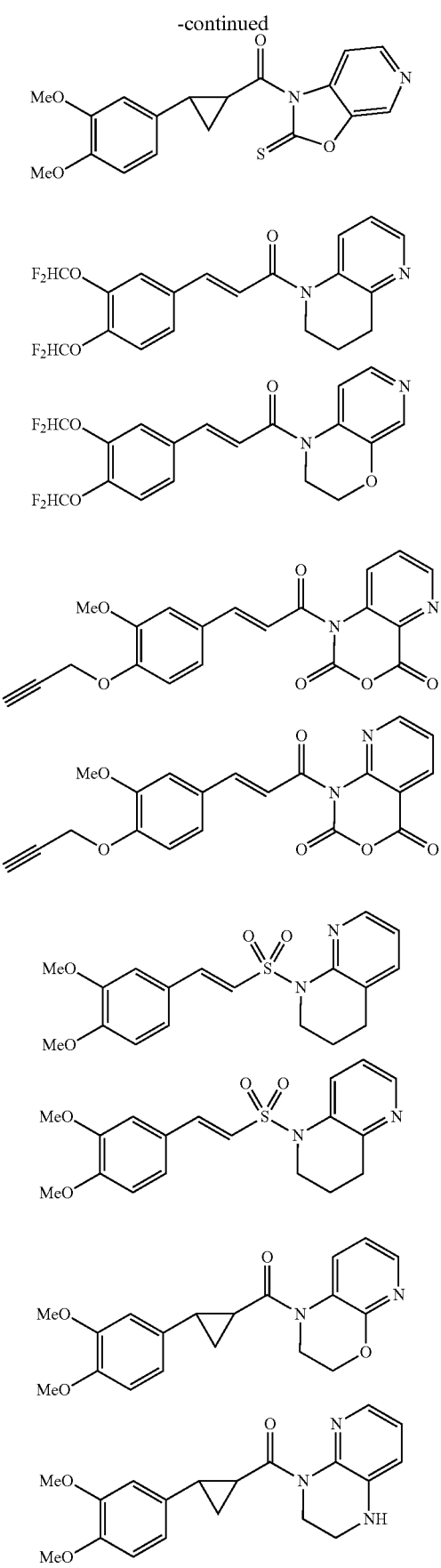

26

-continued

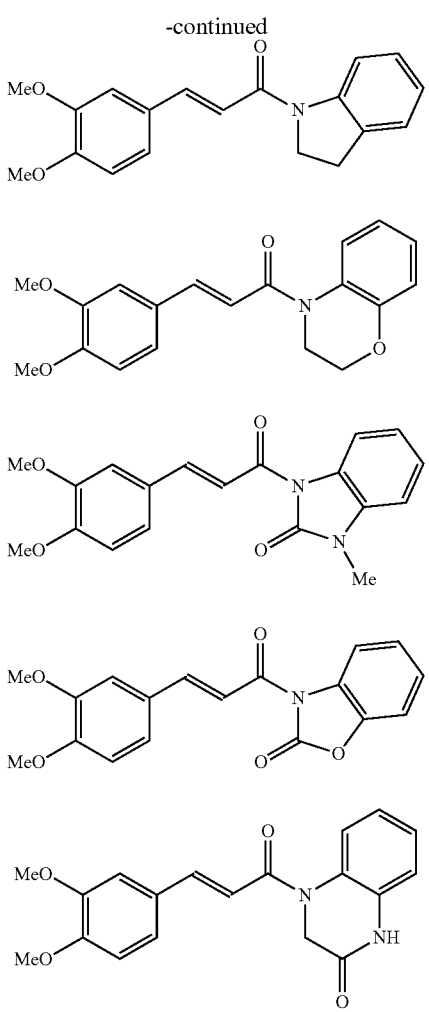

or a pharmaceutically acceptable salt or prodrug thereof.

In a fourth aspect, the present invention provides a compound of Formula (IV)

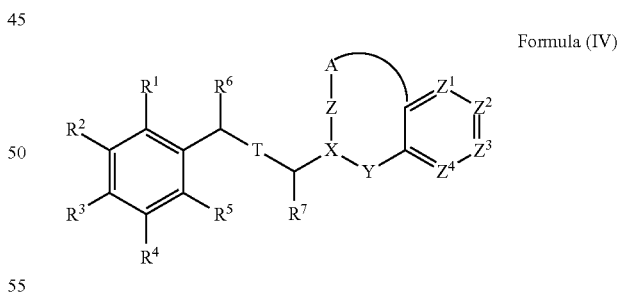

Formula (IV)

or a pharmaceutically acceptable salt or prodrug thereof, wherein:

Z—X—Y is selected from the group consisting of: N=C—N, N—C=N, O—C=N, S—C=N, N=C—O, N=C—S, C=C—NH, C=C—O, C=C—S, and C(O)—C=N;

A is selected from the group consisting of: a bond, $SO_2$, C, C=S, C=O, C=NR$^9$, and NR$^9$;

T is selected from the group consisting of: a single bond, a double bond, a triple bond, and

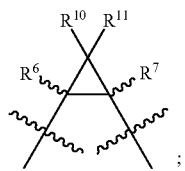

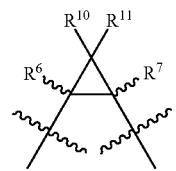

$Z^1$, $Z^2$, $Z^3$, and $Z^4$ are each independently selected from the group consisting of $CR^8$ and N;

$R^1$, $R^4$, $R^5$, $R^8$, $R^{10}$, and $R^{11}$ are each independently selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{12}$, $SO_3H$, $SO_2NR^{13}R^{14}$, $SO_2R^{12}$, $SONR^{13}R^{14}$, $SOR^{12}$, $COR^{12}$, COOH, $COOR^{12}$, $CONR^{13}R^{14}$, $NR^{13}COR^{12}$, $NR^{13}COOR^{12}$, $NR^{13}SO_2R^{12}$, $NR^{13}CONR^{14}R^{15}$, $NR^{14}R^{15}$, and acyl;

$R^2$ and $R^3$, are each independently selected from the group consisting of: H, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted. $C_2$-$C_{12}$ alkynyloxy, optionally substituted $C_1$-$C_{12}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{12}$ heteroaryloxy, optionally substituted $C_1$-$C_{12}$ alkylamino, $SR^{12}$, $SO_3H$, $SO_2NR^{13}R^{14}$, $SO_2R^{12}$, $SONR^{13}R^{14}$, $SOR^{12}$, $COR^{12}$, COOH, $COOR^{12}$, $CONR^{13}R^{14}$, $NR^{13}COR^{12}$, $NR^{13}COOR^{12}$, $NR^{13}SO_2R^{12}$, $NR^{13}CONR^{14}R^{15}$, $NR^{14}R^{15}$, and acyl; or $R^2$ and $R^3$ may be fused to form a 5 or 6 membered cycloalkyl, heterocycloalkyl, aryl or heteroaryl ring each of which may be optionally substituted;

$R^6$ and $R^7$ are present when T is a single bond, a double bond or but not when T is a triple bond, each $R^6$ and $R^7$ being independently selected from the group consisting of: H, $NO_2$, CN, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{12}$, $SO_3H$, $SO_2NR^{13}R^{14}$, $SO_2R^{12}$, $SONR^{13}R^{14}$, $SOR^{12}$, $COR^{12}$, COOH, $COOR^{12}$, $CONR^{13}R^{14}$, $NR^{13}COR^{12}$, $NR^{13}COOR^{12}$, $NR^{13}SO_2R^{12}$, $NR^{13}CONR^{14}R^{15}$, $NR^{14}R^{15}$, and acyl;

$R^9$, $R^{13}$, $R^{14}$, and $R^{15}$ are each independently selected from the group consisting of: H, an N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

$R^{12}$ is selected from the group consisting of H, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl; and n is an integer selected from the group consisting of: 0, 1, 2, 3, and 4.

In some embodiments of the fourth aspect of the invention, $R^2$ is —$X^2$—$R^{16}$ and $R^3$ is —$X^3$—$R^{17}$, wherein:

$R^{16}$ and $R^{17}$ are the same or different and are selected from the group consisting of: H, halogen, $C_{1-10}$ alkyl, $C_3$-$C_{10}$ cyclokalkyl, $C_3$-$C_{10}$ cycloalkylmethyl, $C_3$-$C_{10}$ alkene, $C_3$-$C_{10}$ alkyne, aryl, $C_5$-$C_{20}$ alkaryl, fused $C_5$-$C_{20}$ aryl or alkaryl and a hydrocarbon chain containing a heterocyclic or fused ring, any of which may be optionally substituted;

$X^2$ and $X^3$ are the same or different and are selected from the group consisting of: a bond $CR^{18}R^{19}$, O, $NR^{20}$, and S;

$R^{18}$ and $R^{19}$ are the same or different and are selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{12}$, $SO_3H$, $SO_2NR^{13}R^{14}$, $SO_2R^{12}$, $SONR^{13}R^{14}$, $SOR^{12}$, $COR^{12}$, COOH, $COOR^{12}$, $CONR^{13}R^{14}$, $NR^{13}COR^{12}$, $NR^{13}COOR^{12}$, $NR^{13}SO_2R^{12}$, $NR^{13}CONR^{14}R^{15}$, $NR^{14}R^{15}$, and acyl; and $R^{20}$ is selected from the group consisting of: H, an N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl.

In some embodiments of the fourth aspect of the invention, $R^{16}$ and $R^{17}$ are fused to form a 5 or 6 membered cycloalkyl, heterocycloalkyl, cycloalkenyl, heterocycloalkenyl, aryl or heteroaryl ring, each of which may be optionally substituted.

In some embodiments of the fourth aspect of the invention, $R^2$ and $R^3$ are each independently selected from the group consisting of: optionally substituted $C_1$-$C_{12}$ alkyloxy and optionally substituted $C_2$-$C_{12}$ alkynyloxy.

In some embodiments of the fourth aspect of the invention, the optionally substituted $C_1$-$C_{12}$ alkyloxy is $C_1$-$C_{12}$ fluoroalkyloxy.

In some embodiments of the fourth aspect of the invention, the optionally substituted $C_2$-$C_{12}$ alkynyloxy is $C_2$-$C_{12}$ alkynylalkyloxy.

In some embodiments of the fourth aspect of the invention, $R^2$ is selected from the group consisting of: $H_3CO$, $F_2HCF_2CO$, $F_2HCO$, $F_3CO$, and $CHCCH_2O$.

In some embodiments of the fourth aspect of the invention, $R^3$ is selected from the group consisting of: $H_3CO$, $F_2HCF_2CO$, $F_2HCO$, $F_3CO$, and $CHCCH_2O$.

In some embodiments of the fourth aspect of the invention, $R^2$ and $R^3$ together are selected from the group consisting of: $OCF_2CF_2CO$, $OCH_2CH_2O$, $OCF_2O$, and $OCH_2O$.

In some embodiments of the fourth aspect of the invention, T is selected from the group consisting of: a double bond and

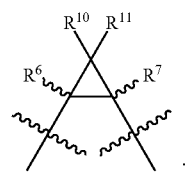

In some embodiments of the fourth aspect of the invention, $R^6$ is selected from the group consisting of: H and $C_1$-$C_6$alkyl.

In some embodiments of the fourth aspect of the invention, $R^7$ is selected from the group consisting of: H, CN, $NO_2$, and $C_1$-$C_6$ alkyl.

In some embodiments of the fourth aspect of the invention, $R^1$ is selected from the group consisting of: H and optionally substituted $C_1$-$C_6$ alkoxy.

In some embodiments of the fourth aspect of the invention, $R^4$ is selected from the group consisting of: H and optionally substituted $C_1$-$C_6$ alkoxy.

In some embodiments of the fourth aspect of the invention, $R^5$ is H.

In some embodiments of the fourth aspect of the invention, $R^8$ is selected from the group consisting of: H, halogen, $COOR^{12}$, $COR^{12}$, $CONR^{13}R^{14}$, $NR^{13}R^{14}$, $SO_2R^{12}$, and $SONR^{13}R^{14}$.

In some embodiments of the fourth aspect of the invention, $R^8$ is selected from the group consisting of: H, halogen, COOH, $CONH_2$, CONHOH, $CONHCH_3$, $NH_2$, $SO_2CH_3$, $SO_2NH_2$, $SONHCH_3$, and $SON(CH_3)_2$.

In some embodiments of the fourth aspect of the invention, n is 1.

In some embodiments of the fourth, aspect of the invention, the $R^8$ group is in the position ortho to the Y group.

In some embodiments of the fourth aspect of the invention the compound of formula (IV) is selected from the group consisting of:

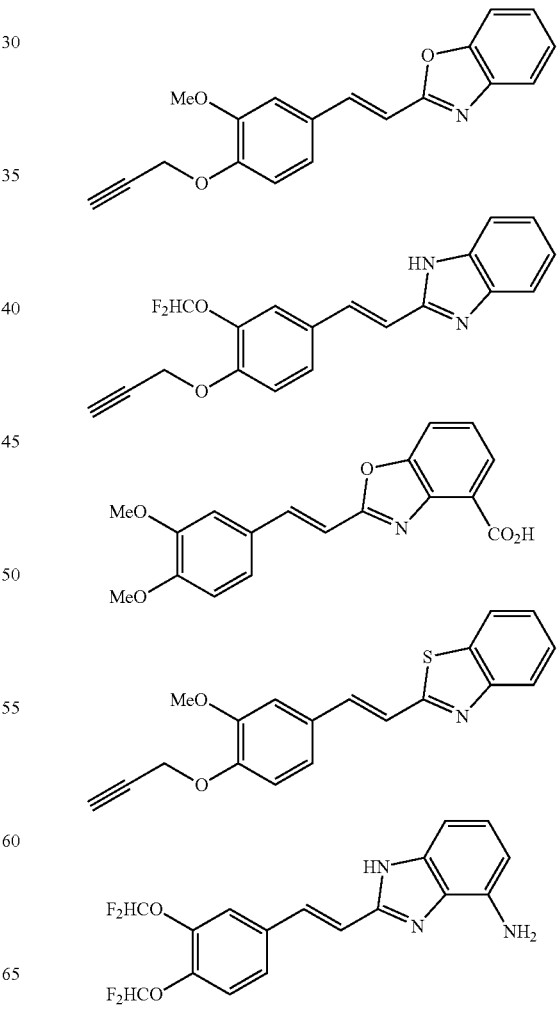

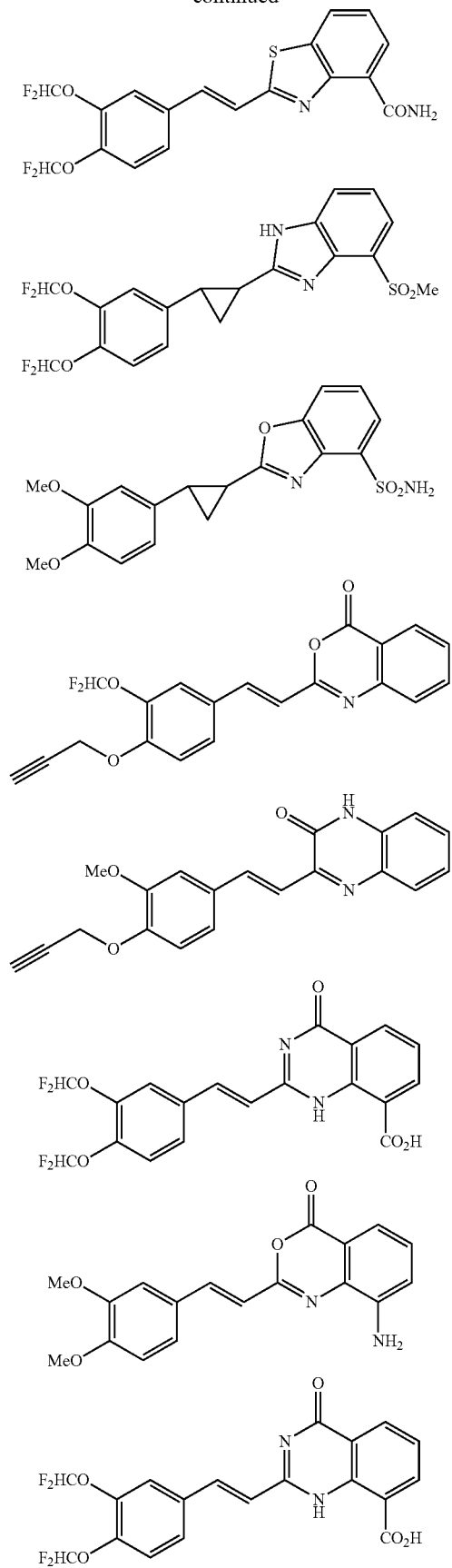
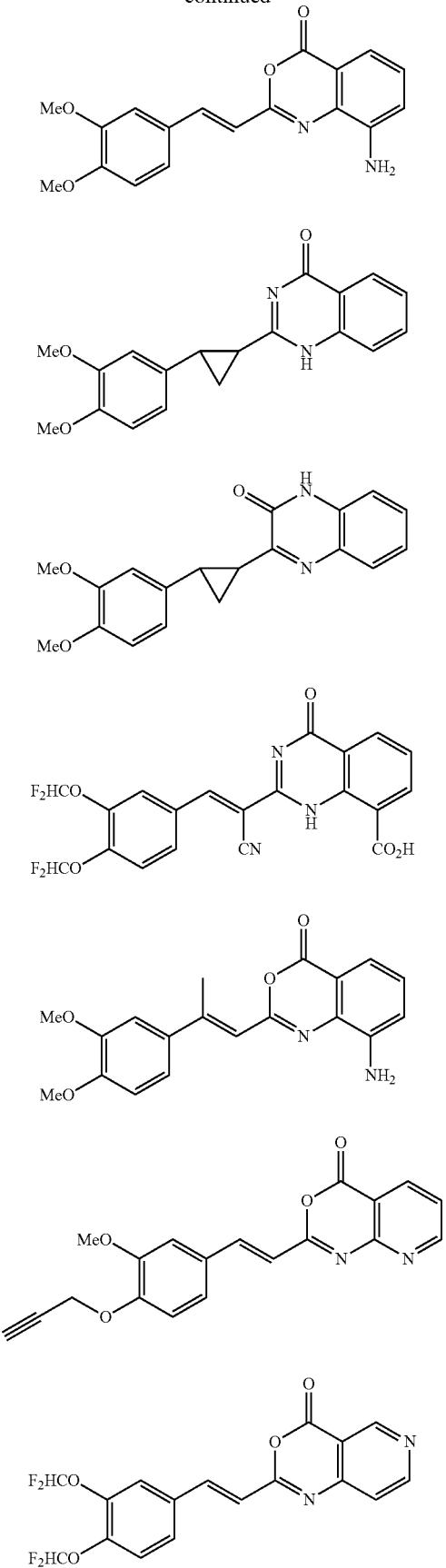

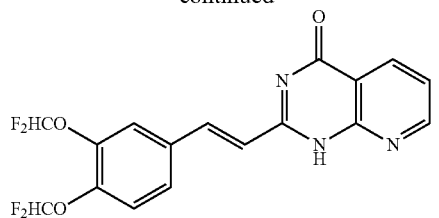

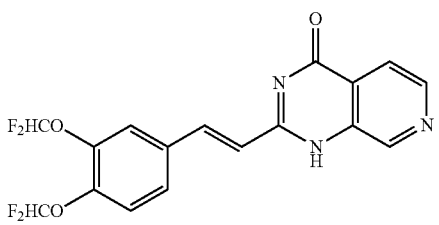

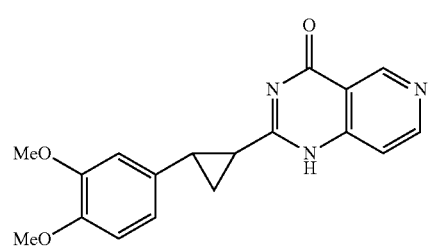

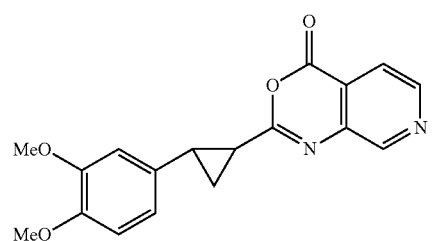

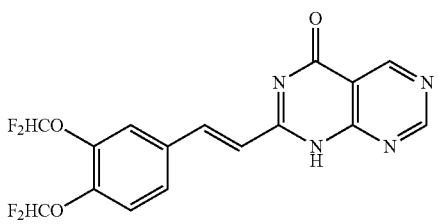

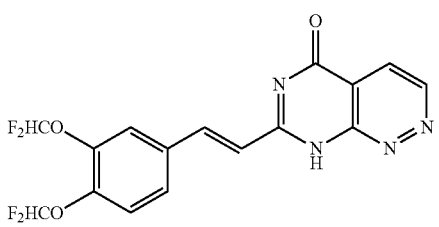

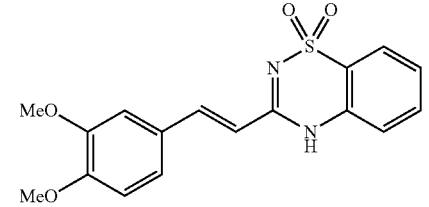

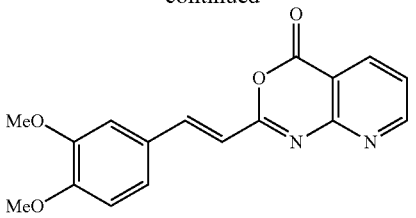

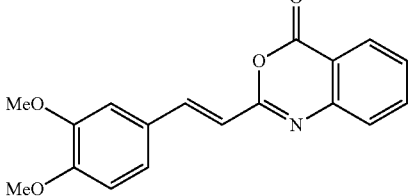

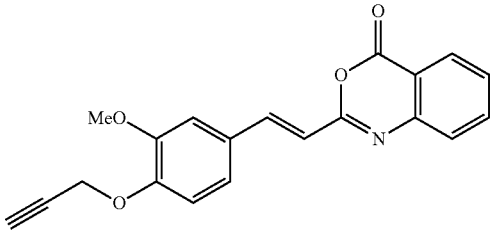

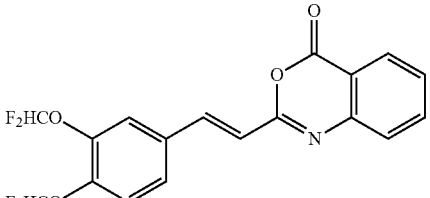

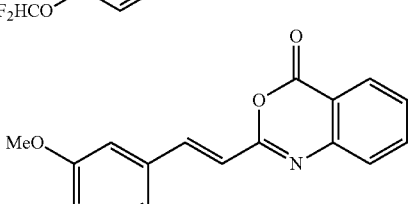

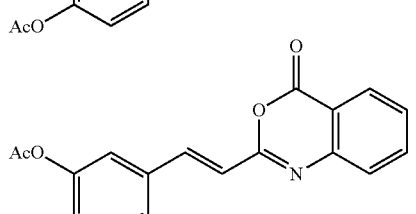

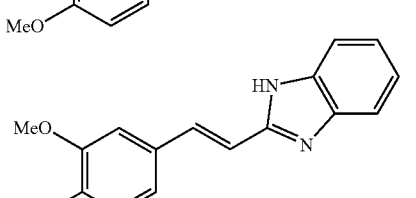

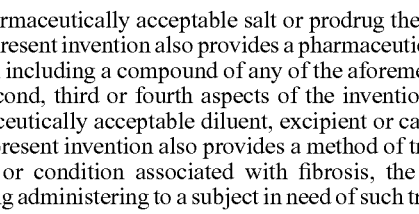

or a pharmaceutically acceptable salt or prodrug thereof.

The present invention also provides a pharmaceutical composition including a compound of any of the aforementioned first, second, third or fourth aspects of the invention, and a pharmaceutically acceptable diluent, excipient or carrier.

The present invention also provides a method of treating a disease or condition associated with fibrosis, the method including administering to a subject in need of such treatment a therapeutically effective amount of a compound of any of the aforementioned first, second, third or fourth aspects of the invention. The disease or condition may be selected from the group consisting of fibrotic skin disorders, lung disease, heart disease and kidney disease.

The present invention also provides a method of treating a disease or condition characterised by inflammation and/or a benign or malignant neoplastic disease, the method including administering to a subject in need of such treatment a therapeutically effective amount of a compound of any of the aforementioned first, second, third or fourth aspects of the invention.

The present invention also provides a method of inhibiting fibrosis in a subject, the method including administering to the subject a therapeutically effective amount of a compound of any of the aforementioned first, second, third or fourth aspects of the invention.

The present invention also provides a use of a compound of any of the aforementioned first, second, third or fourth aspects of the invention to inhibit fibrosis.

The present invention also provides a use of a compound of any of the aforementioned first, second, third or fourth aspects of the invention in the treatment of a disease or condition associated with fibrosis.

The present invention also provides a use of a compound of any of the aforementioned first, second, third or fourth aspects of the invention in the treatment of a disease or condition characterised by inflammation and/or a benign or malignant neoplastic disease.

The present invention also provides a use of a compound of any of the aforementioned first, second, third or fourth aspects of the invention in the preparation of a medicament for treating a disease or condition associated with fibrosis.

The present invention also provides a use of a compound of any of the aforementioned first, second, third or fourth aspects of the invention in the preparation of a medicament for treating a disease or condition characterised by inflammation and/or a benign or malignant neoplastic disease.

DETAILED DESCRIPTION OF THE INVENTION

In this specification a number of terms are used which are well known to a skilled addressee. Nevertheless for the purposes of clarity a number of terms will be defined.

As used herein, the term "unsubstituted" means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkoxy, alkoxyalkyl, alkoxycycloalkyl, alkoxyheterocycloalkyl, alkoxyaryl, alkoxyheteroaryl, alkoxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, arylalkyl, heteroarylalkyl, cycloalkylalkyl, heterocycloalkylalkyl, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —COOH, —COR$^{11}$, —C(O)OR$^{11}$, CONHR$^{11}$, NHCOR$^{11}$, NHCOOR$^{11}$, NHCONHR$^{11}$, C(=NOH)R$^{11}$, —SH, —SR$^{11}$, —OR$^{11}$ and acyl.

"Alkyl" as a group or part of a group refers to a straight or branched aliphatic hydrocarbon group, preferably a $C_1$-$C_{14}$ alkyl, more preferably $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl; n-butyl, sec-butyl, t-butyl, hexyl, and the like. The group may be a terminal group or a bridging group.

"Alkylamino" includes both mono-alkylamino and dialkylamino, unless specified. "Mono-alkylamino" means a —NH-Alkyl group, in which alkyl is as defined above. "Dialkylamino" means a —N(alkyl)$_2$ group, in which each alkyl may be the same or different and are each as defined herein for alkyl. The alkyl group is preferably a $C_1$-$C_6$ alkyl group. The group may be a terminal group or a bridging group.

"Arylamino" includes both mono-arylamino and di-arylamino unless specified. Mono-arylamino means a group of formula aryl NH—, in which aryl is as defined herein. di-arylamino means a group of formula (aryl)$_2$N— where each aryl may be the same or different and are each as defined herein for aryl. The group may be a terminal group or a bridging group.

"Acyl" means an alkyl-CO— group in which the alkyl group is as described herein. Examples of acyl include acetyl and benzoyl. The alkyl group is preferably a $C_1$-$C_6$ alkyl group. The group may be a terminal group or a bridging group.

"Alkenyl" as a group or part of a group denotes an aliphatic hydrocarbon group containing at least one carbon-carbon double bond and which may be straight or branched preferably having 2-14 carbon atoms, more preferably 2-12 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkoxy" refers to an —O-alkyl group in which alkyl is defined herein. Preferably the alkoxy is a $C_1$-$C_6$ alkoxy. Examples include, but are not limited to, methoxy and ethoxy. The group may be a terminal group or a bridging group.

"Alkenyloxy" refers to an —O— alkenyl group in which alkenyl is as defined herein. Preferred alkenyloxy groups are $C_1$-$C_6$ alkenyloxy groups. The group may be a terminal group or a bridging group.

"Alkynyloxy" refers to an —O-alkynyl group in which alkynyl is as defined herein. Preferred alkynyloxy groups are $C_1$-$C_6$ alkynyloxy groups. The group may be a terminal group or a bridging group.

"Alkoxycarbonyl" refers to an —C(O)—O-alkyl group in which alkyl is as defined herein. The alkyl group is preferably a $C_1$-$C_6$ alkyl group. Examples include, but not limited to, methoxycarbonyl and ethoxycarbonyl. The group may be a terminal group or a bridging group.

"Alkylsulfinyl" means a —S(O)-alkyl group in which alkyl is as defined above. The alkyl group is preferably a $C_1$-$C_6$ alkyl group. Exemplary alkylsulfinyl groups include, but not limited to, methylsulfinyl and ethylsulfinyl. The group may be a terminal group or a bridging group.

"Alkylsulfonyl" refers to a —S(O)$_2$-alkyl group in which alkyl is as defined above. The alkyl group is preferably a $C_1$-$C_6$ alkyl group. Examples include, but not limited to methylsulfonyl and ethylsulfonyl. The group may be a terminal group or a bridging group.

"Alkynyl" as a group or part of a group means an aliphatic hydrocarbon group containing a carbon-carbon triple bond and which may be straight or branched preferably having from 2-14 carbon atoms, more preferably 2-12 carbon atoms, more preferably 2-6 carbon atoms in the normal chain. Exemplary structures include, but are not limited to, ethynyl and propynyl. The group may be a terminal group or a bridging group.

"Alkylaminocarbonyl" refers to an alkylamino-carbonyl group in which alkylamino is as defined above. The group may be a terminal group or a bridging group.

"Cycloalkyl" refers to a saturated or partially saturated, monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. The group may be a terminal group or a bridging group.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. The group may be a terminal group or a bridging group.

The above discussion of alkyl and cycloalkyl substituents also applies to the alkyl portions of other substituents, such as without limitation, alkoxy, alkyl amines, alkyl ketones, arylalkyl, heteroarylalkyl, alkylsulfonyl and alkyl ester substituents and the like.

"Cycloalkylalkyl" means a cycloalkyl-alkyl-group in which the cycloalkyl and alkyl moieties are as previously described. Exemplary monocycloalkylalkyl groups include cyclopropylmethyl, cyclopentylmethyl, cyclohexylmethyl and cycloheptylmethyl. The group may be a terminal group or a bridging group.

"Halogen" represents fluorine, chlorine, bromine or iodine.

"Heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. The group may be a terminal group or a bridging group.

"Heterocycloalkenyl" refers to a heterocycloalkyl as described above but containing at least one double bond. The group may be a terminal group or a bridging group.

"Heterocycloalkylalkyl" refers to a heterocycloalkyl-alkyl group in which the heterocycloalkyl and alkyl moieties are as previously described. Exemplary heterocycloalkylalkyl groups include (2-tetrahydrofuryl)methyl, (2-tetrahydrothiofuranyl)methyl. The group may be a terminal group or a bridging group.

"Heteroalkyl" refers to a straight- or branched-chain alkyl group preferably having from 2 to 14 carbons, more preferably 2 to 10 carbons in the chain, one or more of which has been replaced by a heteroatom selected from S, O, P and N. Exemplary heteroalkyls include alkyl ethers, secondary and tertiary alkyl amines, amides, alkyl sulfides, and the like. The group may be a terminal group or a bridging group. As used herein reference to the normal chain when used in the context of a bridging group refers to the direct chain of atoms linking the two terminal positions of the bridging group.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group.

"Arylalkenyl" means an aryl-alkenyl-group in which the aryl and alkenyl are as previously described. Exemplary arylalkenyl groups include phenylallyl. The group may be a terminal group or a bridging group.

"Arylalkyl" means an aryl-alkyl-group in which the aryl and alkyl moieties are as previously described. Preferred arylalkyl groups contain a $C_{1-5}$ alkyl moiety. Exemplary arylalkyl groups include benzyl, phenethyl and naphthelenemethyl. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. The group may be a terminal group or a bridging group.

"Heteroarylalkyl" means a heteroaryl-alkyl group in which the heteroaryl and alkyl moieties are as previously described. Preferred heteroarylalkyl groups contain a lower alkyl moiety. Exemplary heteroarylalkyl groups include pyridylmethyl. The group may be a terminal group or a bridging group.

"Lower alkyl" as a group means unless otherwise specified, an aliphatic hydrocarbon group which may be straight or branched having 1 to 6 carbon atoms in the chain, more preferably 1 to 4 carbons such as methyl, ethyl, propyl (n-propyl or isopropyl) or butyl (n-butyl, isobutyl or tertiary-butyl). The group may be a terminal group or a bridging group.

As would be understood by the skilled person, throughout the synthesis of the compounds of Formulae (I), (II), (III) and (IV) it may be necessary to employ a protecting group on the amino group and/or on the carboxyl group in order to reversibly preserve a reactive amino or carboxyl functionality while reacting other functional groups on the compound. In such a case, the free amino group and/or the free carboxyl groups of the compounds of Formulae (I), (II), (III) and (IV) can be liberated either by deprotection of the amino group followed by deprotection of the acid moieties or vice versa.

Examples of suitable amino protecting groups that may be used include formyl, trityl, phthalimido, trichloroacetyl, chloroacetyl, bromoacetyl, iodoacetyl, and urethane-type blocking groups such as benzyloxycarbonyl ('CBz'), 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl ('tBoc'), 2-(4-xenyl)-isopropoxycarbonyl, 1,1-diphenyleth-1-yloxycarbonyl, 1,1-diphenylprop-1-yloxycarbonyl, 2-phenylprop-2-yloxycarbonyl, 2-(p-toluoyl)-prop-2-yloxycarbonyl, cyclopentanyloxy-carbonyl, 1-methylcyclopentanyloxycarbonyl, cyclohexanyloxycarbonyl, 1-methylcyclohexanyloxycarbonyl, 2-methylcyclohexanyloxycarbonyl; 2-(4-toluoylsulfono)-ethoxycarbonyl, 2-(methylsulfono)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decycloxy)benzyloxycarbonyl, isobornyloxycarbonyl, 1-piperidyloxycarbonlyl and the like; benzoylmethylsulfono group, 2-nitrophenylsulfenyl, diphenylphosphine oxide, and the like. The actual amino protecting group employed is not critical so long as the derivatised amino group is stable to the condition of subsequent reaction(s) and can be selectively removed as required without substantially disrupting the remainder of the molecule including any other amino protecting group(s). Preferred amino-protecting groups are t-butoxycarbonyl (Boc), and benzyloxycarbonyl (Cbz). Further examples of these groups are found in: Greene, T. W. and Wuts, P. G. M., Protective Groups in Organic Synthesis, Second edition; Wiley-Interscience: 1991; Chapter 7; McOmie, J. F. W. (ed.), Protective Groups in Organic Chemistry, Plenum Press, 1973; and Kocienski, P. J., Protecting Groups, Second Edition, Theime Medical Pub., 2000.

Examples of carboxyl protecting groups that may be used include methyl, ethyl, n-propyl, i-propyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2'4,4'-tetramethoxybenzhydryl, t-butyl, t-amyl, trityl, 4-methoxytrityl, 4,4'-dimethoxytrityl, 4,4,'4"-trimethoxytrityl, 2-phenylprop-2-yl, trimethylsilyl, t-butyldimethylsilyl, phenacyl, 2,2,2-trichloroethyl, 3-(di(n-butyl)methylsilyl)ethyl, p-toluenesulfonoethyl, 4-nitrobenzylsulfonoethyl, allyl, cinnamyl, 1-(trimethylsilylmethyl)prop-1-en-3-yl, and the like. Preferred carboxyl protecting groups are methyl and t-butyl. Further examples of these groups are found in: Greene, T. W. and Wuts, P. G. M., Protective Groups in Organic Synthesis, Second edition; Wiley-Interscience: 1991; McOmie, J. F. W. (ed.), Protective Groups in Organic Chemistry, Plenum Press, 1973; and Kocienski, P. J., Protecting Groups, Second Edition, Theime Medical Pub., 2000.

It is understood that included in the family of compounds of Formulae (I), (II), (III) and (IV) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers; and geometrical isomers can be separated by physical and/or chemical methods and by those skilled in the art.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Some of the compounds of the disclosed embodiments are substituted cyclopropanes having the general formula

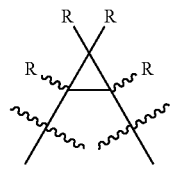

The structure shown is intended to include isomeric forms of the cyclopropanes including diastereoisomers and enantiomers.

Additionally, Formulae (I) to (IV) are intended to cover, where applicable, solvated as well as unsolvated forms of the compounds. Thus, each formula includes compounds having the indicated structure, including the hydrated as well as the non-hydrated forms.

In addition to compounds of Formulae (I) to (IV), the compounds of the various embodiments include pharmaceutically acceptable salts, prodrugs, N-oxides and active metabolites of such compounds, and pharmaceutically acceptable salts of such metabolites.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formulae (I) to (IV) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Suitable pharmaceutically acceptable base addition salts of compounds of Formulae (I) to (IV) include metallic salts made from lithium, sodium, potassium, magnesium, calcium, aluminium, and zinc, and organic salts made from organic bases such as choline, diethanolamine, morpholine. Other examples of organic salts are: ammonium salts, quaternary salts such as tetramethylammonium salt; amino acid addition salts such as salts with glycine and arginine. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

"Prodrug" means a compound which is convertible in vivo by metabolic means (e.g. by hydrolysis, reduction or oxidation) to a compound of Formulae (I) to (IV). For example an ester prodrug of a compound of Formulae (I) to (IV) containing a hydroxyl group may be convertible, by hydrolysis in, vivo to the parent molecule. Suitable esters of compounds of Formulae (I) to (IV) containing a hydroxyl group, are for example acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of Formulae (I) to (IV) containing a carboxy group may be convertible by hydrolysis in vivo to the parent molecule. (Examples of ester prodrugs are those described by F. J. Leinweber, Drug Metab. Res., 18:379; 1987).

The terms "treating", "treat", or "treatment" refer generally to amelioration or elimination of a named condition once the condition has been established. The term "prophylaxis" refers generally to treatment to prevent the onset of a named condition or of a process that can lead to the condition ("primary." prophylaxis), or the recurrence of symptoms of a condition.

The term "subject" refers generally to any warm blooded animal such as; but not limited to, a mouse, guinea pig, dog, horse, or human. In an embodiment, the subject is human.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The term "pharmaceutically acceptable" refers generally to a substance or composition that is compatible chemically and/or toxicologically with the other ingredients including a formulation, and/or the subject being treated.

The term "compounds of the present invention" (unless specifically identified otherwise) refers generally to compounds, prodrugs thereof, pharmaceutically acceptable salts of the compounds and/or prodrugs, and hydrates or solvates of the compounds, salts, and/or prodrugs, as well as all stereoisomers (including diastereoisomers and enantiomers), tautomers and isotopically labelled compounds. The compounds of the present invention may exist, in unsolvated as well as solvated forms with pharmaceutically acceptable solvents such as water, ethanol, and the like, and it is intended that the invention embrace both solvated and unsolvated forms.

The term "derivative thereof" when used in reference to compounds of the present invention refers generally to prodrugs, pharmaceutically acceptable salts of the compounds and/or prodrugs, and hydrates or solvates of the compounds, salts, and/or prodrugs.

Compounds of the present invention include compounds of Formula (I)

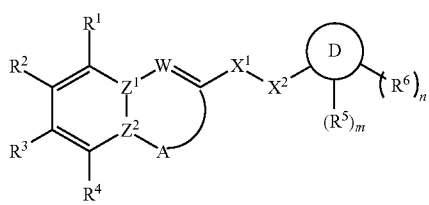

Formula (I)

wherein W, A, Y, $Z^1$—$Z^2$, p, s, q, r, $X^1$, $X^2$, t, D, $R^1$, $R^2$, $R^3$, $R^4$, $R^5$, $R^8$, $R^9$, $R^{10}$, $R^{11}$, $R^{12}$, $R^{13}$, $R^{14}$ $R^{15}$, $R^{18}$, $R^{17}$, m, and n are as previously defined in relation to Formula (I).

Compounds of the present invention also include compounds of Formula (II)

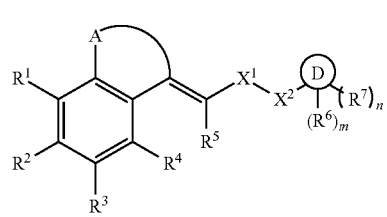

Formula (II)

wherein A, Y, p, s, q, r, $X^1$, $X^2$, D, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{18}$, $R^{17}$, m, and n are as previously defined in relation to Formula (II).

Compounds of the present invention also include compounds of Formula (III)

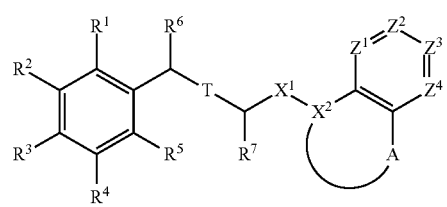

Formula (III)

wherein A, Y, p, s, T, $X^1$, $X^2$, $Z^1$, $Z^2$, $Z^3$, $Z^4$, $R^1$, $R^2$, $R^3$, $R^4$, $R^5$, $R_6$, $R^7$, $R^8$, $R^9$, $R^{10}$, $R^{11}$, $R^{12}$, $R^{13}$, $R^{15}$, $R^{16}$, $R^{17}$, $R^{18}$, $R^{19}$, $R^{20}$ and $R^{21}$ and n are as previously defined in relation to Formula (III).

Compounds of the present invention also include compounds of Formula (IV)

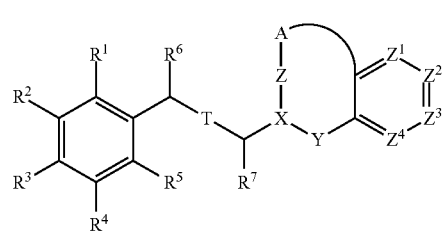

Formula (IV)

wherein: Z—X—Y, A, T, $Z^1$, $Z^2$, $Z^3$, $Z^4$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and n are as previously defined in relation to Formula (IV).

Specific compounds of the invention include the following:

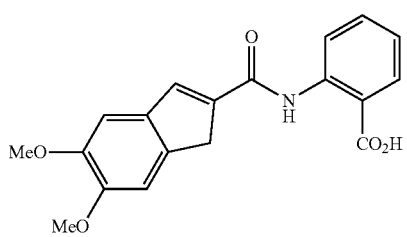

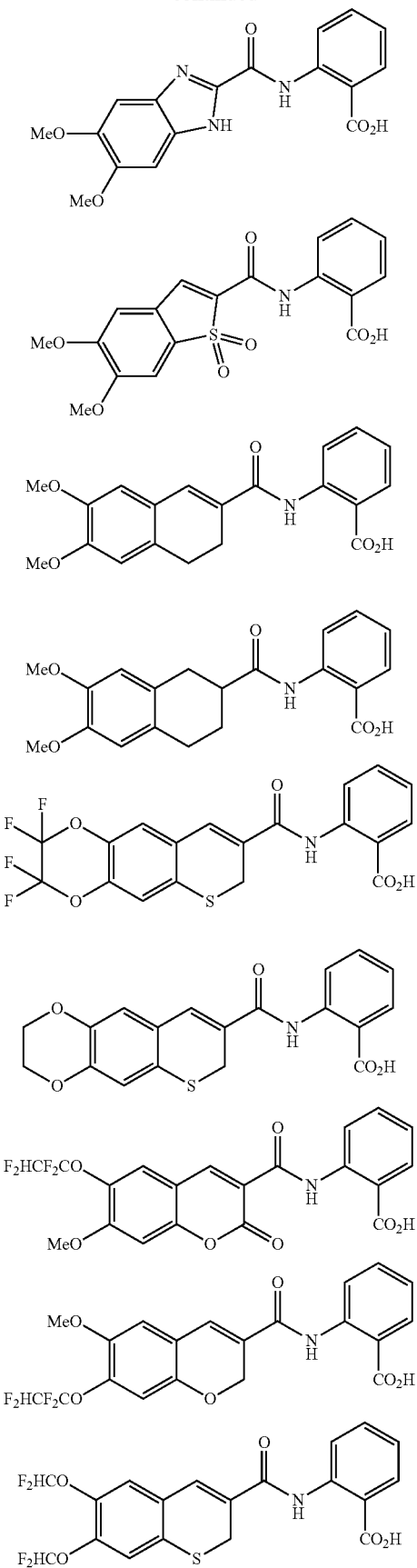
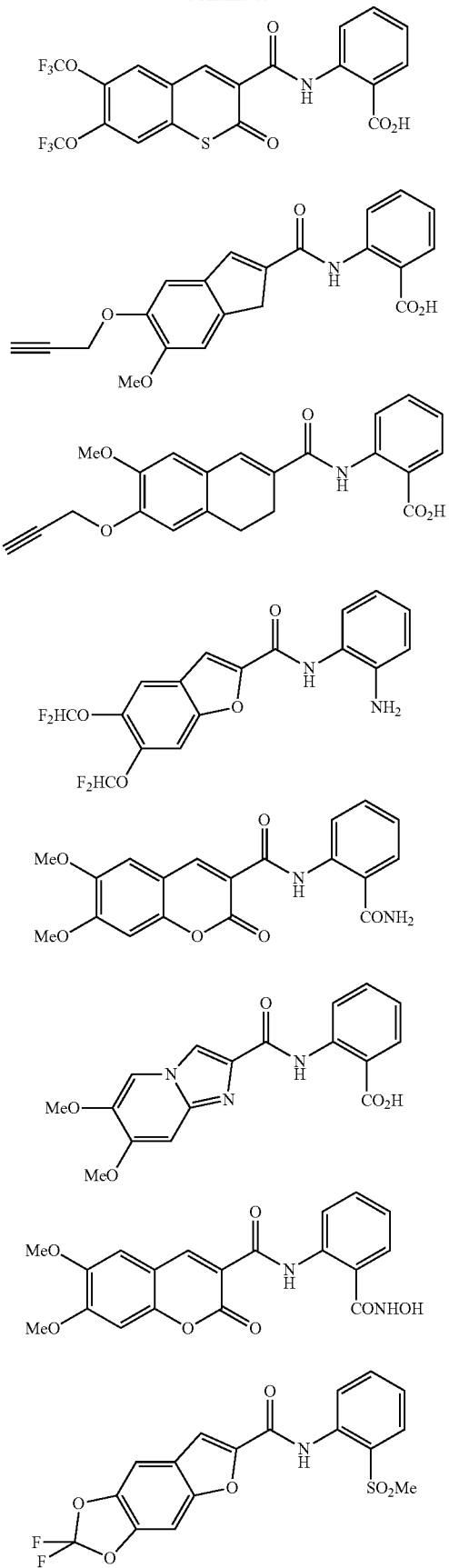

-continued
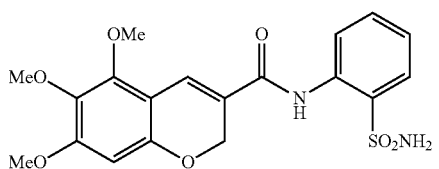
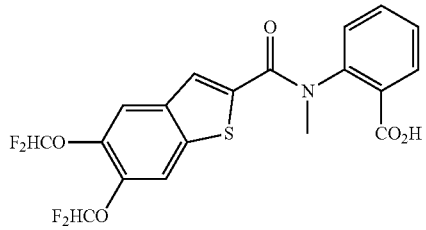
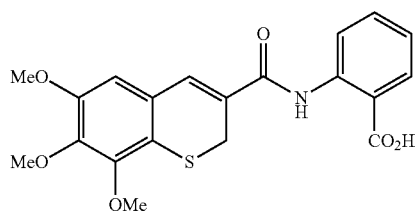
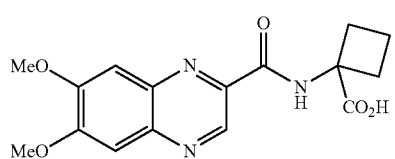
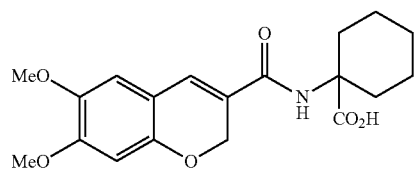
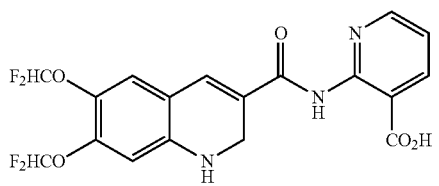
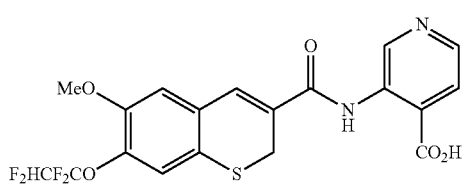
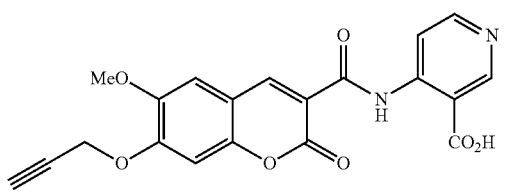
-continued
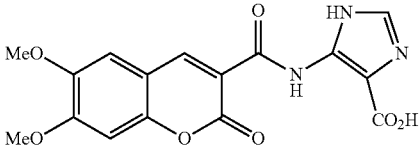
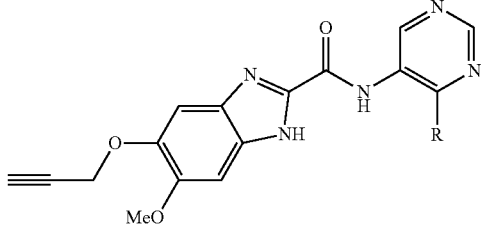
R = SO$_2$Me, SO$_2$NH$_2$, SONHMe, SONMe$_2$
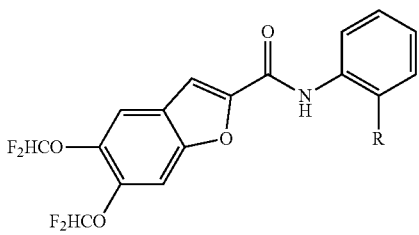
R = NH$_2$, CONH$_2$, CONHMe, CONHOH
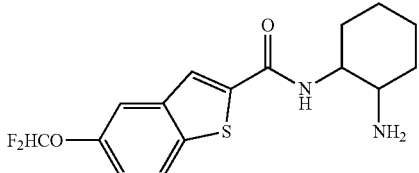
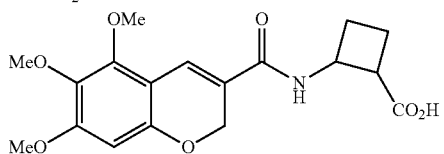
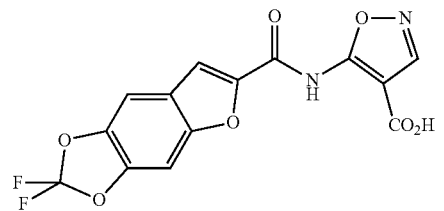
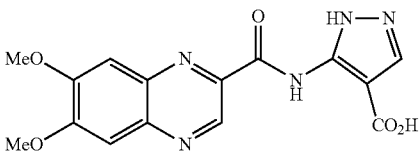
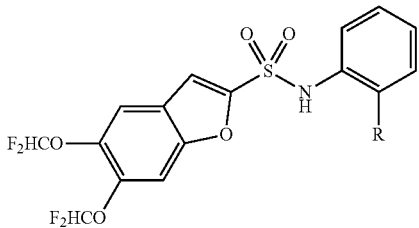
R = SO$_2$Me, SO$_2$NH$_2$, SONHMe, SONMe$_2$ -continued
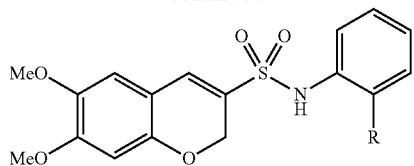
R = NH₂, CONH₂, CONHMe, CONHOH
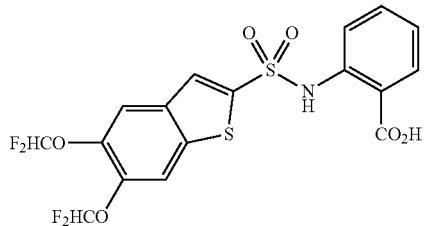
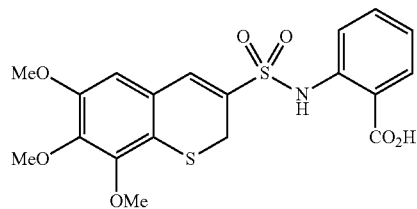
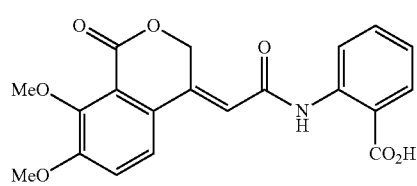
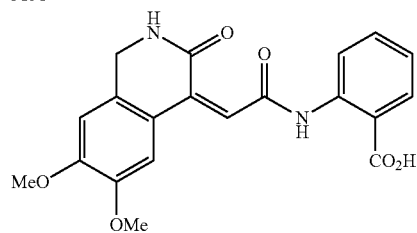
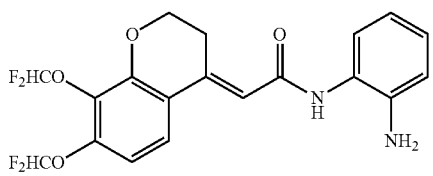
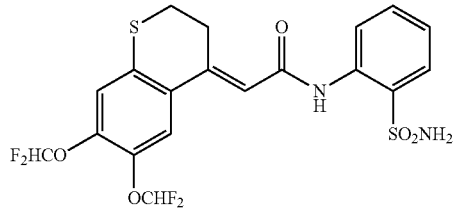
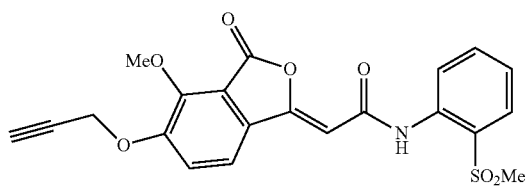
-continued
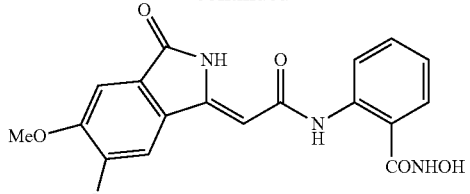
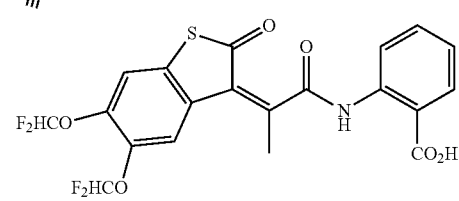
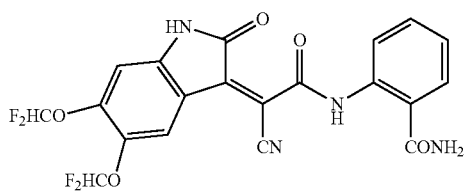
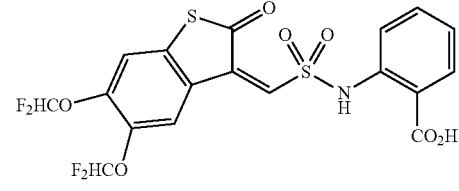
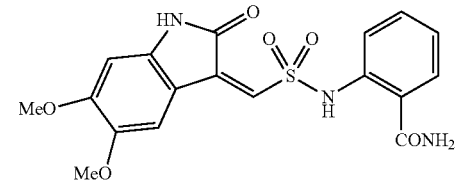
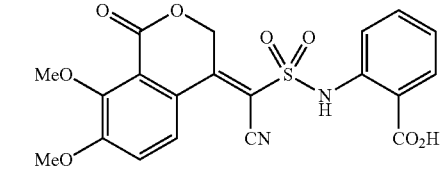
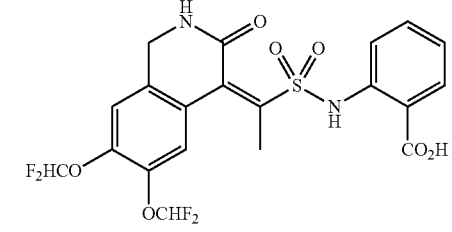
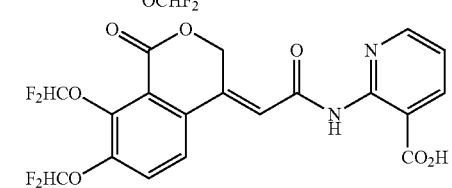

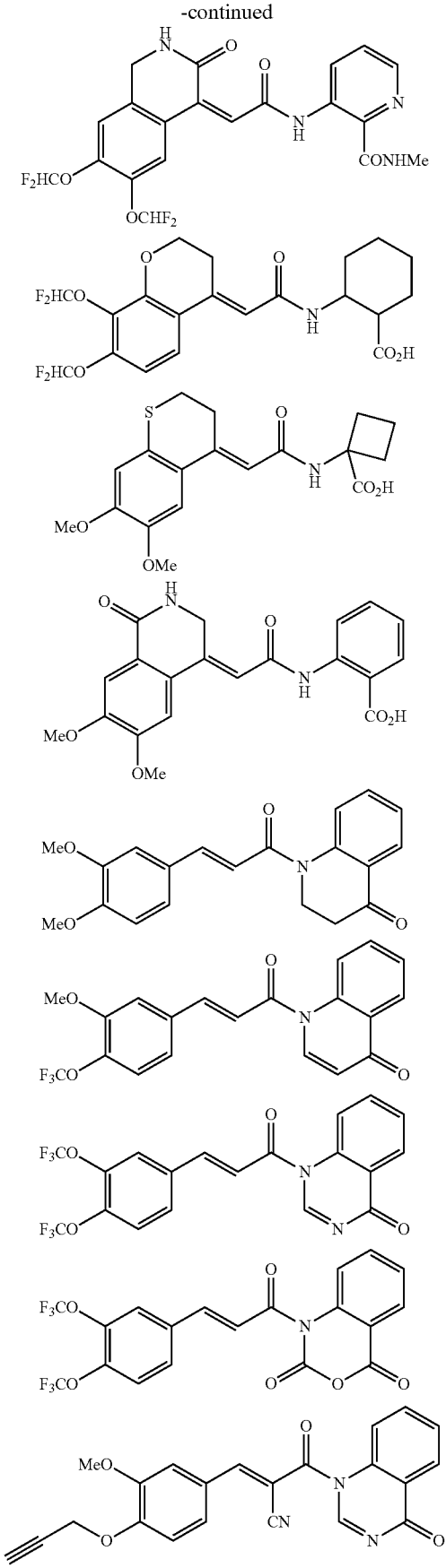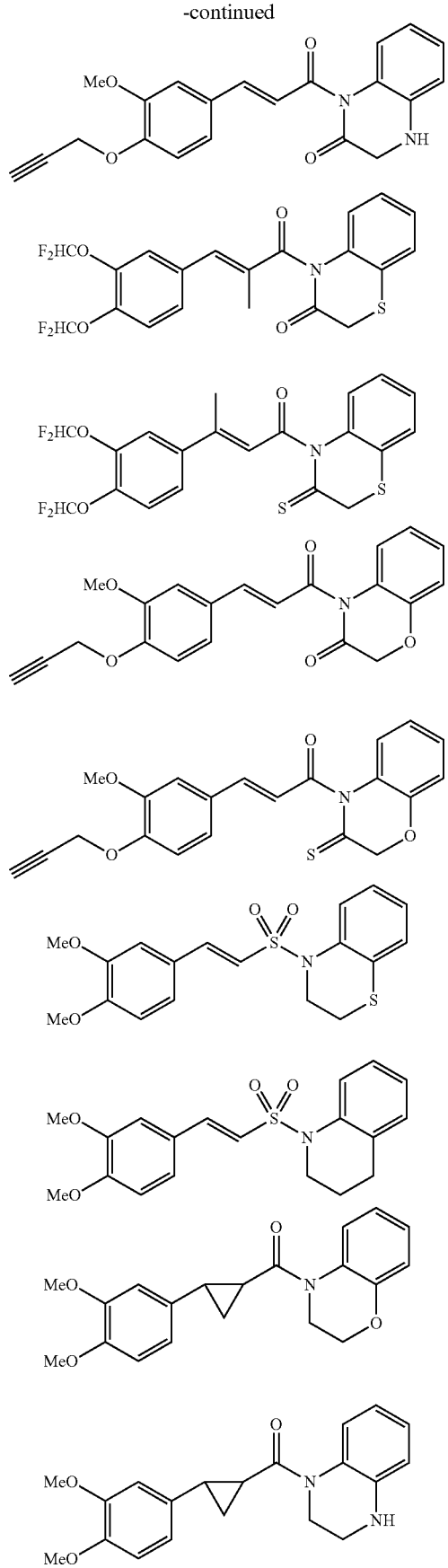

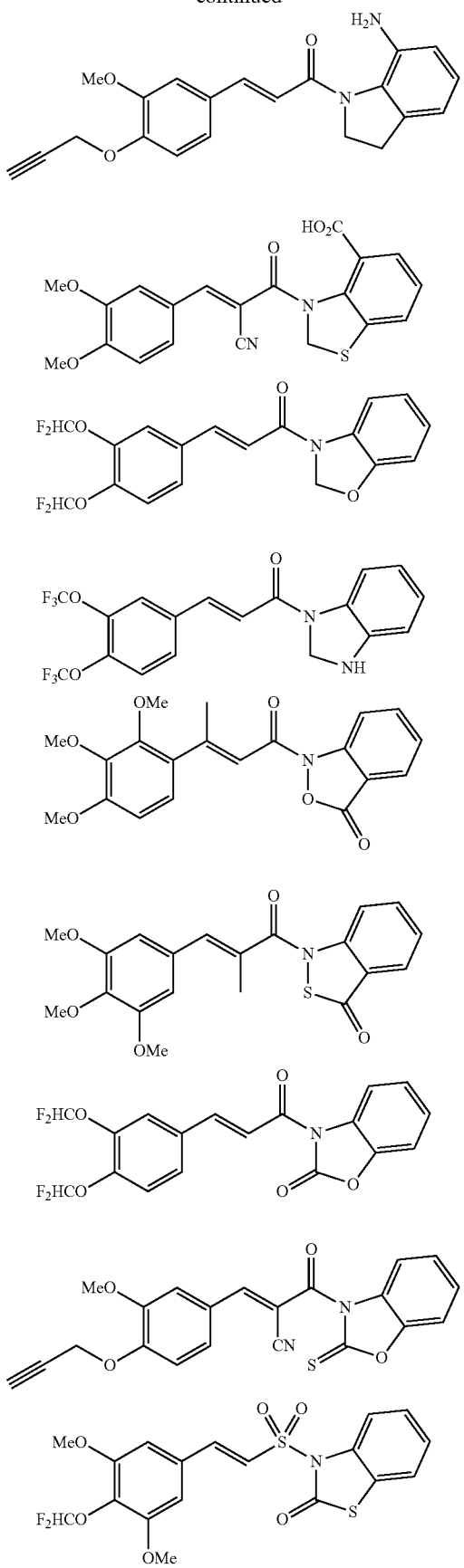
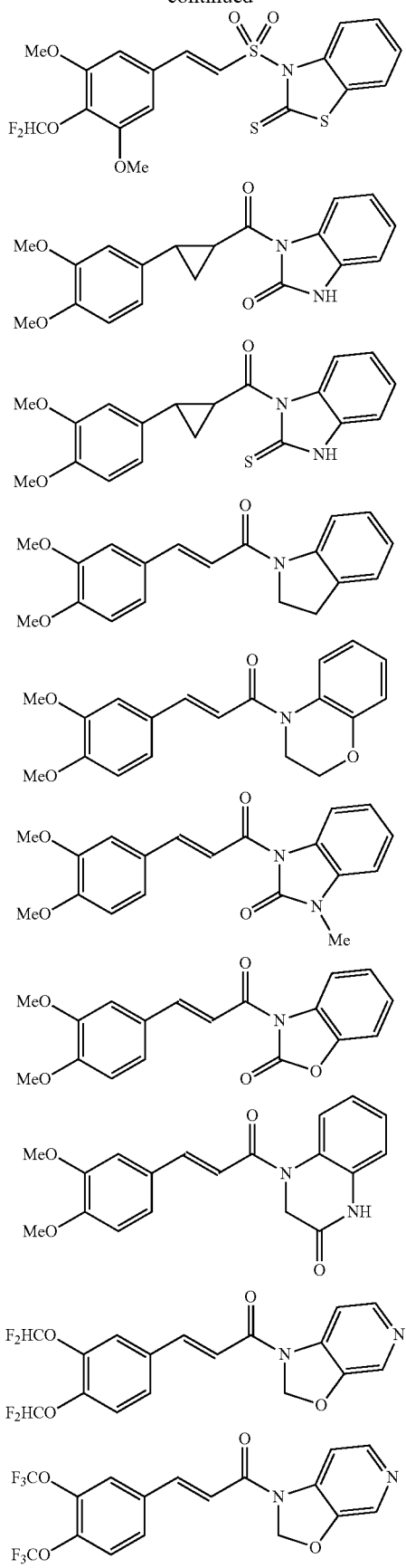

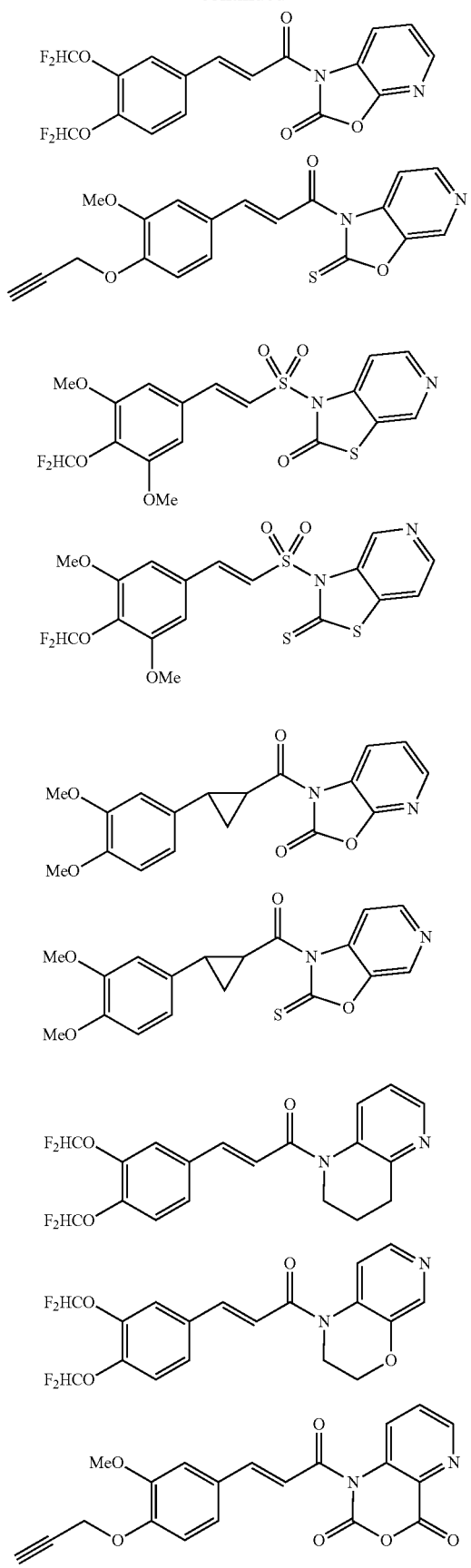
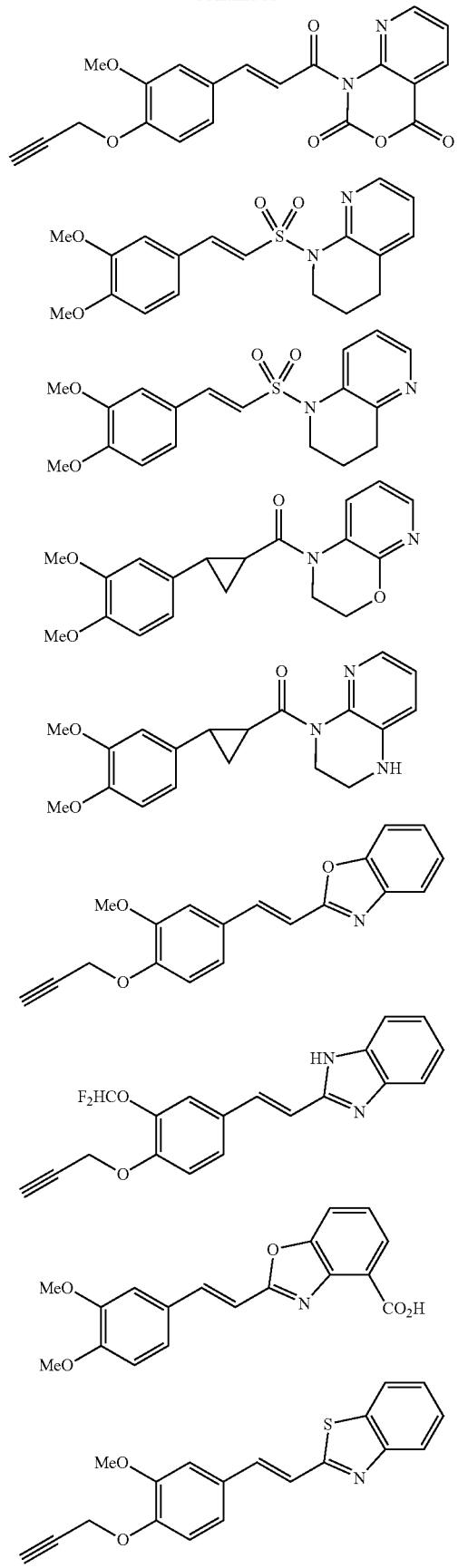

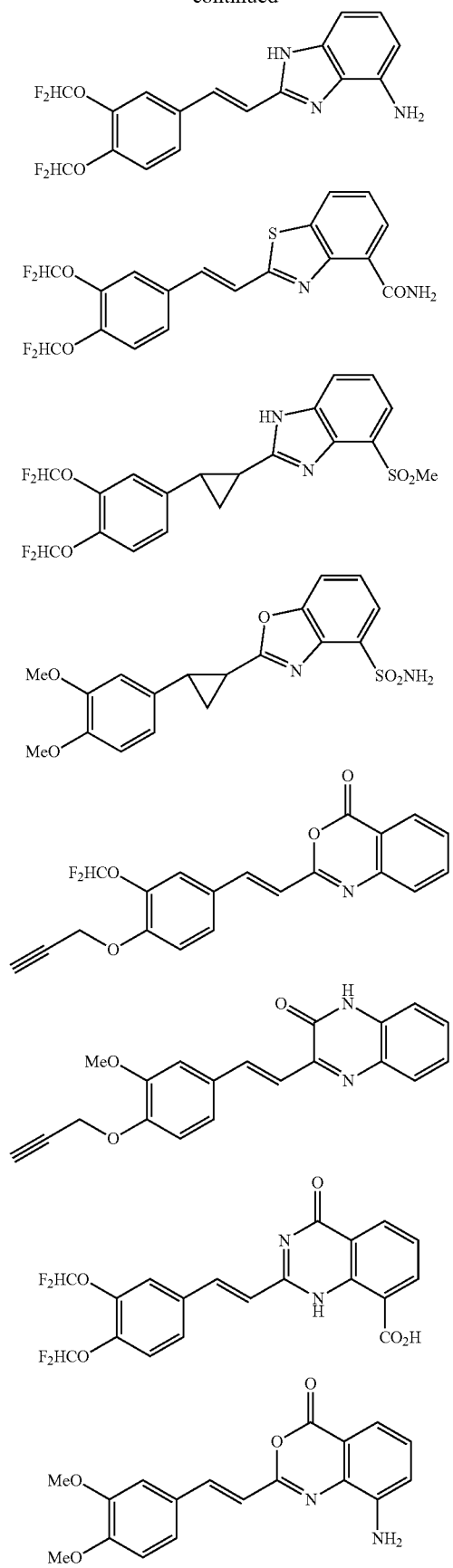
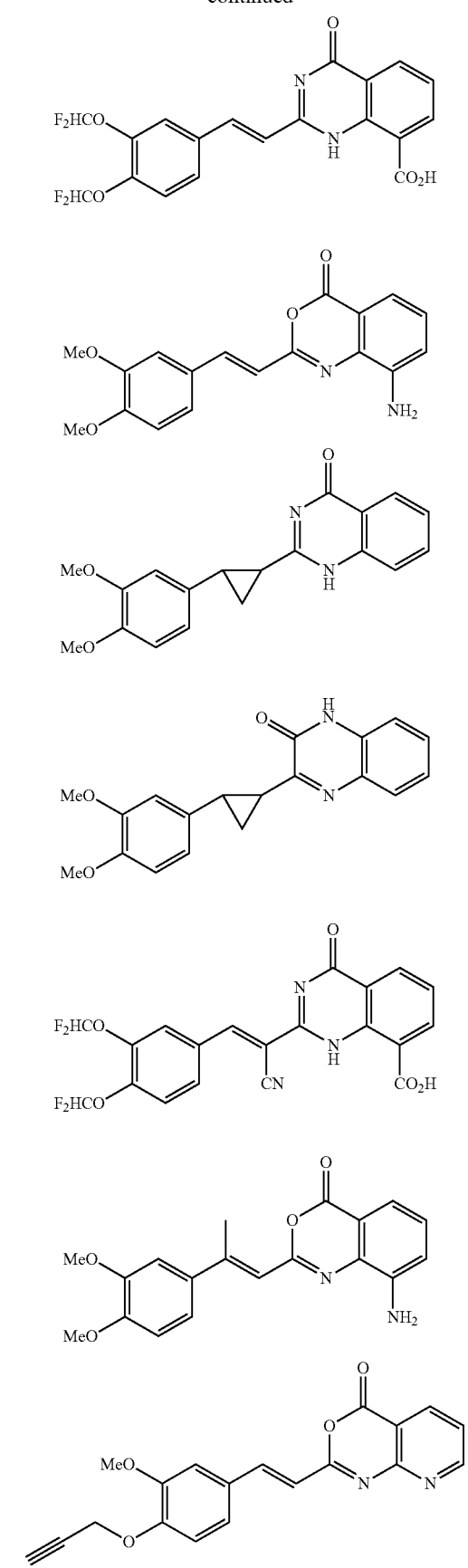

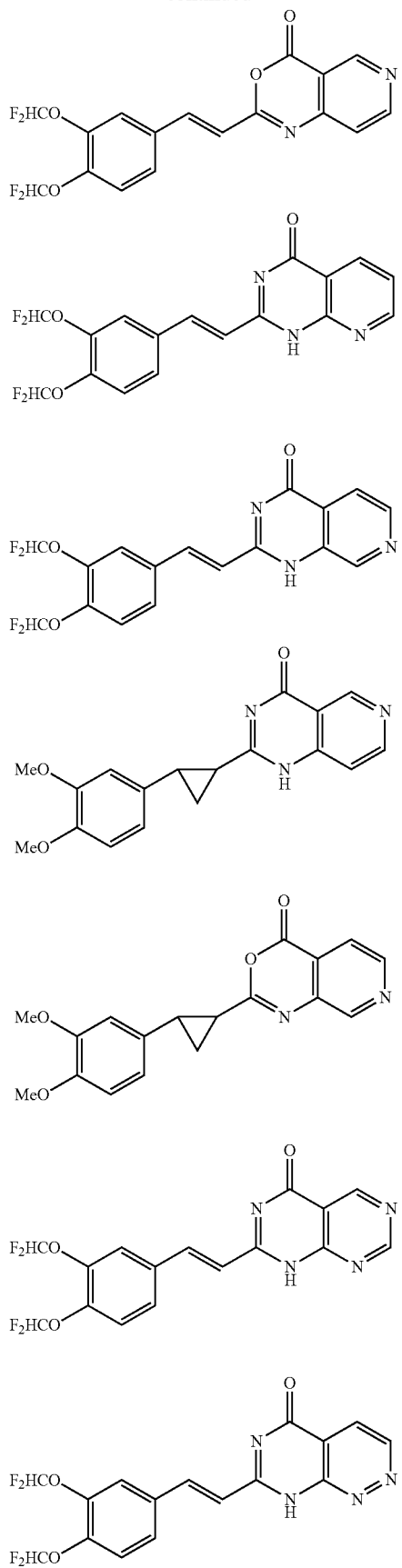
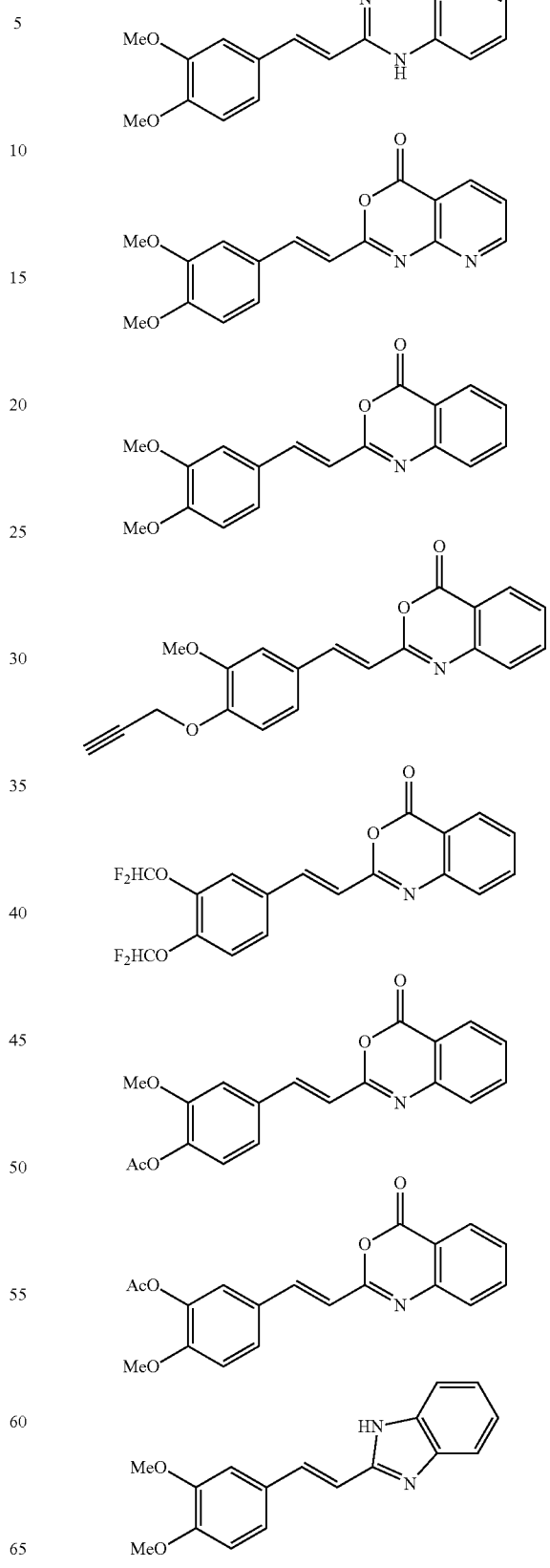
or a pharmaceutically acceptable salt or prodrug thereof.

It will be evident from the foregoing description that compounds of the present invention are fused ring analogues of tranilast (2-{[(2E)-3-(3,4-dimethoxyphenyl)prop-2-enoyl]amino}benzoic acid). As such, the compounds of the invention may have the ability to inhibit ERK phosphorylation and, therefore, act as an antifibrotic agent when administered to a subject. However, the compounds of the present invention are not limited to antifibrotic agents that act via inhibition of ERK phosphorylation and it is possible for them to have antifibrotic activity via a mechanism that does not involve inhibition of ERK phosphorylation.

Accordingly the compounds of the invention may find a multiple number of applications in which their ability to prevent, ameliorate or inhibit fibrosis can be utilised. For example compounds of Formulae (I), (II), (III) and (IV) may be used to treat a disease or condition associated with fibrosis or characterised by inflammation and/or a benign or malignant neoplastic disease.

The disease or condition associated with fibrosis may be selected from fibrotic skin disorders, such as keloids, hypertrophic scars and scleroderma; lung disease, such as pulmonary fibrosis; heart disease, such as heart failure due to ischaemic heart disease, valvular heart disease and hypertensive heart disease, diabetic cardiomyopathy and hypertension; and kidney disease, such as progressive kidney disease, cirrhosis of the liver, glomerulonephritis and diabetic nephropathy. In specific embodiments, the disease or condition is diabetic heart disease, diabetic kidney disease, or diabetic cardiomyopathy.

Diabetic cardiomyopathy refers to any one or more cardiac pathology and/or dysfunction in a subject, which is a complication of either Type I or Type II diabetes in the subject. The diabetes may be symptomatic or asymptomatic. Cardiac pathology which is characteristic of diabetic cardiomyopathy includes myocellular hypertrophy, myocardial fibrosis, and in some cases left ventricular hypertrophy. The pathologies which are contemplated arise independently from complications arising from coronary artery disease, although both diabetic complications and coronary artery complications may be present in the same subject. Diastolic dysfunction, such as an impairment in early diastolic filling, a prolongation of isovolumetric relaxation and increased atrial filling is also characteristic of diabetic cardiomyopathy, and may be identified using Doppler methods such as Doppler 2-dimensional echocardiography (for example Redford M M et al., JAMA (2003) 289:194-203) or radionuclide imaging for early or mild dysfunction and by standard echocardiograph testing for more severe dysfunction.

Cardiac fibrosis refers to the formation of fibrous tissue, including cellular and extracellular components, in the lining and muscle of the heart. If present in sufficient quantities, the fibrous tissue will result in a decrease in the contractility of one or more regions of the heart, resulting in functional deficit in cardiac output.

Alternatively, or in addition, it is also anticipated that the compounds will be useful in the treatment of a disease or condition characterised by inflammation and/or a benign or malignant neoplastic disease. The disease or condition characterised by inflammation may be selected from allergic rhinitis, bronchial asthma, rheumatoid arthritis, multiple sclerosis, type I and type II diabetes, systemic lupus, erythematosis, transplant rejection and inflammatory bowel disease. The benign or malignant neoplastic disease may be any such disease known to the skilled person.

The compounds may be used in the preparation of a medicament for treating a disease or condition associated with fibrosis. Alternatively, the compounds of the invention may be used in the preparation of a medicament for treating a disease or condition characterised by inflammation and/or a benign or malignant neoplastic disease.

Administration of compounds of Formulae (I), (II), (III) and (IV) to humans can be by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose.

In using the compounds they can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. See *Remingtons Pharmaceutical Sciences*, 19 edition, Mack Publishing Co. (1995) for further information.

The compounds can be administered alone or in the form of a pharmaceutical composition in combination with a pharmaceutically acceptable carrier, diluent or excipient. The compounds may be administered as the compounds themselves or in the form of their pharmaceutically acceptable salts or derivatives.

The compounds are, however, typically used in the form of pharmaceutical compositions which are formulated depending on the desired mode of administration. As such in a further embodiment the present invention provides a pharmaceutical composition including a compound of Formula (I), (II), (III) or (IV) and a pharmaceutically acceptable carrier, diluent or excipient. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found a container having a unit dosage of the agent(s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compounds may be used or administered in combination with one or more additional drug(s) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs, the compounds may be used in a combination therapy. When this is done the compounds are typically administered in combination with each other. Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical, compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilised, for example, by filtration through a bacterial-retaining filter, or by incorporating sterilising agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavouring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

The amount of compound administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular compound administered, the mode of administration, the bioavailability of the preparation administered, the dose regime selected, the use of other medications and other relevant circumstances.

A typical dosage will be a range from about 0.01 to 1000 mg per kilogram of body weight per day. Small doses (0.01-1 mg/kg per day) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. A more preferred dosage will be in the range from 0.1 to 300 mg per kilogram of body weight per day, more preferably from 0.1 to 100 mg per kilogram of body weight per day. A suitable dose can be administered in multiple sub-doses per day.

The compounds may be prepared using the reaction routes and synthesis schemes as described below, employing the techniques available in the art using starting materials that are commercially available or can be synthesised using known procedures or adaptations thereof. Whilst the preparation of particular compounds is outlined below, the skilled person will also recognise that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, 3$^{rd}$ Edition, John Wiley & Sons, 1991. Alternatively, other reactions disclosed herein or known in the art will be recognized as having applicability for preparing other compounds of the various embodiments.

Reagents useful for synthesizing compounds may be obtained or prepared according to techniques known in the art.

Compounds of Formula (I) may be synthesized by N-acylation of aminobenzenes to acid chlorides which can be derived from the carboxylic acid.

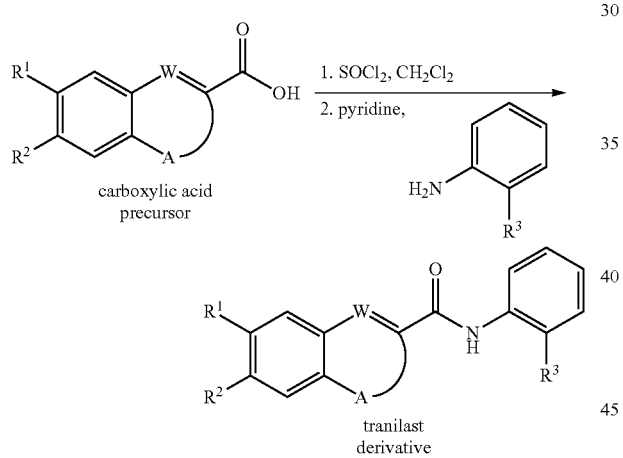

The route used to synthesise the carboxylic acid precursors will depend on whether the precursor is an O-, S-, C- or N-based derivative.

C-Based:

Carboxylic acid, ester and aldehyde precursor syntheses are shown below. The ester or aldehyde precursors produced can be readily converted to the corresponding carboxylic acid using standard hydrolysis or oxidation reactions, respectively.

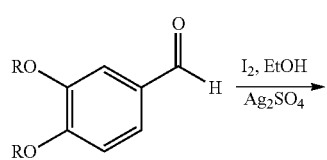

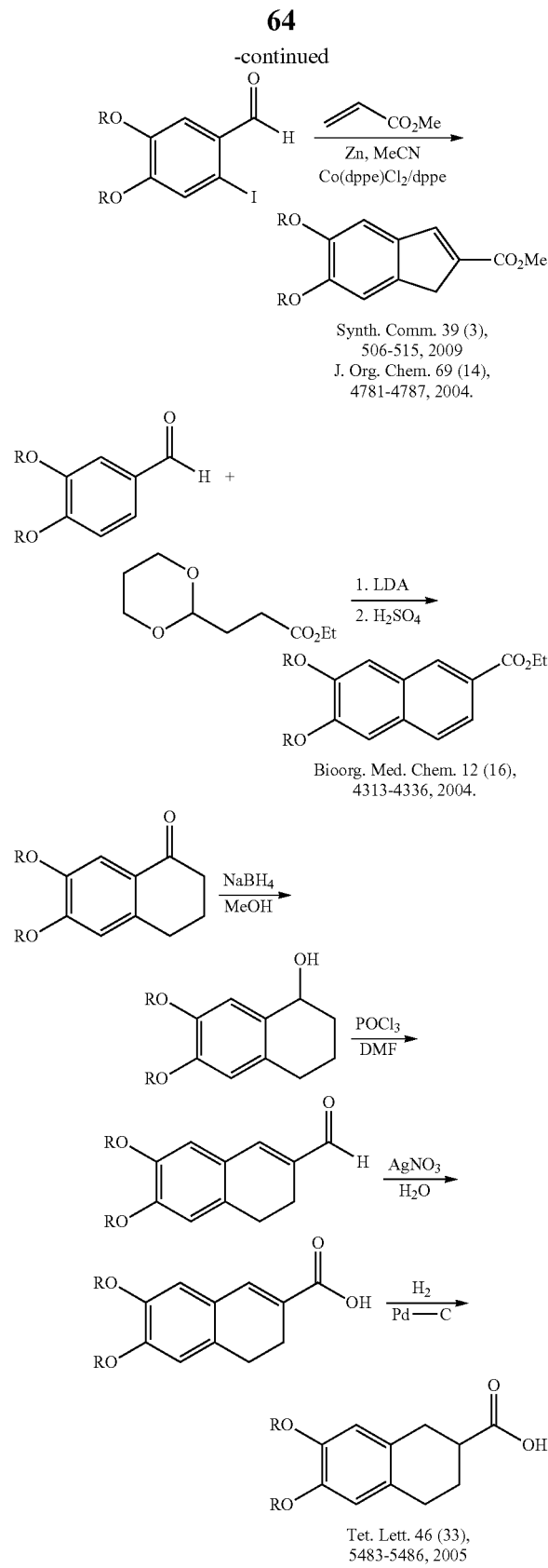

O-Based:

Carboxylic acid, ester and aldehyde precursor syntheses are shown below. The ester or aldehyde precursors produced can be readily converted to the corresponding carboxylic acid using standard hydrolysis or oxidation reactions, respectively.

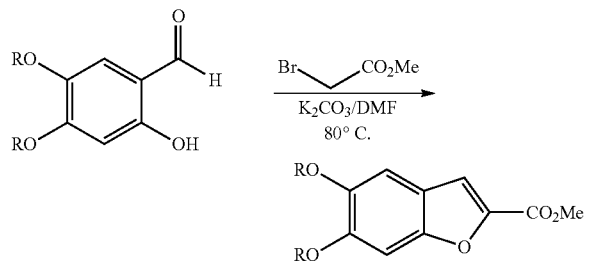

WO2007/118137 page 180
*Bioorg. Med. Chem. Lett.* 18 (20), 5591-5593, 2008.

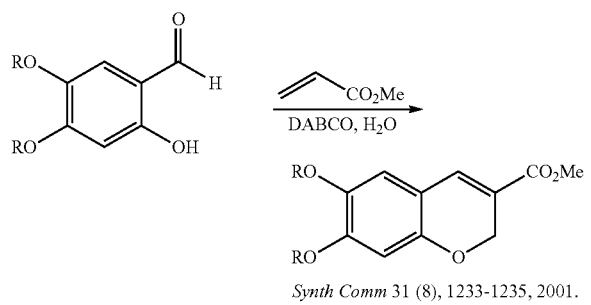

*Synth Comm* 31 (8), 1233-1235, 2001.

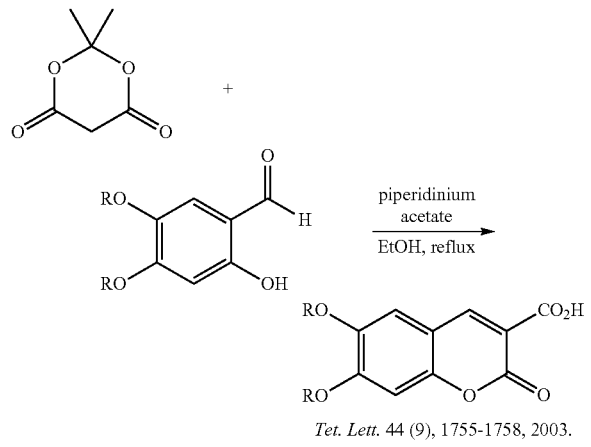

*Tet. Lett.* 44 (9), 1755-1758, 2003.

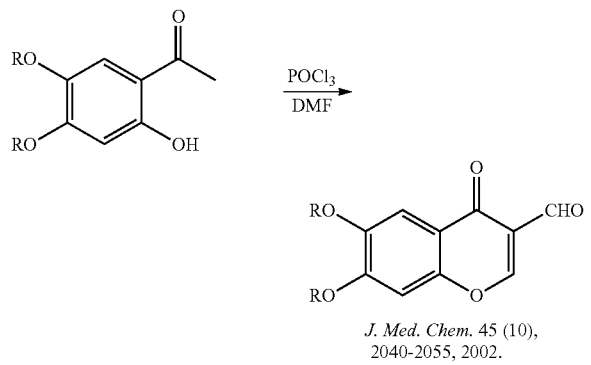

*J. Med. Chem.* 45 (10), 2040-2055, 2002.

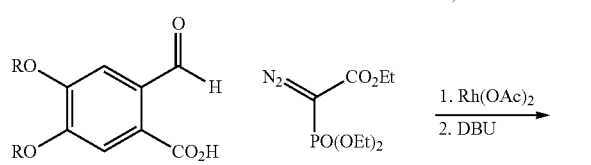

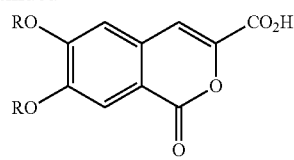

*Org Lett.* 4 (14), 2317-2320, 2002.

S-Based:

Ester syntheses are shown below. These methyl and ethyl ester precursors can be readily converted to the corresponding carboxylic acid in one step.

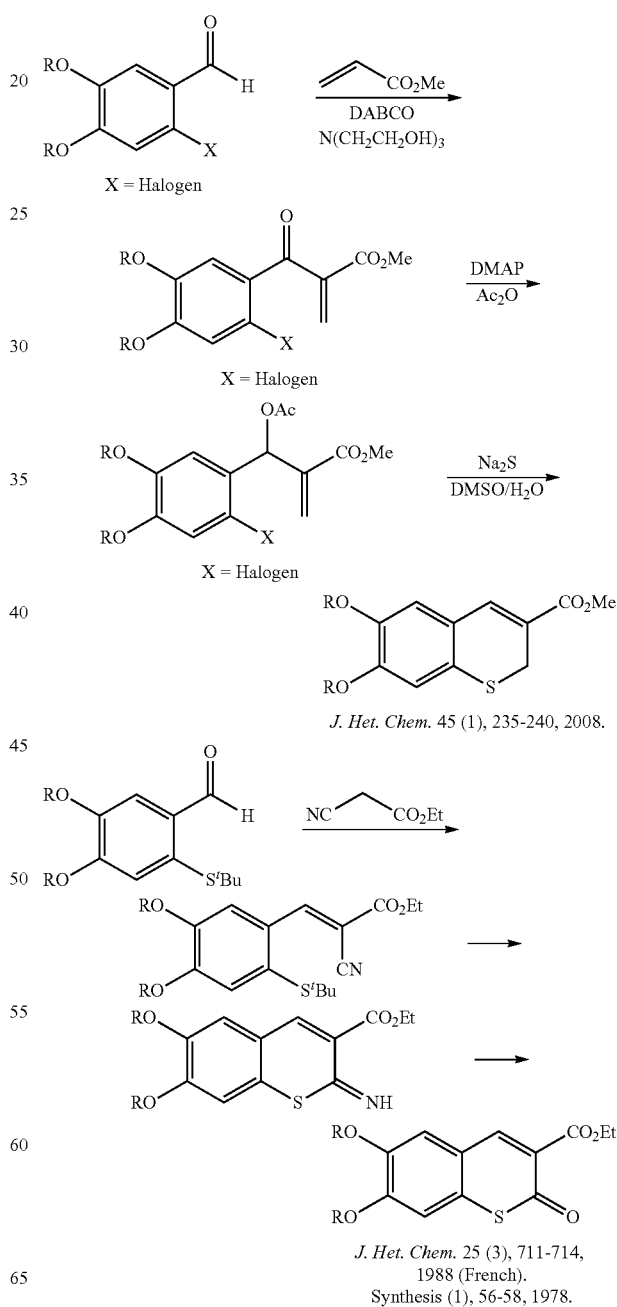

*J. Het. Chem.* 45 (1), 235-240, 2008.

*J. Het. Chem.* 25 (3), 711-714, 1988 (French).
*Synthesis* (1), 56-58, 1978.

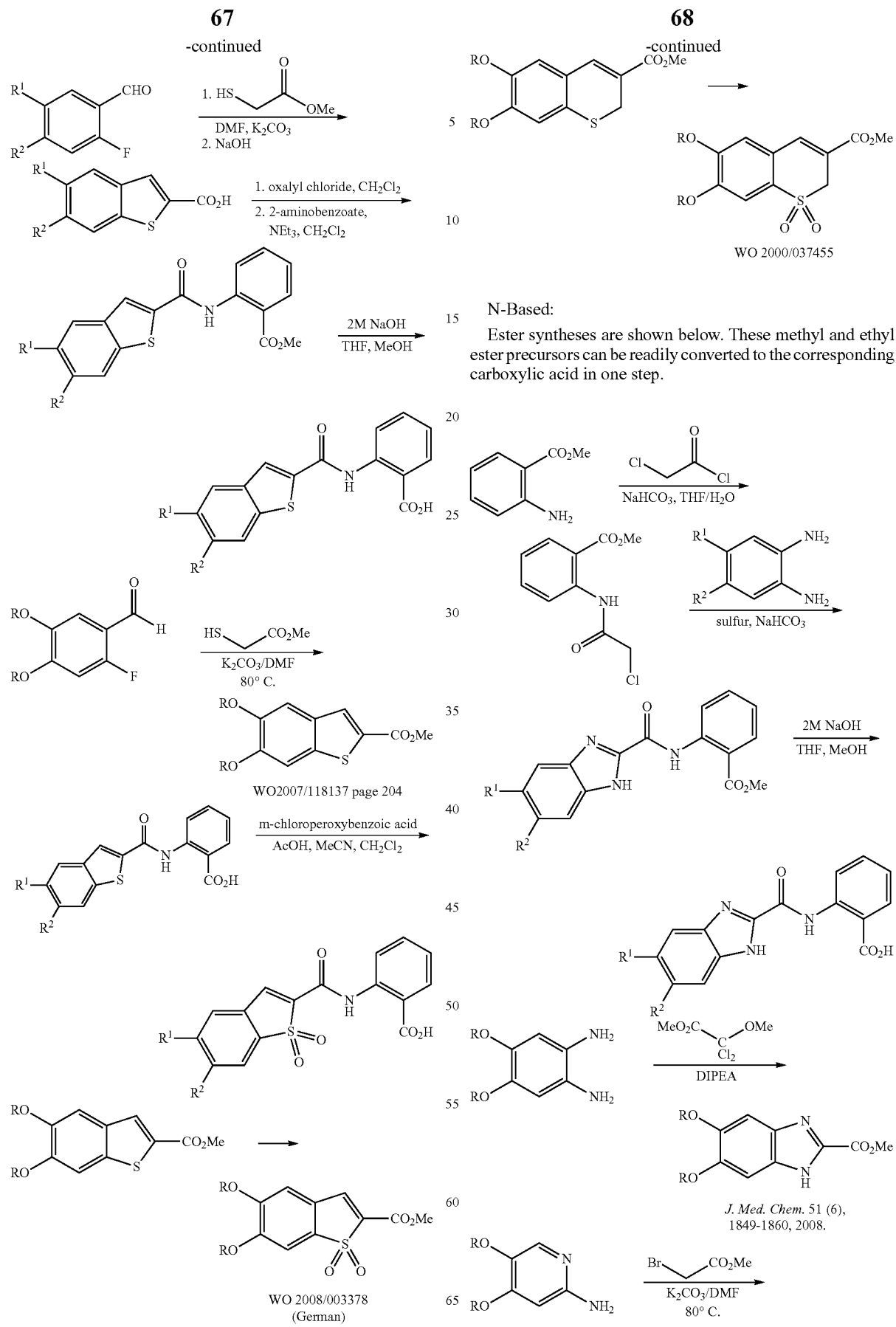
N-Based:
Ester syntheses are shown below. These methyl and ethyl ester precursors can be readily converted to the corresponding carboxylic acid in one step.

-continued
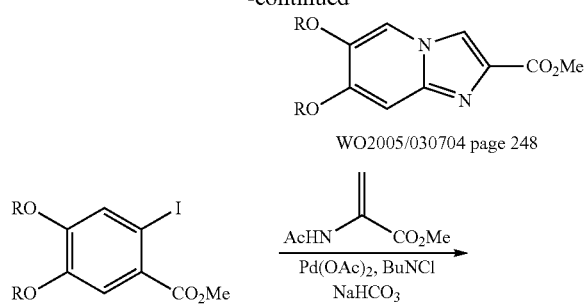
WO2005/030704 page 248
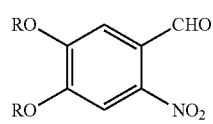
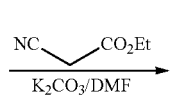
Tet. Lett. 48 (40), 713707139, 2007.
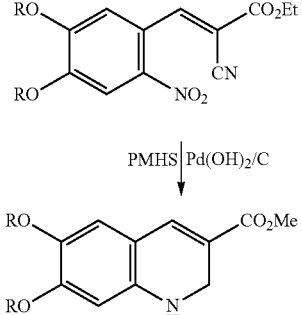
Tet. Lett. 48 (15), 2765-2768, 2007.
OBC 4 (21), 3960-3965, 2006.
Compounds of Formula (II) may be synthesized by N-acylation of aminobenzenes with acid chlorides which can be derived from the carboxylic acid.
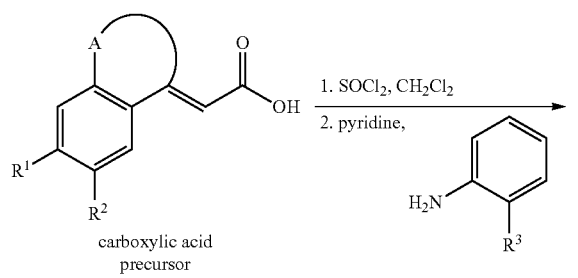
-continued
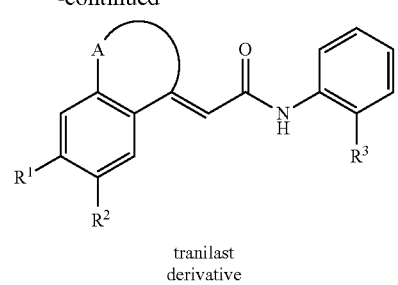
tranilast derivative
Synthetic schemes to synthesize 5,6-heterocyclic carboxylic acid precursors are shown below:
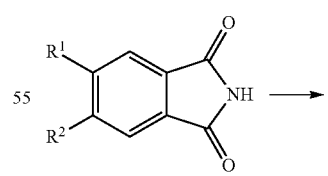
Perkin Transactions 1, 3073-3079, 2001.
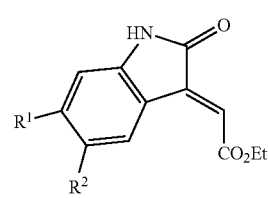
Letters in Organic Chemistry 4, 56-57, 2006.
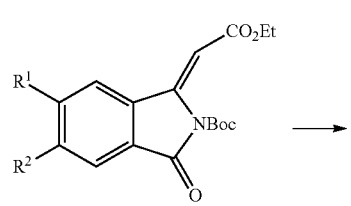

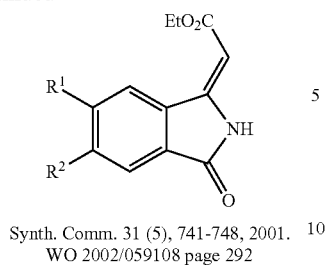
Synth. Comm. 31 (5), 741-748, 2001.
WO 2002/059108 page 292
Synthetic schemes to synthesize 6,6-heterocyclic carboxylic acid precursors are shown below:
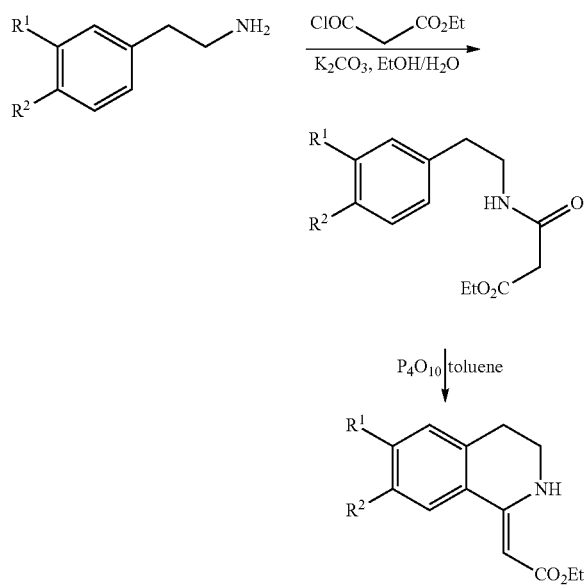
Chemistry: A European Journal
10(11),
2722-2731, 2004.
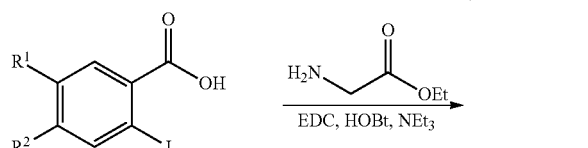
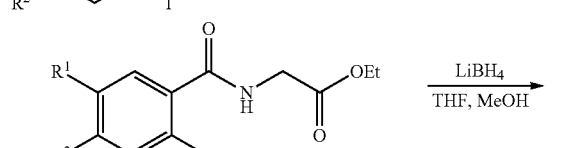
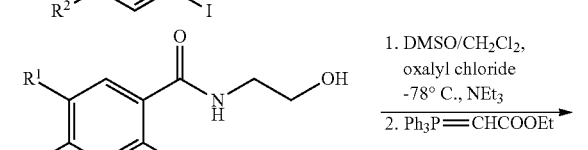
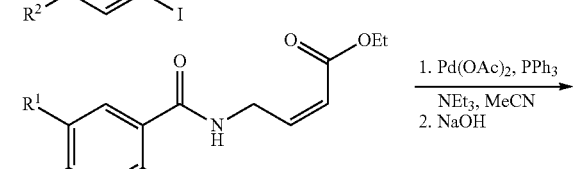
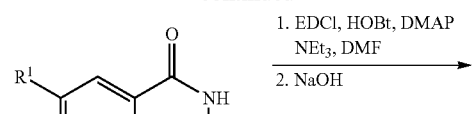
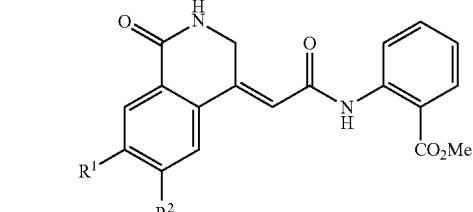
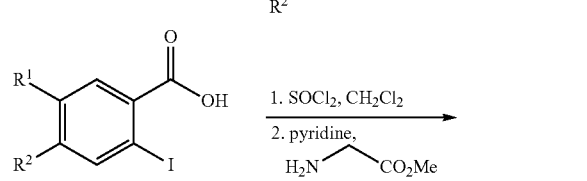
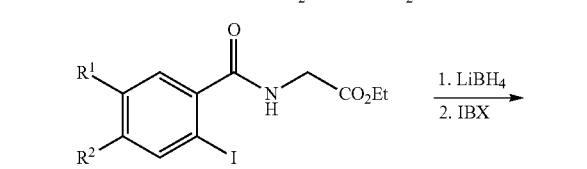
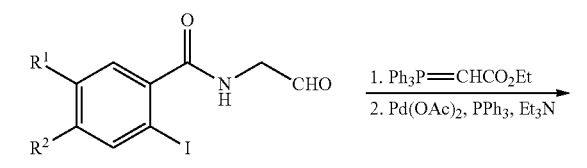
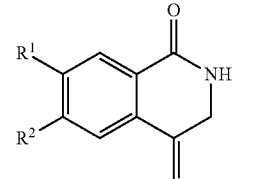
CemMedChem 1 (7),
710-714, 2006.
Compounds of Formula (III) may be synthesized by N-acylation of commercially available aryl amines/amides to the corresponding cinnamoyl chloride, derived from the cinnamic acid:
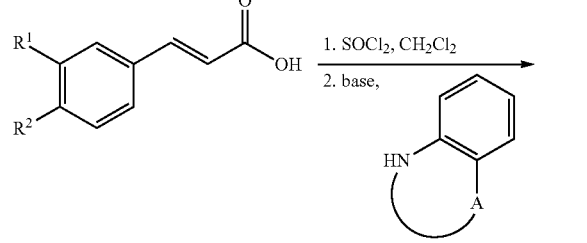

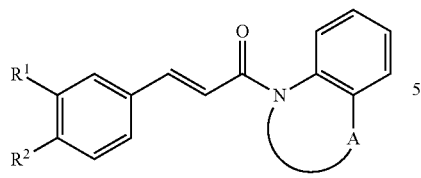
A list of commercially available precursors and their corresponding CAS numbers is shown below. Each of these can be N-acylated by reacting with a corresponding cinnamoyl chloride.
31499-90-8
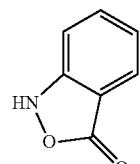
40352-87-2
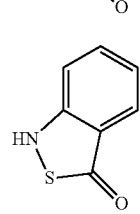
4746-67-2
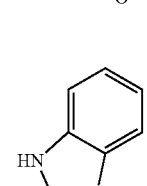
5698-74-8
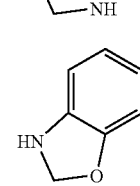
556834-27-6
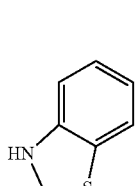
496-15-1
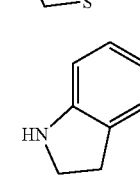
59-49-4
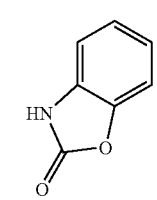
934-34-9
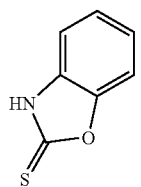
615-16-7
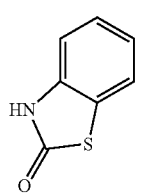
149-30-4
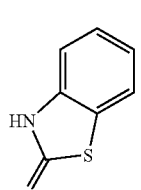
2382-96-9
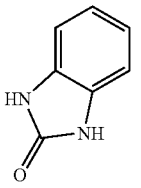
583-39-1
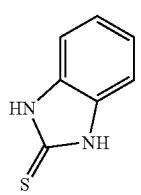
4295-36-7
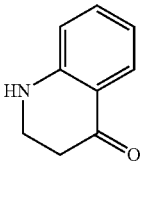
529-37-3
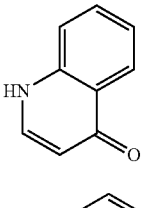
118-48-9
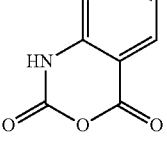

-continued
491-36-1
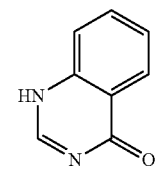
59564-59-9
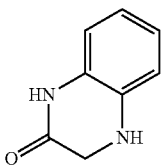
5466-88-6
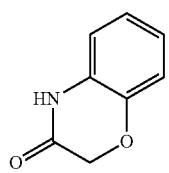
14183-51-8
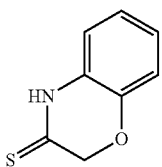
3597-63-5
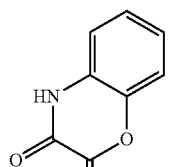
5325-20-2
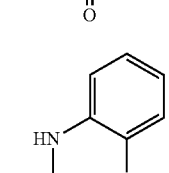
22191-30-6
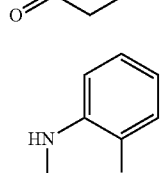
5735-53-7
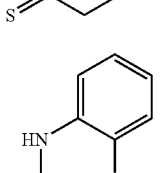
3080-99-7
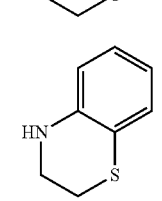
-continued
635-46-1
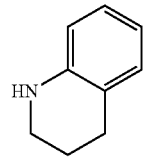
3476-89-9
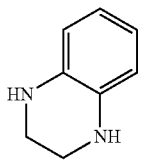
Compounds of Formula (IV) may be synthesized by condensing 3-methyl-1H-quinoxalin-2-one, 2-methyl-4H-3,1-benzoxazin-4-one or, 2-methyl-3H-quinazolin-4-one with a substituted benzaldehyde to provide fused heterocyclic tranilast derivatives. The intermediates can also be synthesized as shown below:
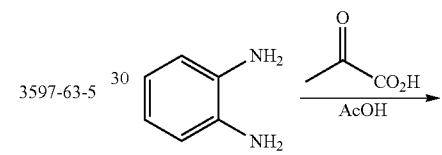
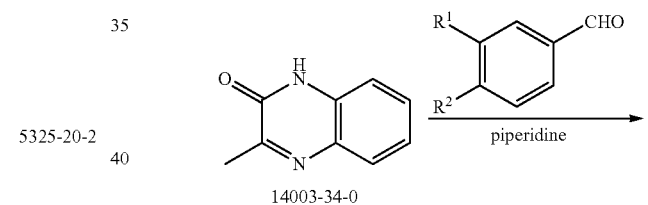
14003-34-0
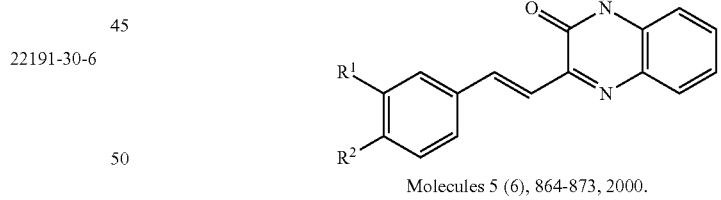
Molecules 5 (6), 864-873, 2000.
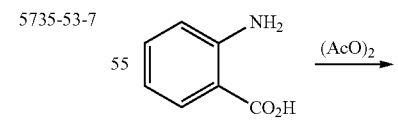
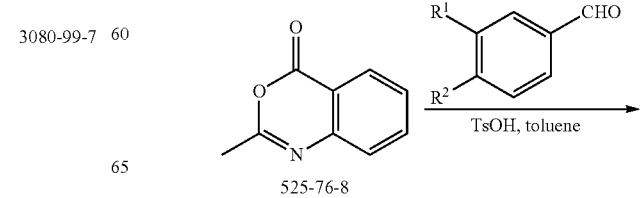
525-76-8

77

-continued

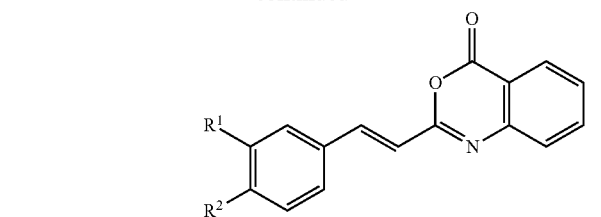

Journal of Agricultural and
Food Chemistry 51 (3),
594-600, 2003.

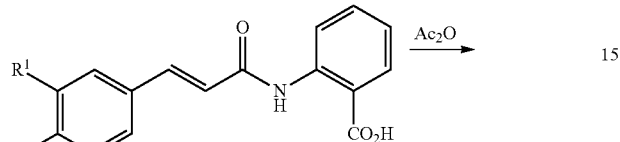

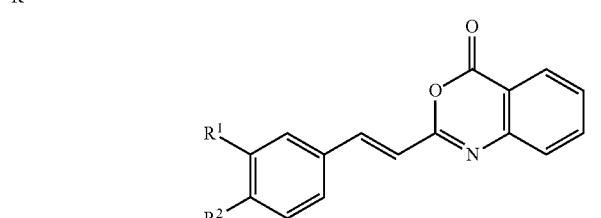

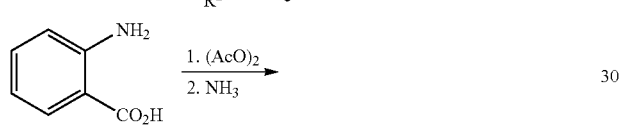

1769-24-0

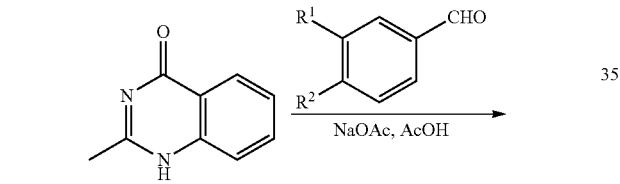

Bioorg Med Chem 17 (1),
119-132, 2009.
Acta Poloniae Pharmaceutica 60 (4),
275-279, 2003.

Substituted benzoxazoles, benzothiazoles, and benzimidazoles can be obtained by reaction of aldehydes with 2-aminophenol, 2-aminothiophenol and o-phenylenediamine, with 4-methoxy-TEMPO radical as the catalyst:

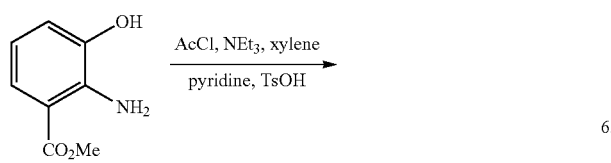

78

-continued

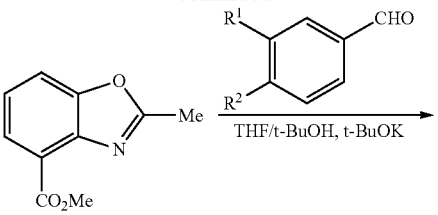

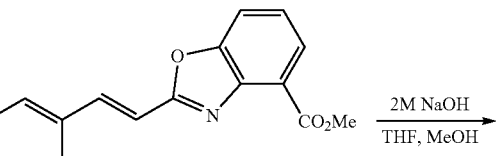

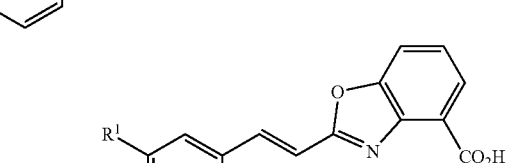

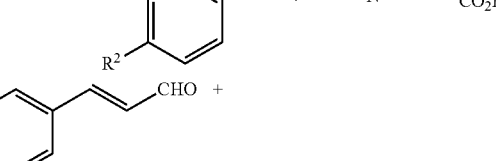

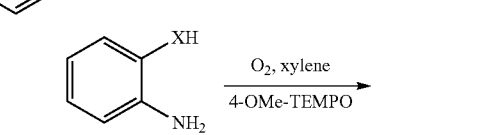

X = O, S, NH

Ang Chem Int Ed 47 (48),
9330-9333, 2008.

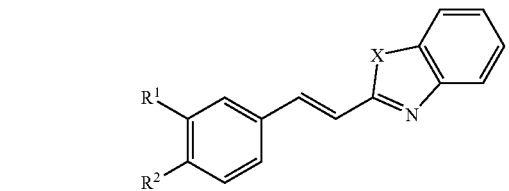

X = O, S, NH

The compounds of Formulae (I) to (IV) and intermediates in their synthesis can be isolated from a reaction mixture using standard work-up and purification procedures. Suitable procedures include solvent extraction, chromatography (thin or thick layer chromatography, HPLC, flash chromatography, MPLC, etc.), recrystallisation etc.

The present invention includes salts of the compounds of Formulae (I) to (IV). The salts may serve as intermediates in the purification of compounds or in the preparation of other, for example pharmaceutically acceptable, acid addition salts, or they may be useful for identification, characterisation or purification. The salts can exist in conjunction with the acidic or basic portion of the molecule and can exist as acid addition, primary, secondary, tertiary, or quaternary ammonium, alkali metal, or alkaline earth metal salts. Generally, acid addition salts are prepared by the reaction of an acid with compounds of Formulae (I) to (IV). The alkali metal and alkaline earth metal salts are generally prepared by the reaction of the hydroxide form of the desired metal salt with compounds of Formulae (I) to (IV).

Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, or naphthalene-2-sulphonic acid.

The present invention also includes esters of the compounds of Formulae (I) to (IV), such esters being for example aliphatic esters such as alkyl esters. The esters of the compounds of Formulae (I) to (IV) may be pharmaceutically acceptable metabolically labile esters. These are ester derivatives of compounds of Formulae (I) to (IV) that are hydrolysed in vivo to afford the compound of Formulae (I) to (IV) and a pharmaceutically acceptable alcohol. Examples of metabolically labile esters include esters formed with alkanols in which the alkanol moiety may be optionally substituted by an alkoxy group, for example methanol, ethanol, propanol and methoxyethanol.

The compounds of the various embodiments may be prepared using the reaction routes and synthesis schemes as described above, employing the techniques available in the art using starting materials that are readily available. The person skilled in the art will recognise that the chemical reactions described may be readily adapted to prepare a number of other compounds. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, 3$^{rd}$ Edition, John Wiley & Sons, 1991. Reagents useful for synthesizing compounds may be obtained or prepared according to techniques known in the art.

The anti-fibrotic effects of compounds of Formulae (I) to (IV) can be tested using any of the following methods:
  (i) In a renal cell line by measuring proline incorporation after transforming growth factor-β stimulation;
  (ii) Matrix synthesis may be stimulated by platelet derived growth factor (PDGF). Accordingly, mesangial cells incubated with PDGF can be used to demonstrate proline incorporation, which is an indicator of matrix synthesis and thereby a model for fibrosis; or
  (iii) Matrix synthesis may be stimulated by both angiotensin II or transforming growth factor beta (TGF-β). Accordingly, neonatal cardiac fibroblasts incubated with angiotensin II or TGF-β can be used to demonstrate proline incorporation, which is an indicator of matrix synthesis and thereby a model for fibrosis.

Figure 1:
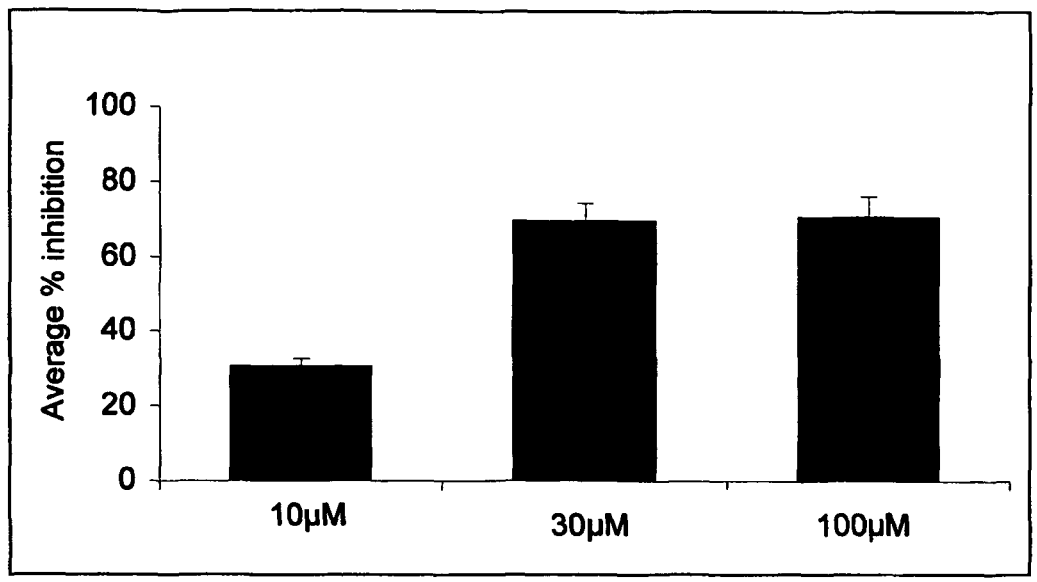
FIG. 1: Average % inhibition of TGF-β stimulated proline incorporation by compound FT98 at 10 μM, 30 μM and 100 μM (SEM).
Figure 2:
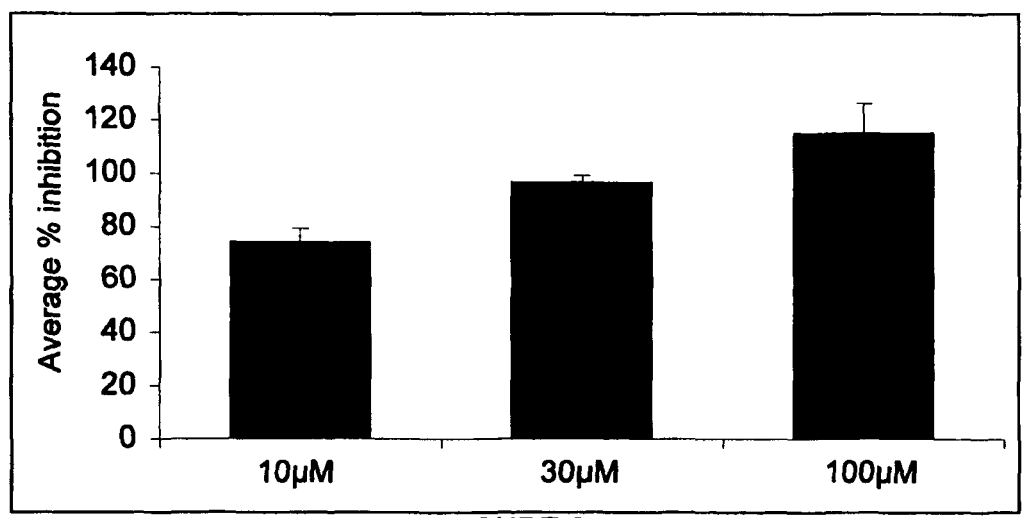
FIG. 2: Average % inhibition of TGF-β stimulated proline incorporation by compound FT108 at 10 μM, 30 μM and 100 μM (SEM).
Figure 3:
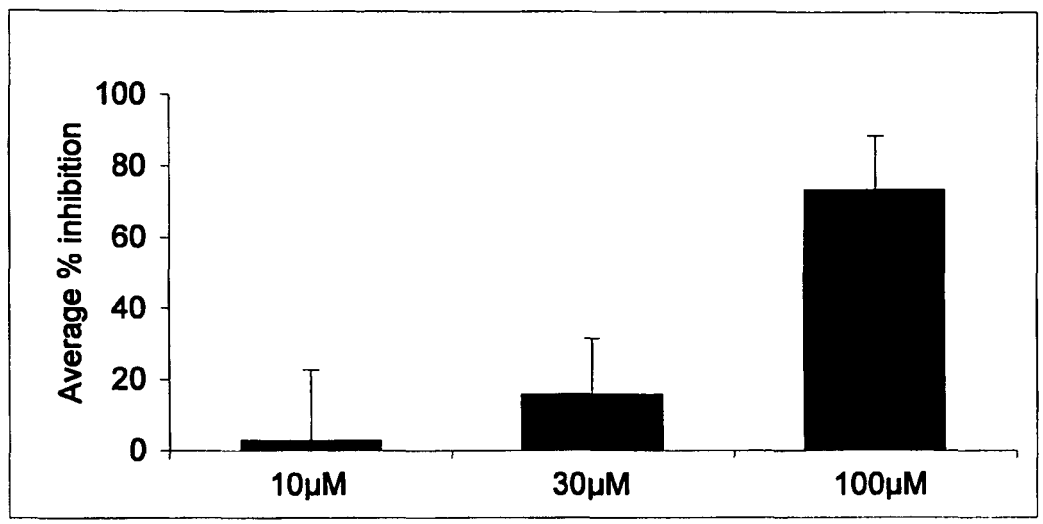
FIG. 3: Average % inhibition of TGF-β stimulated proline incorporation by compound FT109 at 10 μM, 30 μM and 100 μM (SEM).
Figure 4:
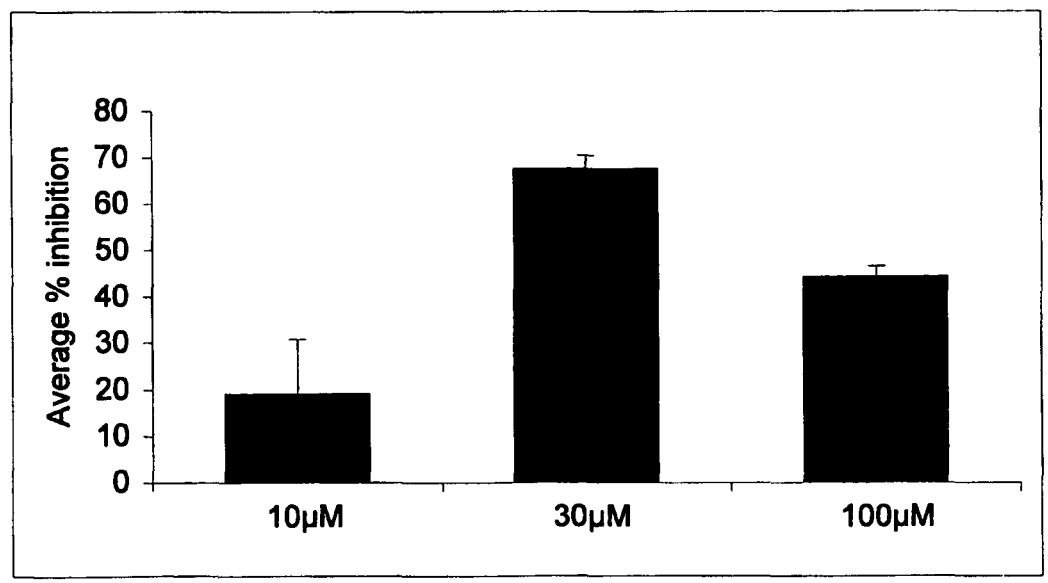
FIG. 4: Average % inhibition of TGF-β stimulated proline incorporation by compound FT113 at 10 μM, 30 μM and 100 μM (SEM).
Figure 5:
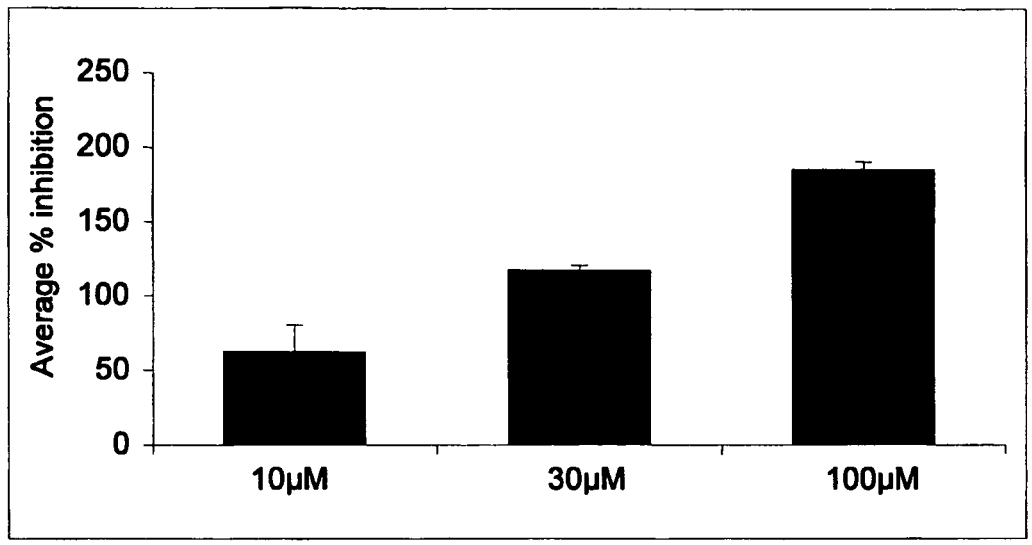
FIG. 5: Average % inhibition of TGF-β stimulated proline incorporation by compound FT121 at 10 μM, 30 μM and 100 μM (SEM).
Figure 6:
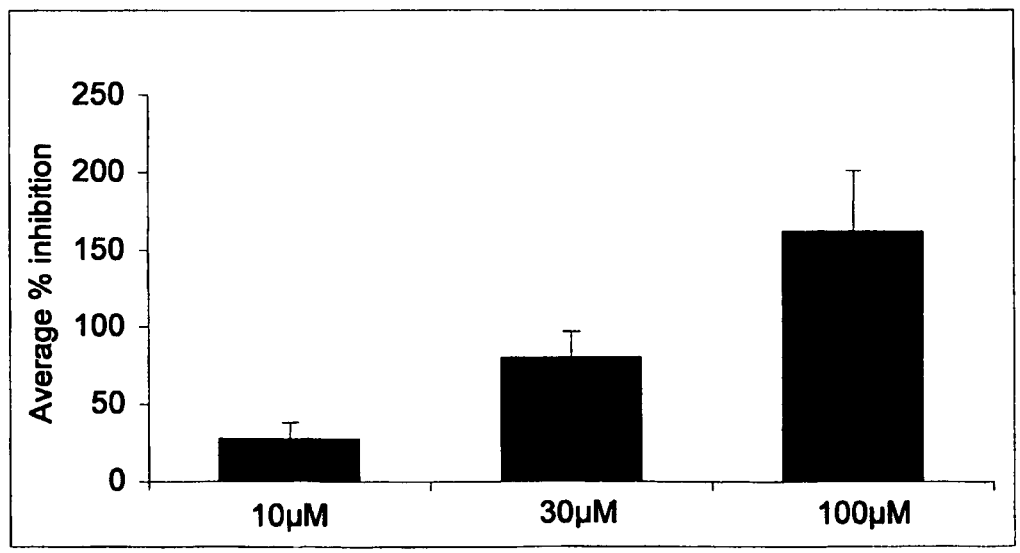
FIG. 6: Average % inhibition of TGF-β stimulated proline incorporation by compound FT122 at 10 μM, 30 μM and 100 μM (SEM).
Figure 7:
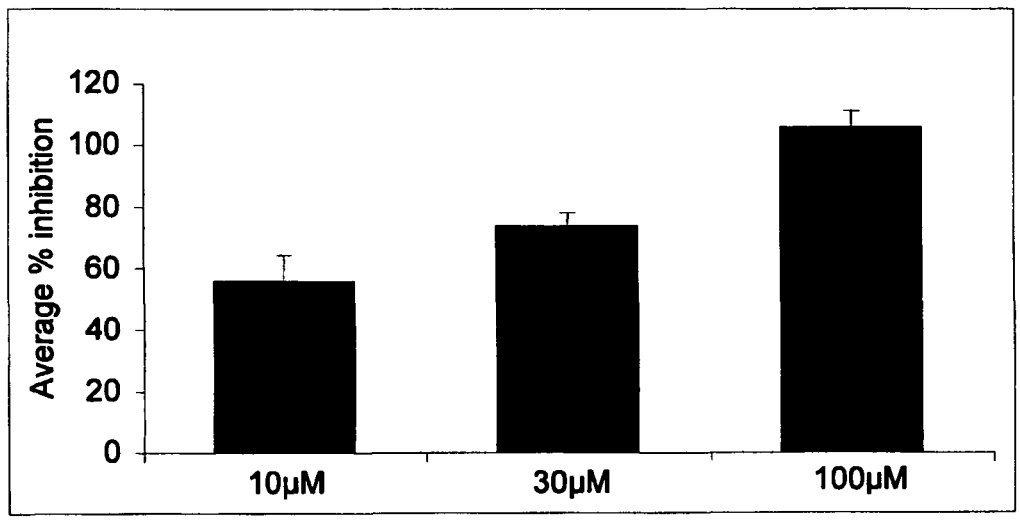
FIG. 7: Average % inhibition of TGF-β stimulated proline incorporation by compound FT126 at 10 μM, 30 μM and 100 μM (SEM).
Figure 8:
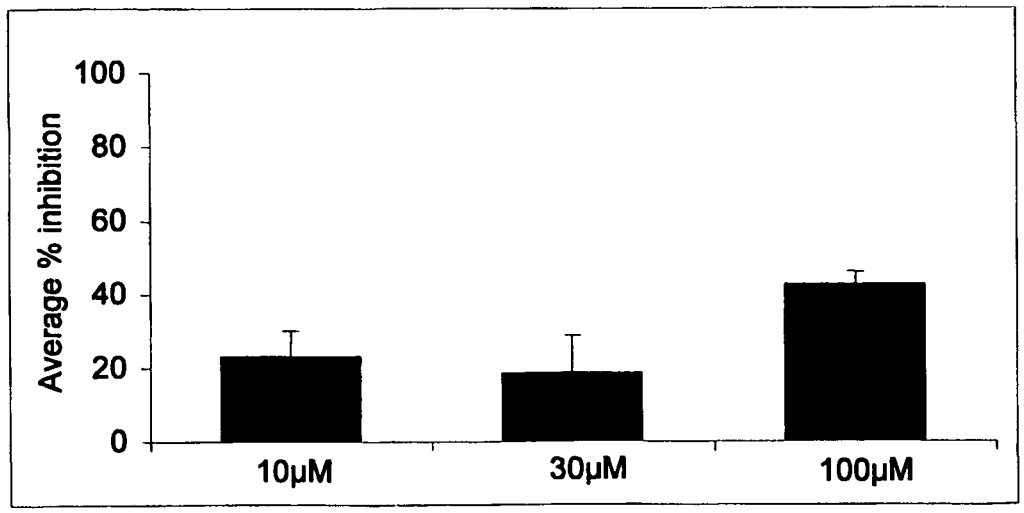
FIG. 8: Average % inhibition of TGF-β stimulated proline incorporation by compound FT128 at 10 μM, 30 μM and 100 μM (SEM).
Figure 9:
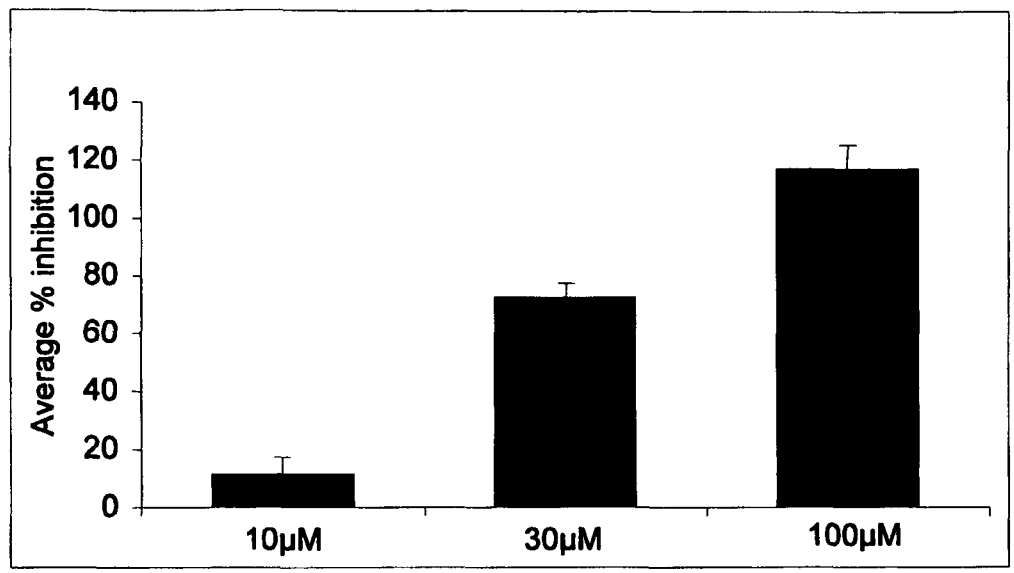
FIG. 9: Average % inhibition of TGF-β stimulated proline incorporation by compound FT129 at 10 μM, 30 μM and 100 μM (SEM).
Figure 10:
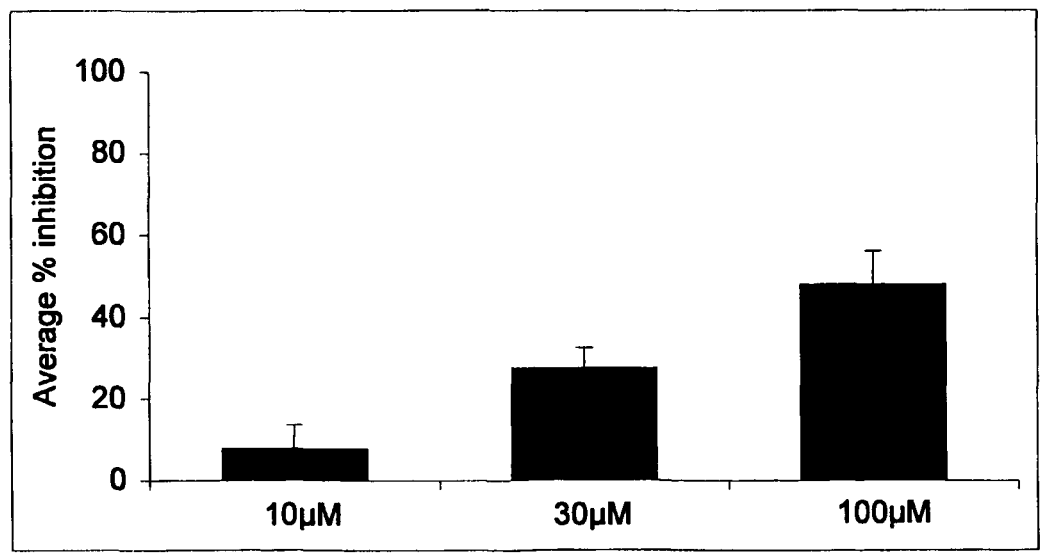
FIG. 10: Average % inhibition of TGF-β stimulated proline incorporation by compound FT130 at 10 μM, 30 μM and 100 μM (SEM).
Figure 11:
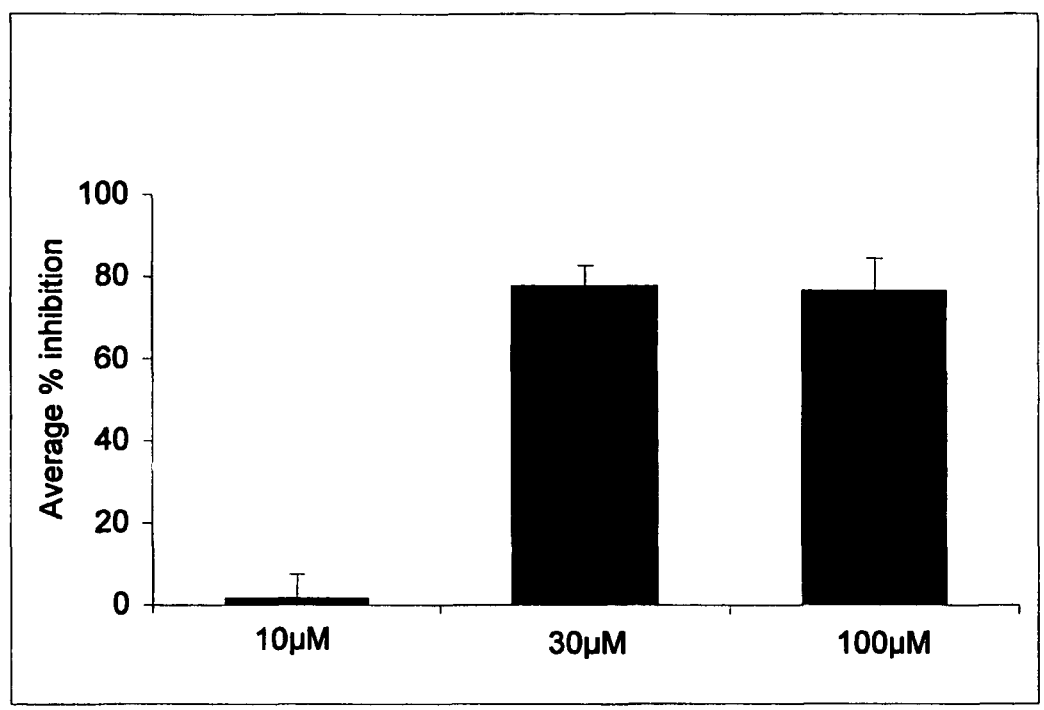
FIG. 11: Average % inhibition of TGF-β stimulated proline incorporation by compound FT132 at 10 μM, 30 μM and 100 μM (SEM).

An average % inhibition of greater than 100% indicates cell stress or death in FIGS. 5, 6 and 9.

Examples of materials and methods for use with the compounds of the present invention will now be provided. In providing these examples, it is to be understood that the specific nature of the following description is not to limit the generality of the above description.

EXAMPLES

Experimental

Electrospray ionization (ESI) high resolution mass spectra (HRMS) were obtained on a Finnigan hybrid LTQ-FT mass spectrometer (Thermo Electron Corp.). Proton nuclear magnetic resonance ($^1$H NMR) and proton decoupled carbon nuclear magnetic resonance ($^{13}$C NMR) spectra were obtained on Unity 400, Innova 400 or Innova 500 instruments (Melbourne, Australia) operating at 400 or 500 MHz for $^1$H and at 100 or 125 MHz for $^{13}$C. All signals were referenced to solvent peaks (CDCl$_3$: 7.26 ppm for $^1$H and 77.0 ppm for $^{13}$C; DMSO-d$_6$: 2.49 ppm for $^1$H and 39.5 ppm for $^{13}$C). Infrared (IR) spectra were obtained using a PerkinElmer Spectrum One FT-IR spectrometer with zinc selenide/diamond Universal ATR Sampling Accessory. Melting points were obtained using a Reichert-Jung hot stage apparatus and are corrected. Analytical thin layer chromatography (TLC) was conducted on 2 mm thick silica gel GF$_{254}$. Compounds were visualised with solutions of 20% w/w phosphomolybdic acid in ethanol, 20% w/w potassium permanganate in water or under UV (365 nm). Flash chromatography was performed with Merck Silica Gel 60. Petrol refers to the fraction boiling at 40-60° C. All other reagents were used as received.

Synthesis of Compounds of Formulae (I) to (IV)

(E)-3-[2-(3,4-Dimethoxyphenyl)ethenyl]-4H-1,2,4-benzothiadiazine-1,1-dioxide (FT98)

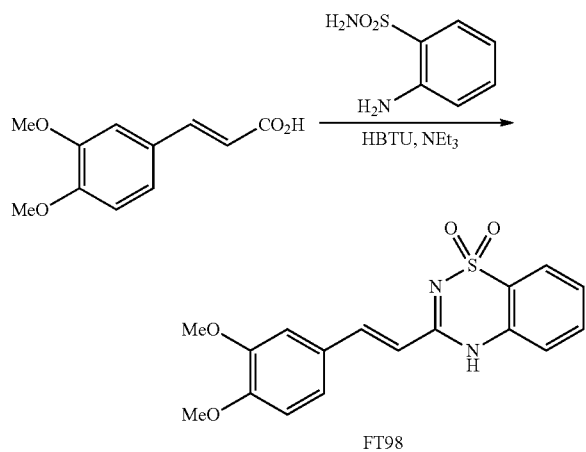

2-Aminobenzenesulfonamide (0.25 g, 1.4 mmol) was added to a suspension of (E)-3-(3,4-dimethoxyphenyl)acrylic acid (0.25 g, 1.2 mmol), HBTU (0.55 g, 1.4 mmol) and NEt$_3$ (0.67 mL, 4.8 mmol) in MeCN (5 mL) and the reaction was stirred at rt for 16 h. Extra NEt$_3$ (0.67 mL, 4.8 mmol) in MeCN (5 mL) was added and the reaction was stirred at rt for 64 h. The solution was acidified and the precipitate was collected by filtration. Hot EtOH (15 mL) was added to the crude product and the undissolved solid was collected by hot filtration, providing (E)-3-[2-(3,4-dimethoxyphenyl)ethenyl]-4H-1,2,4-benzothiadiazine-1,1-dioxide (58 mg, 14%) as a colourless crystalline solid; mp 276-279° C.; $\delta_H$ (500 MHz, DMSO-d$_6$) 3.81 (s, 3H, OCH$_3$), 3.83 (s, 3H, OCH$_3$), 6.75 (d, J=15.6 Hz, 1H, CH=CHCO), 7.05 (d, J$_{5',6'}$=8.0 Hz, 1H, H5'), 7.29 (d, J$_{5',6'}$=8.0 Hz, 1H, H6'), 7.31 (s, 1H, H2'), 7.38 (d, J$_{5,6}$=8.0 Hz, 1H, H5), 7.45 (t, J$_{5,6}$=J$_{6,7}$=8.0 Hz, 1H, H6), 7.68 (t, J$_{6,7}$=J$_{7,8}$=8.0 Hz, 1H, H7), 7.80 (d, J$_{7,8}$=8.0 Hz, 1H, H8), 7.82 (d, J=15.6 Hz, 1H, CH=CHCO), 12.13 (s, 1H, NH); $\delta_C$ (125 MHz, DMSO-d$_6$) 55.4, 55.6, 110.3, 111.8, 116.6, 117.6, 122.0, 122.7, 123.3, 126.3, 126.9, 133.0, 135.2, 142.2, 149.0, 151.1, 153.5; HRMS (ESI) calculated for C$_{17}$H$_{16}$N$_2$O$_4$S [M+H]$^+$ 345.0904, found 345.0900; $v_{max}$ 756, 1134, 1263, 1513, 1568, 1600, 3024, 3117, 3163, 3200 cm$^{-1}$.

(E)-2-(3,4-Dimethoxystyryl)-4H-pyrido[2,3-d][1,3]oxazin-4-one (FT102)

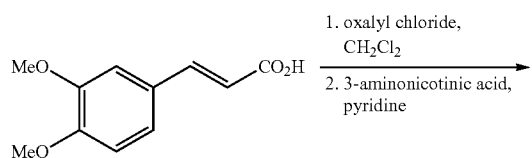

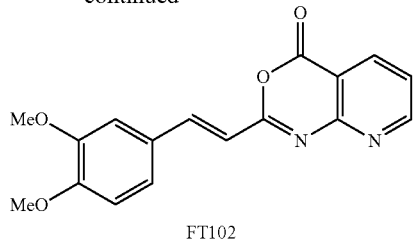

A suspension of (E)-3-(3,4-dimethoxyphenyl)acrylic acid (0.25 g, 1.2 mmol) in CH$_2$Cl$_2$ (5 mL) was treated with oxalyl chloride (0.41 mL, 4.8 mmol). The solution was stirred at it for 1 h and the solvent was removed under reduced pressure to give the acid chloride as a yellow solid. 3-Aminonicotinic acid (0.25 g, 1.4 mmol) was added to a solution of the acid chloride (1.2 mmol) in pyridine (2.0 mL) and the suspension was stirred at rt for 7 d. The solution was diluted with water and the precipitate was collected by filtration providing (E)-2-(3,4-dimethoxystyryl)-4H-pyrido[2,3-d][1,3]oxazin-4-one (0.16 g, 41%) as a green-yellow solid; mp 228-231° C.; $\delta_H$ (500 MHz, DMSO-d$_6$) 3.81 (s, 3H, OCH$_3$), 3.84 (s, 3H, OCH$_3$), 6.99 (d, J=16.5 Hz, 1H, CH=CHCO), 7.02 (d, J$_{4,5}$=8.0 Hz, 1H, H5'), 7.37 (d, J$_{5',6'}$=8.0 Hz, 1H, H6'), 7.49 (s, 1H, H2'), 7.55 (dd, J$_{4,5}$=8.0, J$_{5,6}$=4.0 Hz, 1H, H5), 7.82 (d, J=16.5 Hz, 1H, CH=CHCO), 7.47 (d, J$_{4,5}$=8.0 Hz, 1H, H4), 8.95 (d, J$_{5,6}$=4.0 Hz, 1H, H6); $\delta_C$ (125 MHz, DMSO-d$_6$) 55.6, 55.7, 110.5, 111.6, 112.9, 116.5, 123.4, 127.2, 137.3, 143.0, 149.1, 151.3, 157.1, 157.5, 159.4, 160.1; HRMS (ESI) calculated for C$_{17}$H$_{15}$N$_2$O$_4$ [M+H]$^+$ 311.1026, found 311.1025; $v_{max}$ 798, 1024, 1417, 1563, 1757, 2836, 2958 cm$^{-1}$.

(E)-2-(3,4-Dimethoxystyryl)-4H-benzo[d][1,3]oxazin-4-one (FT106)

2-[(Carboxyacetyl)amino]benzoic Acid

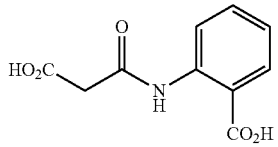

Anthranilic acid (300 g, 2.08 mol) was added to a solution of Meldrum's acid (272 g, 1.98 mol) in toluene (2.0 L). The reaction flask was fitted with a Dean-Stark apparatus and the suspension was heated to reflux for 3 h. The suspension was cooled, filtered, washed with toluene and dried. 2-[(Carboxyacetyl)amino]benzoic acid (381 g, 86%) was obtained as a colourless solid; mp 171-173° C.; $\delta_H$ (500 MHz, DMSO-d$_6$) 3.45 (br s, 2H, CH$_2$), 7.16 (t, J$_{3,4}$=J$_{4,5}$=8.0 Hz, 1H, H4), 7.59 (td, J$_{4,5}$=J$_{5,6}$=8.0, J$_{3,5}$=1.5 Hz, 1H, H5), 7.97 (dd, J$_{3,4}$=8.0, J$_{3,5}$=1.5 Hz, 1H, H3), 8.44 (d, J$_{5,6}$=8.0 Hz, 1H, H6), 11.27 (s, 1H, NH), 12.83 (br s, 1H, CO$_2$H), 13.57 (br s, 1H, CO$_2$H); $\delta_C$ (125 MHz, DMSO-d$_6$) 45.0, 117.0, 120.3, 123.1, 131.2, 134.1, 140.4, 164.9, 169.1, 169.3; $v_{max}$ 760, 1234, 1385, 1544, 1684, 1712, 2653, 2964, 3119 cm$^{-1}$.

(E)-2-[[3-(3,4-Dimethoxyphenyl)-1-oxo-2-propenyl]amino]benzoic acid (tranilast)

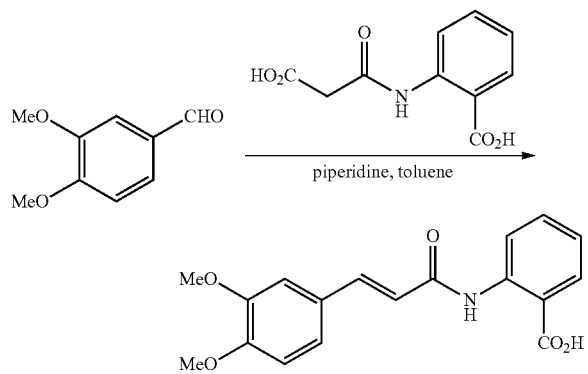

Piperidine (0.96 mL, 9.7 mmol) was added to a suspension of 3,4-dimethoxybenzaldehyde (1.6 g, 9.7 mmol) and 2-[(carboxyacetyl)amino]benzoic acid (1.9 g, 8.6 mmol) in toluene (5.0 mL). The reaction flask was fitted with a Dean-Stark apparatus and heated to reflux for 4 h, then cooled to rt and the resulting suspension was filtered and washed with toluene. The piperidinium salt was dissolved in MeOH (5.0 mL) and water (2.0 mL) at 40° C. and the solution was acidified with concentrated HCl. The precipitate was filtered, providing (E)-2-[[3-(3,4-dimethoxyphenyl)-1-oxo-2-propenyl]amino]benzoic acid (tranilast) (2.1 g, 74%) as a yellow crystalline solid; mp 208-209° C., lit.[2] 206° C.; $\delta_H$ (500 MHz, DMSO-$d_6$) 3.79 (s, 3H, OCH$_3$), 3.82 (s, 3H; OCH$_3$), 6.79 (d, J=15.5 Hz, 1H, CH=CHCO), 6.99 (d, $J_{5',4'}$=8.5 Hz, 1H, H5'), 7.16 (t, $J_{3,4}$=$J_{4,5}$=7.9 Hz, 1H, H4), 7.25 (d, $J_{5',6'}$=8.5 Hz, 1H, H6'), 7.38 (s, 1H, H2'), 7.56 (d, J=15.5 Hz, 1H, CH=CHCO), 7.61 ($J_{4,5}$=$J_{5,6}$=7.9 Hz, 1H, H5), 8.00 (d, $J_{3,4}$=7.9 Hz, 1H, H3), 8.62 (d, $J_{5,6}$=7.9 Hz, 1H, H6), 11.30 (s, 1H, NH), 13.61 (br s, 1H, CO$_2$H).

(E)-2-(3,4-Dimethoxystyryl)-4H-benzo[d][1,3]oxazin-4-one (FT106)

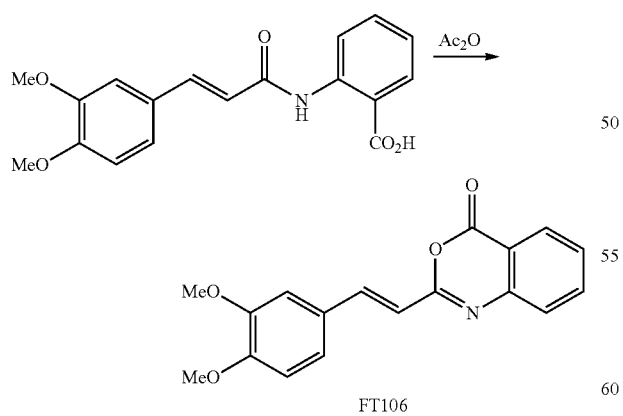

A solution of (E)-2-[[3-(3,4-dimethoxyphenyl)-1-oxo-2-propenyl]amino]benzoic acid (0.5 g, 1.5 mmol) in acetic anhydride (3 mL) was heated to reflux and stirred for 3 h. The reaction was cooled to rt and the resulting suspension was diluted with water. The suspension was stirred at rt for 1 h and the precipitate was collected by filtration, providing (E)-2-(3,4-dimethoxystyryl)-4H-benzo[d][1,3]oxazin-4-one (0.41 g, 88%) as a yellow crystalline solid; mp 175-179° C.; $\delta_H$ (500 MHz, DMSO-$d_6$) 3.82 (s, 3H, OCH$_3$), 3.85 (s, 3H, OCH$_3$), 6.94 (d, J=16.0 Hz, 1H, CH=CHCO), 7.02 (d, $J_{5',6'}$=8.0 Hz, 1H, H5'), 7.35 (dd, $J_{5',6}$=8.0, $J_{2',6'}$=1.5 Hz, 1H, H6'), 7.47 (d, $J_{2,6'}$=1.5 Hz, 1H, H2'), 7.58 (t, $J_{3,4}$=$J_{4,5}$=8.0 Hz, 1H, H4), 7.61 (d, $J_{3,4}$=8.0 Hz, 1H, H3), 7.73 (d, J=16.0 Hz, 1H, CH=CHCO), 7.92 (t, $J_{4,5}$=$J_{5,6}$=8.0 Hz, 1H, H5), 8.12 (d, $J_{5,6}$=8.0 Hz, 1H, H6); $\delta_C$ (125 MHz, DMSO-$d_6$) 55.5, 55.6, 110.3, 111.6, 116.6, 122.9, 126.5, 127.4, 128.0, 128.0, 128.1, 136.8, 141.4, 146.8, 149.0, 150.9, 157.3, 158.8; HRMS (ESI) calculated for $C_{18}H_{15}NO_4$ [M+H]$^+$310.1074; found 310.1073; $\nu_{max}$ 1020, 1254, 1515, 1634, 1755, 2835, 2940 cm$^{-1}$.

(E)-2-(3-Methoxy-4-propargyloxystyryl)-4H-benzo[d][1,3]oxazin-4-one (FT107)

3-Methoxy-4-propargyloxybenzaldehyde

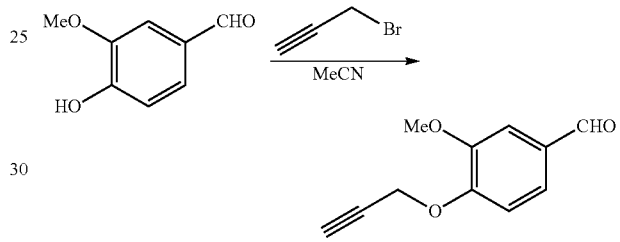

Propargyl bromide (293 mL, 80% w/v, 1.97 mol) was added to a suspension of vanillin (250 g, 1.64 mol) and potassium carbonate (681 g, 4.93 mol) in MeCN (2.0 L). The suspension was heated to reflux for 6 h and the solvent was removed under reduced pressure. Water was added and the aqueous phase was extracted with EtOAc, washed with water, brine and dried. The solvent was removed under reduced pressure to give 3-methoxy-4-propargyloxybenzaldehyde (302 g, 97%) as yellow crystalline solid; mp 95° C.; $\delta_H$ (400 MHz, CDCl$_3$) 2.56 (t, J=2.5 Hz, 1H, C≡CH), 3.95 (s, 3H, OCH$_3$), 4.86 (d, J=2.5 Hz, 2H, OCH$_2$); 7.14 (d, $J_{5,6}$=6.8 Hz, 1H, H5), 7.44 (d, $J_{2,6}$=1.4 Hz, 1H, H2), 7.47 (dd, $J_{5,6}$=6.8, $J_{2,6}$=1.4 Hz, 1H, H6), 9.87 (s, 1H, CHO); $\delta_C$ (100 MHz, CDCl$_3$) 56.0, 56.6, 77.2, 77.4, 109.4, 112.5, 126.3, 130.9, 150.0, 152.1, 190.9; HRMS (ESI) Calculated for $C_{11}H_{10}O_3$ [M+H]$^+$, 191.0703 found 191.0706; $\nu_{max}$ 1006, 1130, 1259, 1586, 1677, 2119, 2845, 2932, 3266 cm$^{-1}$.

(E)-2-[[3-(3-Methoxy-4-propargyloxyphenyl)-1-oxo-2-propenyl]amino]benzoic acid

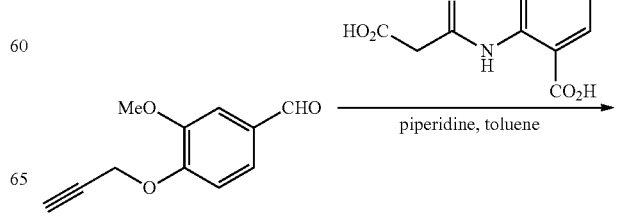

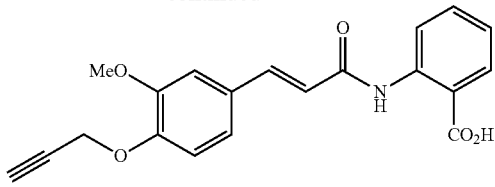

Piperidine (158 mL, 1.59 mol) was added to a suspension of 3-methoxy-4-propargyloxybenzaldehyde (302 g, 1.59 mol) and 2-[(carboxyacetyl)amino]benzoic acid (322 g, 1.44 mol) in toluene (1.5 L). The reaction flask was fitted with a Dean-Stark apparatus and heated to reflux for 30 min. The reaction was then cooled to rt and the resulting suspension was filtered and washed with toluene. The piperidinium salt was dissolved in MeOH (4 L) and water (1 L) at 50° C. and the solution was acidified with 50% aqueous AcOH. The precipitate was filtered and the crude product was recrystallised from EtOH (35 mL/g), filtered and washed with cooled EtOH to afford (E)-2-[[3-(3-methoxy-4-propargyloxyphenyl)-1-oxo-2-propenyl]amino]benzoic acid (309 g, 61%) as a yellow crystalline solid; mp 201-203° C.; $\delta_H$ (400 MHz, DMSO-$d_6$) 3.59 (t, J=2.4 Hz, 1H, C≡CH), 3.84 (s, 3H, OCH$_3$), 4.84 (d, J=2.4 Hz, 2H, OCH$_2$), 6.81 (d, J=15.6 Hz, 1H, CH=CHCO), 7.05 (d, $J_{5,6}$=8.4 Hz, 1H, H5'), 7.16 (t, $J_{3,4}$=$J_{4,5}$=8.0 Hz, 1H, H4), 7.25 (d, $J_{5',6'}$=8.4 Hz, 1H, H6'), 7.41 (s, 1H, H2'), 7.56 (d, J=15.6 Hz, 1H, CH=CHCO), 7.61 (t, $J_{4,5}$=$J_{5,6}$=8.0 Hz, 1H, H5), 8.00 (d, $J_{3,4}$=8.0 Hz, 1H, H3), 8.62 (d, $J_{5,6}$=8.0 Hz, 1H, H6), 11.31 (s, 1H, NH), 13.57 (br s, 1H, CO$_2$H); $\delta_C$ (100 MHz, DMSO-$d_6$) 55.6, 55.9, 78.6, 79.1, 110.8, 113.5, 116.6, 120.4, 120.4, 122.2, 122.7, 128.2, 131.2, 134.0, 141.0, 141.5, 148.3, 149.3, 164.1, 169.5; HRMS (ESI) calculated for $C_{20}H_{17}NO_5$ [M+H]$^+$ 352.1179, found 352.1187; $\nu_{max}$ 755, 1010, 1140, 1253, 1502, 1582, 1657, 3278, 3522 cm$^{-1}$.

(E)-2-(3-Methoxy-4-propargyloxystyryl)-4H-benzo[d][1,3]oxazin-4-one (FT107)

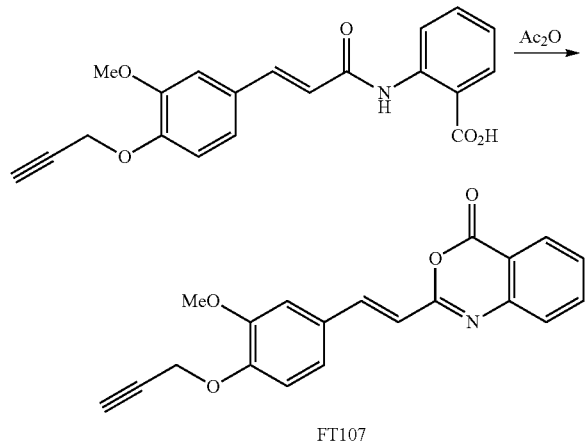

A solution of (E)-2-[[3-(3-methoxy-4-propargyloxyphenyl)-1-oxo-2-propenyl]amino]benzoic acid (0.5 g, 1.4 mmol) in acetic anhydride (3 mL) was ~5 heated to reflux and stirred for 3 h. The reaction was cooled to rt and the resulting suspension was diluted with water. The suspension was stirred at rt for 1 h and the precipitate was collected by filtration, providing (E)-2-(3-methoxy-4-propargyloxystyryl)-4H-benzo[d][1,3]oxazin-4-one (0.44 g, 93%) as a yellow crystalline solid; mp 177-178° C.; $\delta_H$ (500 MHz, DMSO-d) 3.59 (m, 1H, C≡CH), 3.85 (s, 3H, OCH$_3$), 4.85 (s, 2H, OCH$_2$), 6.96 (d, J=16.0 Hz, 1H, CH=CHCO), 7.07 (d, $J_{5,6}$=8.0 Hz, 1H, H5'), 7.34 (d, $J_{5',6'}$=8.0, 1H, H6'), 7.49 (s, 1H, H2'), 7.57 (t, $J_{3,4}$=$J_{4,5}$=8.0 Hz, 1H, H4), 7.60 (d, $J_{3,4}$=8.0 Hz, 1H, H3), 7.72 (d, J=16.0 Hz, 1H, CH=CHCO), 7.91 (t, $J_{4,5}$=$J_{5,6}$=8.0 Hz, 1H, H5), 8.11 (d, $J_{5,6}$=8.0 Hz, 1H, H6); $\nu_C$ (125 MHz, DMSO-$d_6$) 55.7, 55.9, 78.5, 79.0, 110.8, 113.6, 117.0, 117.2, 122.3, 126.5, 128.0, 128.1, 128.3, 136.8, 141.2, 146.8, 148.5, 149.4, 157.2, 158.8; HRMS (ESI) calculated for $C_{20}H_{15}NO_4$ [M+H]$^+$ 334.1074, found 334.1074; $\nu_{max}$ 970, 1136, 1270, 1471, 1743, 2135, 3268 cm$^{-1}$.

(E)-2-(3,4-Bis(difluoromethoxy)styryl)-4H-benzo[d][1,3]oxazin-4-one (FT108)

(E)-2-[[3,4-Bis(difluoromethoxy)phenyl)-1-oxo-2-propenyl]amino]benzoic acid

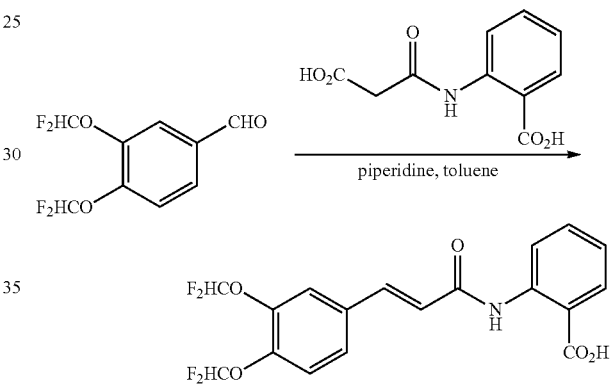

Piperidine (100 μL, 1.01 mmol) was added to a suspension of 3,4-bis(difluoromethoxy)benzaldehyde (240 mg, 1.01 mmol) and 2-[(carboxyacetyl)amino]benzoic acid (204 mg, 0.92 mmol) in toluene (5.0 mL). The reaction flask was fitted with a Dean-Stark apparatus and heated to reflux for 30 min. The reaction was then cooled to rt and the resulting suspension was filtered and washed with toluene. The piperidinium salt was dissolved in MeOH (5 mL) and water (2 mL) and the solution was acidified with 50% aqueous AcOH. The crude product was collected by filtration and recrystallised from EtOH/water, filtered and washed with water to afford (E)-2-[[3,4-bis(difluoromethoxy)phenyl)-1-oxo-2-propenyl]amino]benzoic acid (259 mg, 71%) as a colourless crystalline solid; mp 190-193° C.; $\delta_H$ (400 MHz, DMSO-$d_6$) 6.96 (d, J=15.6 Hz, 1H, CH=CHCO), 7.18 (t, $J_{3,4}$=$J_{4,5}$=8.0 Hz, 1H, H4), 7.27 (t, J=73 Hz, 2H, OCHF$_2$), 7.38 (d, $J_{5',6'}$=8.0 Hz, 1H, H5'), 7.61 (d, J=15.6 Hz, 1H, CH=CHCO), 7.62 (t, $J_{4,5}$=$J_{5,6}$=8.0 Hz, 1H, H5), 7.78 (d, $J_{2',6'}$=1.6 Hz, 1H, H2'), 7.68 (dd, $J_{5',6'}$=8.0, $J_{2',6'}$=1.6 Hz, 1H, H6'), 8.00 (d, $J_{3,4}$=8.0 Hz, 1H, H3), 8.69 (d, $J_{5,6}$=8.0 Hz, 1H, H6), 11.35 (s, 1H, NH), 13.56 (br s, 1H, CO$_2$H); $\delta_C$ (100 MHz, DMSO-$d_6$) 116.3 (t, J=258 Hz), 116.5 (t, J=258 Hz), 117.0, 120.1, 120.5, 120.8, 123.0, 123.8, 126.7, 131.1, 132.8, 133.9, 139.3, 140.7, 141.9, 142.7, 163.5, 169.4; HRMS (ESI) calculated for $C_{18}H_{13}F_4NO_5$ [M−H]$^-$ 398.0646, found 398.0652; $\nu_{max}$ 1034, 1217, 1513, 1604, 1683, 2892, 3466 cm$^{-1}$.

(E)-2-(3,4-Bis(difluoromethoxy)styryl)-4H-benzo[d][1,3]oxazin-4-one (FT108)

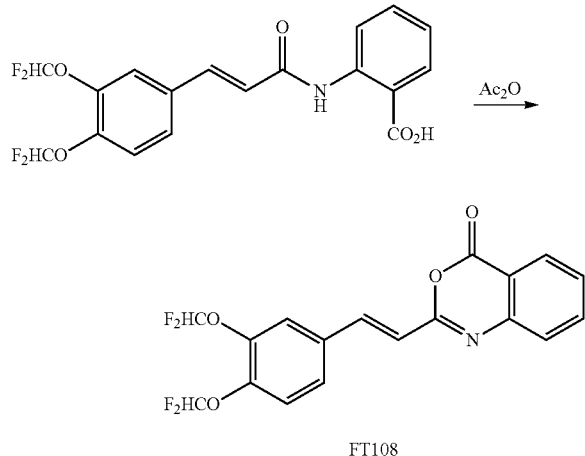

FT108

A solution of (E)-2-[[3,4-bis(difluoromethoxy)phenyl]-1-oxo-2-propenyl]amino]benzoic acid (0.5 g, 1.2 mmol) in acetic anhydride (3 mL) was heated to reflux and stirred for 3 h. The reaction was cooled to rt and the resulting suspension was diluted with water. The suspension was stirred at rt for 1 h and the precipitate was collected by filtration, providing (E)-2-(3,4-bis(difluoromethoxy)styryl)-4H-benzo[d][1,3]oxazin-4-one (0.41 g, 86%) as a colourless crystalline solid; mp 113-115° C.; $\delta_H$ (500 MHz, DMSO-d$_6$) 7.07 (d, J=16.0 Hz, 1H, CH=CHCO), 7.29 (t, J=74 Hz, 1H, OCHF$_2$), 7.28 (t, J=74 Hz, 1H, OCHF$_2$), 7.39 (d, J$_{5',6'}$=8.0 Hz, 1H, H5'), 7.60 (t, J$_{3,4}$=J$_{4,5}$=8.0 Hz, 1H, H4), 7.62 (d, J$_{3,4}$=8.0 Hz, H, H3), 7.75 (d, J$_{5',6'}$=8.0, 1H, H6'), 7.76 (d, J=16.0 Hz, 1H, CH=CHCO), 7.87 (s, 1H, H2'), 7.92 (t, J$_{4,5}$=J$_{5,6}$=8.0 Hz, 1H, H5), 8.12 (d, J$_{5,6}$=8.0 Hz, 1H, H6); $\delta_C$ (125 MHz, DMSO-d$_6$) 116.3 (t, J=258. Hz), 116.4 (t, J=258 Hz), 116.9, 119.9, 120.6, 120.8, 126.5, 126.7, 128.1, 128.6, 132.9, 136.8, 139.0, 141.2, 142.0, 146.5, 156.5, 158.7; HRMS (ESI) calculated for C$_{18}$H$_1$F$_4$NO$_4$ [M+H]$^+$ 382.0697, found 382.0696; $\nu_{max}$ 969, 1042, 1087, 1123, 1279, 1383, 1472, 1595, 1747 cm$^{-1}$.

(E)-2-(4-Acetoxy-3-methoxystyryl)-4H-benzo[d][1,3]oxazin-4-one (FT109)

(E)-2-[[3-(4-Hydroxy-3-methoxyphenyl)-1-oxo-2-propenyl]amino]benzoic acid

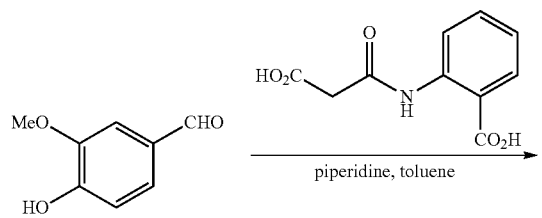

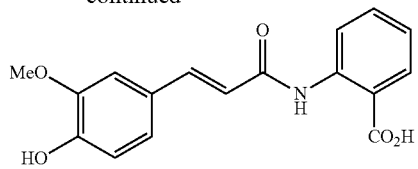

Piperidine (0.50 mL, 5.1 mmol) was added to a suspension of 4-hydroxy-3-methoxybenzaldehyde (0.77 g, 5.1 mmol) and 2-[(carboxyacetyl)amino]benzoic acid (1.0 g, 4.5 mmol) in toluene (5.0 mL). The reaction flask was fitted with a Dean-Stark apparatus and heated to reflux for 3 h, then cooled to rt and the resulting suspension was filtered and washed with toluene. The piperidinium salt was dissolved in MeOH (12.0 mL) and water (12.0 mL) at 40° C. and the solution was acidified with concentrated HCl. The precipitate was filtered, providing (E)-2-[[3-(4-hydroxy-3-methoxyphenyl)-1-oxo-2-propenyl]amino]benzoic acid (1.1 g, 78%) as a yellow crystalline solid; mp 207.5-208.5° C., lit.[5] 230-233° C.; $\delta_H$ (500 MHz, DMSO-d$_6$) 3.83 (s, 3H, OCH$_3$), 6.71 (d, J=15.5 Hz, 1H, CH=CHCO), 6.80 (d, J$_{5',6'}$=8.5 Hz, 1H, H5'), 7.13 (dd, J$_{5,6}$=8.5, J$_{2',6'}$=1.5 Hz, 1H, H6'), 7.15 (t, J$_{3,4}$=J$_{4,5}$=8.0 Hz, 1H, H4), 7.34 (d, J$_{2',6'}$=1.5 Hz, 1H, H2'), 7.52 (d, J=15.5 Hz, 1H, CH=CHCO), 7.60 (td, J$_{4,5}$=J$_{5,6}$=8.0, J$_{3,5}$=2.0 Hz, 1H, H5), 8.00 (dd, J$_{3,4}$=8.0, J$_{3,5}$=2.0 Hz, 1H, H3), 8.62 (d, J$_{5,6}$=8.0 Hz, 1H, H6), 9.57 (s, 1H, OH), 11.27 (s, 1H, NH), 13.61 (br s, 1H, CO$_2$H).

(E)-2-(4-Acetoxy-3-methoxystyryl)-4H-benzo[d][1,3]oxazin-4-one (FT109)

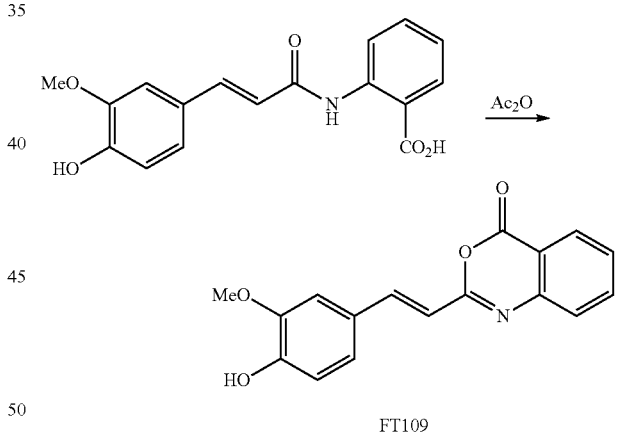

FT109

A solution of (E)-2-[[3-(4-hydroxy-3-methoxyphenyl)-1-oxo-2-propenyl]amino]benzoic acid (0.5 g, 1.6 mmol) in acetic anhydride (3 mL) was heated to reflux and stirred for 3 h. The reaction was cooled to rt and the resulting suspension was diluted with water. The suspension was stirred at rt for 1 h and the precipitate was collected by filtration, providing (E)-2-(4-acetoxy-3-methoxystyryl)-4H-benzo[d][1,3]oxazin-4-one (0.52 g, 97%) as a pale brown solid; mp 185-186° C.; $\delta_H$ (400 MHz, DMSO-d$_6$) 2.63 (s, 3H, COCH$_3$), 3.85 (s, 3H, OCH$_3$), 7.08 (d, J=16.0 Hz, 1H, CH=CHCO), 7.17 (d, J$_{5',6'}$=8.0 Hz, 1H, H5'), 7.38 (d, J$_{5',6'}$=8.0 Hz, 1H, H6'), 7.59 (t, J$_{3,4}$=J$_{4,5}$=8.0 Hz, 1H, H4), 7.61 (d, J$_{3,4}$=8.0 Hz, 1H, H3), 7.63 (s, 1H, H2'), 7.76 (d, J=16.0 Hz, 1H, CH=CHCO), 7.92 (t, J$_{4,5}$=J$_{5,6}$=8.0 Hz, 1H, H5), 8.11 (d, J$_{5,6}$=8.0 Hz, 1H, H6); $\delta_C$ (100 MHz, DMSO-d$_6$) 20.4, 56.0, 111.9, 116.9, 119.5, 121.4, 123.3, 126.6, 128.1, 128.4, 133.5, 136.8, 140.5, 140.9, 146.6, 151.2, 156.8, 168.4; HRMS (ESI) calculated for $C_{19}H_5NO_5$ [M+H]$^+$ 338.1023; found 338.1023; $\nu_{max}$ 1197, 1214, 1593, 1635, 1748 cm$^{-1}$.

(E)-2-(3-Acetoxy-4-methoxystyryl)-4H-benzo[d][1,3]oxazin-4-one (FT110)

(E)-2-[[3-(3-Hydroxy-4-methoxyphenyl)-1-oxo-2-propenyl]amino]benzoic acid

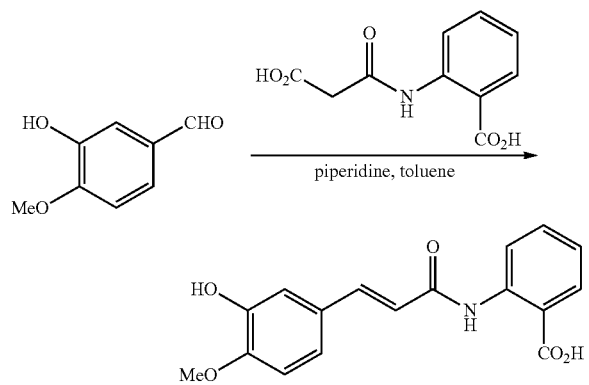

Piperidine (0.25 mL, 2.5 mmol) was added to a suspension of 3-hydroxy-4-methoxybenzaldehyde (0.39 g, 2.5 mmol) and 2-[(carboxyacetyl)amino]benzoic acid (0.50 g, 2.2 mmol) in toluene (5.0 mL). The reaction flask was fitted with a Dean-Stark apparatus and heated to reflux for 3 h, then cooled to rt and the resulting suspension was filtered and washed with toluene. The piperidinium salt was dissolved in MeOH (5.0 mL) and water (2.0 mL) at 40° C. and the solution was acidified with concentrated HCl. The precipitate was filtered, providing (E)-2-[[3-(3-hydroxy-4-methoxyphenyl)-1-oxo-2-propenyl]amino]benzoic acid (0.53 g, 76%) as a yellow crystalline solid; mp 215-216° C., lit.$^5$ 219-222° C.; $\delta_H$ (500 MHz, DMSO-d$_6$) 3.81 (s, 3H, OCH$_3$), 6.59 (d, J=15.5 Hz, 1H, CH=CHCO), 6.80 (d, J$_{5',6'}$=8.5 Hz, 1H, H5'), 7.10-7.13 (m, 2H, H2', H6'), 7.15 (t, J$_{3,4}$=J$_{4,5}$=8.0 Hz, 1H, H4), 7.47 (d, J=15.5 Hz, 1H, CH=CHCO), 7.60 (td, J$_{4,5}$=J$_{5,6}$=8.0, J$_{3,5}$=1.5 Hz, 1H, H5), 7.99 (dd, J$_{3,4}$=8.0, J$_{3,5}$=1.5 Hz, 1H, H3), 8.58 (d, J$_{5,6}$=8.0 Hz, 1H, H6), 11.25 (s, 1H, NH), 13.56 (br s, 1H, CO$_2$H).

(E)-2-(3-Acetoxy-4-methoxystyryl)-4H-benzo[d][1,3]oxazin-4-one (FT110)

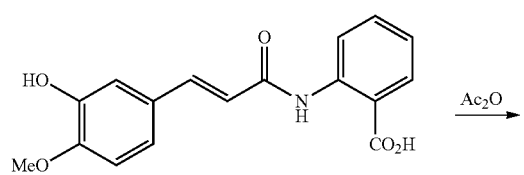

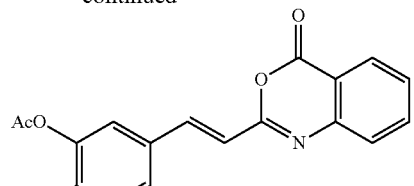

FT110

A solution of (E)-2-[[3-(3-hydroxy-4-methoxyphenyl)-1-oxo-2-propenyl]amino]benzoic acid (0.5 g, 1.6 mmol) in acetic anhydride (3 mL) was heated to reflux and stirred for 3 h. The reaction was cooled to rt and the resulting suspension was diluted with water. The suspension was stirred at it for 1 h and the precipitate was collected by filtration, providing (E)-2-(3-acetoxy-4-methoxystyryl)-4H-benzo[d][1,3]oxazin-4-one (0.50 g, 93%) as a yellow solid; mp 187-190° C.; $\delta_H$ (400 MHz, DMSO-d$_6$) 2.80 (s, 3H, COCH$_3$), 3.83 (s, 3H, OCH$_3$), 6.87 (d, J=16.0 Hz, 1H, CH=CHCO), 7.19 (d, J$_{5',6'}$=8.0 Hz, 1H, H5'), 7.68 (d, J$_{5',6'}$=8.0, 1H, H6'), 7.57 (t, J$_{3,4}$=J$_{4,5}$=8.0 Hz, 1H, H4), 7.60 (d, J$_{3,4}$=8.0 Hz, 1H, H3), 7.66 (s, 1H, H2'), 7.71 (d, J=16.0 Hz, 1H, CH=CHCO), 7.89 (t, J$_{4,5}$=J$_{5,6}$=8.0 Hz, 1H, H5), 8.10 (d, J$_{5,6}$=8.0 Hz, 1H, H6); $\delta_C$ (100 MHz, DMSO-d$_6$) 20.4, 56.1, 112.9, 116.7, 117.6, 122.1, 127.5, 128.0, 128.1, 128.2, 136.8, 139.6, 140.2, 146.7, 152.7, 157.0, 158.8, 168.4; HRMS (ESI) calculated for $C_{19}H_{15}NO_5$ [M+H]$^+$ 338.1023, found 338.1023; $\nu_{max}$ 1197, 1268, 1588, 1631, 1752 cm$^{-1}$.

(E)-3-(3,4-dimethoxyphenyl)-1-(indolin-1-yl)prop-2-en-1-one (FT113)

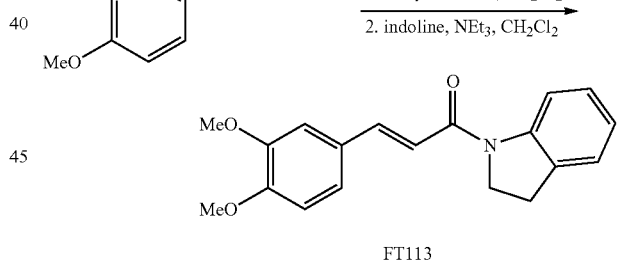

FT113

A suspension of (E)-3-(3,4-dimethoxyphenyl)acrylic acid (0.50 g, 2.4 mmol) in CH$_2$Cl$_2$ (5 mL) was treated with oxalyl chloride (0.80 mL, 9.6 mmol). The solution was stirred at rt for 2 h and the solvent was removed under reduced pressure to give the acid chloride. Indoline (0.27 g, 2.4 mmol) was added to a solution of the acid chloride (2.4 mmol) in CH$_2$Cl$_2$ (5 mL) and NEt$_3$ (0.67 mL, 4.8 mmol). The mixture was stirred at rt for 16 h and concentrated under reduced pressure. The residue was diluted with water and the resulting precipitate was collected by filtration and recrystallised from EtOAc providing (E)-3-(3,4-dimethoxyphenyl)-1-(indolin-1-yl)prop-2-en-1-one (0.15 g, 20%) as a colourless crystalline solid; mp 118-120° C.; $\delta_H$ (500 MHz, DMSO-d$_6$) 3.18 (t, J=8.0 Hz, 2H, CH$_2$), 3.79 (s, 3H, OCH$_3$), 3.83 (s, 3H, OCH$_3$), 4.33 (t, J=8.0 Hz, 2H, NCH$_2$), 6.98-7.02 (m, 3H, CH=CHCO, H5, H6), 7.16 (t, J$_{3,4}$=J$_{4,5}$=8.0 Hz, 1H, H4), 7.25 (d, J$_{5',6'}$=8.0 Hz, 1H, H5'), 7.26 (dd, J$_{5',6'}$=8.0 Hz, J$_{2',6'}$=2.0 Hz, 1H, H6'), 7.38 (d, $J_{2',6'}$=2.0 Hz, 1H, H2'), 7.58 (d, J=15.5 Hz, 1H, CH=CHCO), 8.19 (m, 1H, H3); $\delta_C$ (125 MHz, DMSO-$d_6$) 27.3, 47.7, 55.5, 55.6, 110.6, 111.6, 116.4, 117.5, 122.6, 123.3, 124.8, 126.9, 127.7, 132.2, 142.3, 143.1, 148.9, 150.6, 163.9; HRMS (ESI) calculated for $C_{19}H_{19}NO_3$ [M+H]$^+$ 310.1438, found 310.1437; $v_{max}$ 1025, 1145, 1262, 1398, 1510, 1646 cm$^{-1}$.

(E)-2-(3,4-Dimethoxystyryl)-H-benzo[d]imidazole (FT121)

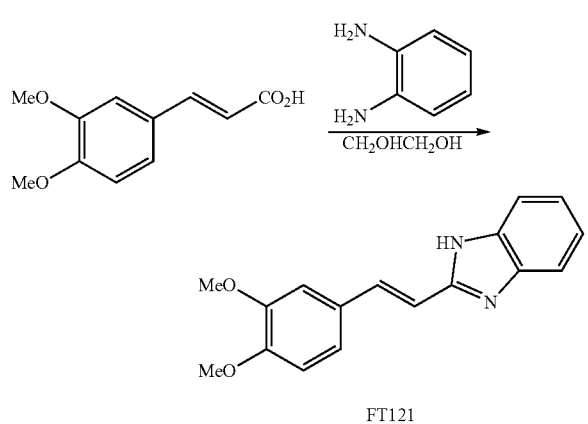

FT121

A mixture of (E)-3-(3,4-dimethoxyphenyl)acrylic acid (416 mg, 2.0 mmol) and o-phenylenediamine sulfuric acid (412 mg, 2.0 mmol) in ethylene glycol (10 mL) was heated at reflux for three hours. The mixture was then cooled to room temperature and poured into water (50 mL). The pH of the solution was adjusted to >7 with NaHCO$_3$ and extracted with DCM. The organic layer was washed with saturated aqueous NaCl solution and dried over sodium sulfate. The solvent was concentrated under a reduced pressure and the residue was purified by flash chromatography on silica gel using petroleum ether/ethyl acetate 2:1 (v:v) as eluent to give (E)-2-(3,4-dimethoxystyryl)-1H-benzo[d]imidazole (130 mg, 23%). $^1$H-NMR (400 MHz, CDCl$_3$) δ 3.78 (s, 3H), 3.88 (s, 3H), 6.80 (d, J=8.0 Hz, 1H), 6.96-7.00 (m, 2H), 7.06 (d, J=16.0 Hz, 1H), 7.25-7.29 (m, 2H), 7.59 (d, J=16.0 Hz, 1H), 7.64 (m, 2H); LC-MS (ES-API); rt 7.55 min; m/z calculated for $C_{17}H_{16}N_2O_2$ [M+H]$^+$ 281.1, found 281.1.

(E)-1-(2,3-Dihydrobenzo[b][1,4]oxazin-4-yl)-3-(3,4-dimethoxyphenyl)prop-2-en-1-one (FT122)

3,4-Dihydro-2H-benzo[b][1,4]oxazine

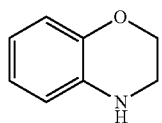

To a suspension of 2-aminophenol (1.0 g, 9.2 mmol) and potassium carbonate (6.36 g, 46 mmol) in dry DMF (10 mL) was added 1,2-dibromoethane (2.59 g, 13.8 mmol). The mixture was then heated at 125° C. for 15 hours. After cooling, the mixture was treated with crushed ice and extracted with ethyl acetate. The organic extracts were dried over sodium sulfate and the solvent was removed under reduced pressure. The residue was purified by flash chromatography on silica gel using ethyl acetate/petroleum ether 1:10 (v:v) as eluent to give 3,4-dihydro-2H-benzo[b][1,4]oxazine as reddish oil (0.81 g, 65%). LC-MS (ES-API); rt 7.51 min; m/z calculated for $C_8H_9NO$ [M+H]$^+$ 136.1, found 136.1.

(E)-1-(2,3-Dihydrobenzo[b][1,4]oxazin-4-yl)-3-(3,4-dimethoxyphenyl)prop-2-en-1-one (FT122)

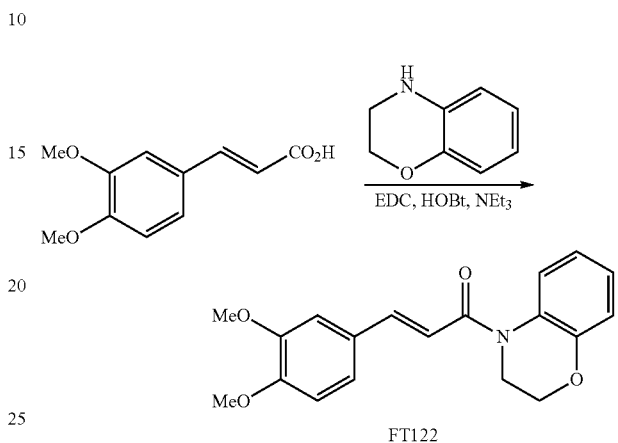

FT122

To a solution of (E)-3-(3,4-dimethoxyphenyl)acrylic acid (0.46 g, 2.22 mmol) and 3,4-dihydro-2H-benzo[b][1,4]oxazine (0.20 g, 1.48 mmol) in DCM (15 mL) was added EDC.HCl (0.71 g, 3.70 mmol), HOBt (0.60 g, 3.70 mmol) and Et$_3$N (0.37 g, 3.70 mmol). The mixture was stirred at room temperature overnight then diluted with water and extracted with DCM. The organic layer was dried over sodium sulfate and the solvent was removed under reduced pressure. The residue was purified by column chromatography on silica gel using petroleum ether/ethyl acetate 5:1 (v:v) as eluent to give (E)-1-(2,3-dihydrobenzo[b][1,4]oxazin-4-yl)-3-(3,4-dimethoxyphenyl)prop-2-en-1-one (230 mg, 32%). $^1$H-NMR (400 MHz, CDCl$_3$) δ 3.88 (s, 3H), 3.91 (s, 3H), 4.08 (m, 2H), 4.37 (m, 2H), 6.86 (d, J=8.4 Hz, 1H), 6.90 (m, 1H), 6.92 (d, J=15.2 Hz, 1H), 6.96 (dd, J=8.0, 1.6 Hz, 1H), 6.99 (d, J=2.0 Hz, 1H), 7.08-7.13 (m, 2H), 7.20 (br d, J=7.6 Hz, 1H), 7.02 (d, J=15.6 Hz, 1H); LC-MS (ES-API); rt 8.72 min; m/z calculated for $C_{19}H_{19}NO_4$ [M+H]$^+$ 326.1, found 326.1.

(E)-1-(3-(3,4-Dimethoxyphenyl)acryloyl)-3-methyl-1H-benzo[d]imidazol-2(3H)-one (FT123)

(E)-3-(3,4-Dimethoxyphenyl)acryloyl chloride

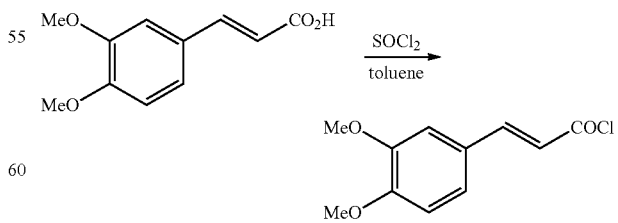

To a suspension of 3-(3,4-dimethoxyphenyl)acrylic acid (416 mg 2 mmol) in toluene (10 mL) was added thionyl chloride (1.45 mL, 20 mmol). The solution was heated at 50° C. for 1 hour and then the solvent was removed under reduced pressure to give (E)-3-(3,4-dimethoxyphenyl)acryloyl chloride, which was used directly in the next step without purification.

(E)-1-(3-(3,4-Dimethoxyphenyl)acryloyl)-1H-benzo[d]imidazol-2(3H)-one

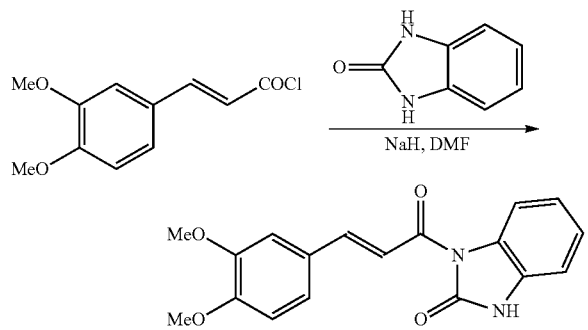

To a solution of 1H-benzo[d]imidazol-2(3H)-one (268 mg, 2 mmol) in DMF (10 mL) at 0° C. was added 60% oily sodium hydride (88 mg, 2.2 mmol). When hydrogen evolution had ceased, a solution of (E)-3-(3,4-dimethoxyphenyl)acryloyl chloride (240 mg, 0.75 mmol) in DMF (3 mL) was added and the reaction mixture allowed to warm to room temperature and stirred for 1 hour. The reaction was quenched by addition of 1N hydrochloric acid, and extracted with DCM. The combined organic phases were washed with brine and dried over sodium sulfate. After concentration under reduced pressure, the residue was purified by flash column (hexane-EtOAc, 25:10) to give (E)-1-(3-(3,4-dimethoxyphenyl)acryloyl)-1H-benzo[d]imidazol-2(3H)-one (240 mg, 37%). LC-MS (ES-API); rt 9.02 min; m/z calculated for $C_{18}H_{16}N_2O_4$ $[M+H]^+$ 325.1, found 325.0 and 347.0 ($[M+Na]^+$).

(E)-1-(3-(3,4-Dimethoxyphenyl)acryloyl)-3-methyl-1H-benzo[d]imidazol-2(3H)-one (FT123)

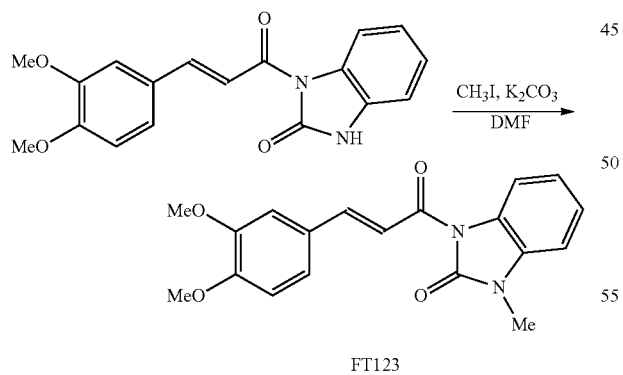

A mixture of (E)-1-(3-(3,4-dimethoxyphenyl)acryloyl)-1H-benzo[d]imidazol-2(3H)-one (240 mg, 0.75 mmol), iodomethane (68 uL, 1.1 mmol) and $K_2CO_3$ (204 mg, 1.5 mmol) in DMF (5 mL) was stirred at room temperature overnight. The reaction was quenched with water and extracted with DCM. The combined organic phases were washed with brine, dried over sodium sulfate and the solvent removed under reduced pressure. The residue was purified by recrystallisation from EtOH to afford (E)-1-(3-(3,4-dimethoxyphenyl)acryloyl)-3-methyl-1H-benzo[d]imidazol-2(3H)-one (200 mg, 79%). $^1$H-NMR (400 MHz, CDCl$_3$) δ 3.46 (s, 3H), 3.96 (s, 3H), 3.98 (s, 3H), 6.91 (d, J=8.4 Hz, 1H), 7.01 (dd, J=7.6, 0.8 Hz, 1H), 7.19-7.28 (m, 4H), 7.98 (d, J=15.6 Hz, 1H), 8.15 (d, J=15.6 Hz, 1H) 8.32 (dd, J=8.0, 0.8 Hz, 1H); LC-MS (ES-API); rt 9.05 min; m/z calculated for $C_{19}H_{18}N_2O_4$ $[M+H]^+$ 339.1, found 339.0 and 361.0 ($[M+Na]^+$).

(E)-3-(3-(3,4-Dimethoxyphenyl)acryloyl)benzo[d]oxazol-2(3H)-one (FT124)

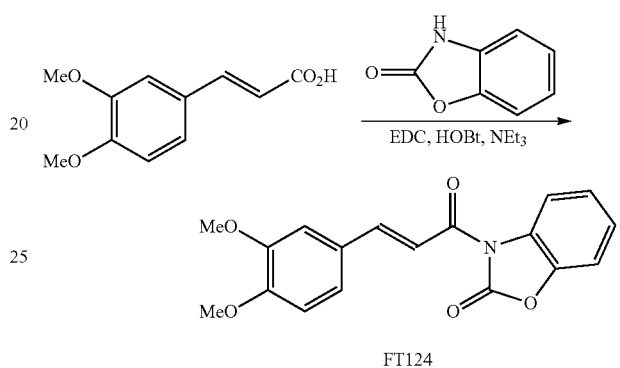

FT124

To a solution of (E)-3-(3,4-dimethoxyphenyl)acrylic acid (208 mg, 1.0 mmol) and benzo[d]oxazol-2(3H)-one (162 mg, 1.2 mmol) in DCM (10 mL) was added EDC.HCl (230 mg, 1.2 mmol), HOBt (196 mg, 1.2 mmol) and Et$_3$N (304 mg, 3.0 mmol). The mixture was stirred at room temperature overnight then diluted with water and extracted with DCM. The organic layer was dried over sodium sulfate and the solvent was removed under reduced pressure. The residue was purified by flash chromatography using petroleum ether/ethyl acetate 3:2 (v:v) to give (E)-3-(3-(3,4-d)acryloyl)benzo[d]oxazol-2(3H)-one (225 mg, 70%). $^1$H-NMR (400 MHz, DMSO-d$_6$) δ 3.84 (s, 6H), 7.09 (d, J=8.4 Hz, 1H), 7.31-7.38 (m, 4H), 7.44-7.46 (m, 1H), 7.76 (d, J=15:6 Hz, 1H), 7.95 (d, J=16 Hz, 1H), 8.03-8.06 (m, 1H), LC-MS (ES-API); rt 9.08 min; m/z calculated for $C_{18}H_{15}NO_5$ $[M+Na]^+$ 348.1, found 348.1.

(E)-4-(3-(3,4-Dimethoxyphenyl)acryloyl)-3,4-dihydroquinoxalin-2(1H)-one (FT125)

3,4-Dihydroquinoxalin-2(1H)-one

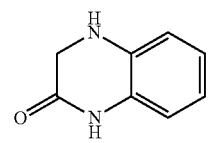 [SMILES: O=C1CNc2ccccc2N1]

To a solution of o-phenylenediamine (1.08 g, 10 mmol) in DMF (50 mL) was added Et$_3$N (2.9 mL, 21 mmol), and ethyl 2-bromoacetate (1.2 mL, 11 mmol). The reaction mixture was stirred at room temperature for 16 h, then at 80° C. for 3 h. The DMF was evaporated under reduced pressure and the reaction mixture partitioned between H$_2$O and EtOAc. The EtOAc layer was washed with sat. NaHCO$_3$, brine, and dried over Na$_2$SO$_4$. The solvent was evaporated under reduced pressure and the crude residue purified by flash chromatography eluting with petroleum ether/EtOAc (4/1) to give 3,4-dihydroquinoxalin-2(1H)-one (560 mg, 38%) as yellow solid. LC-MS (ES-API); rt 7.40 min; m/z calculated for C$_8$H$_8$N$_2$O [M+H]$^+$ 149.0, found 149.0.

(E)-4-(3-(3,4-Dimethoxyphenyl)acryloyl)-3,4-dihydroquinoxalin-2(1H)-one (FT125)

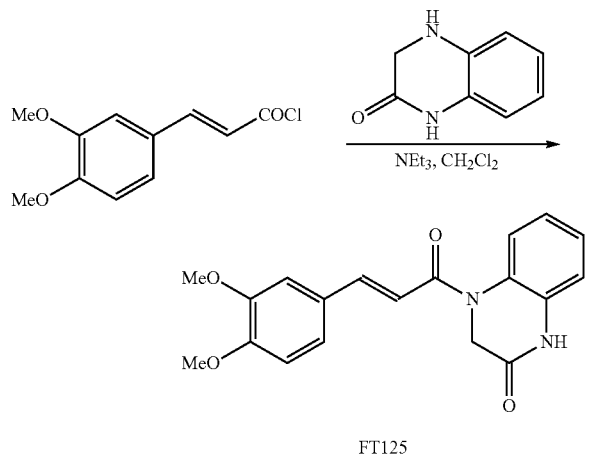

FT125

To a stirred solution of 3,4-dihydroquinoxalin-2(1H)-one (142 mg, 0.96 mmol) and triethylamine (0.16 mL, 1.14 mmol) in anhydrous THF (15 mL) at 0° C. was added a solution of (E)-3-(3,4-dimethoxyphenyl)acryloyl chloride in THF (2 mL) dropwise. The reaction mixture was allowed to warm to room temperature and stirred for 2 hours. The reaction was quenched by addition of 1N hydrochloric acid, and extracted with DCM. The combined organic phases were washed with brine, dried over sodium sulfate and concentrated under reduced pressure to afford the crude product which was purified by flash chromatography (hexane-EtOAc, 25:10) to give (E)-4-(3-(3,4-dimethoxyphenyl)acryloyl)-3,4-dihydroquinoxalin-2(1H)-one (160 mg, 47%). $^1$H-NMR (400 MHz, CDCl$_3$) δ 3.86 (s, 3H), 3.90 (s, 3H), 4.63 (br s, 2H), 6.71 (d, J=15.2 Hz, 1H), 6.85 (d, J=8.4 Hz, 1H), 6.94 (d, J=2.0 Hz, 1H), 7.02 (dd, J=7.6, 1.2 Hz, 1H), 7.07-7.13 (m, 2H), 7.22 (dd, J=7.6, 1.2 Hz, 1H), 7.28 (br d, J=8.0 Hz, 1H), 7.76 (d, J=15.6 Hz, 1H), 8.89 (s, 1H); LC-MS (ES-API); rt 8.14 min; m/z calculated for C$_{19}$H$_{18}$N$_2$O$_4$ [M+H]$^+$ 339.1, found 339.0.

2-(5,6-Dimethoxy-1H-indene-2-carboxamido)benzoic acid (FT126)

2-Iodo-4,5-dimethoxybenzaldehyde

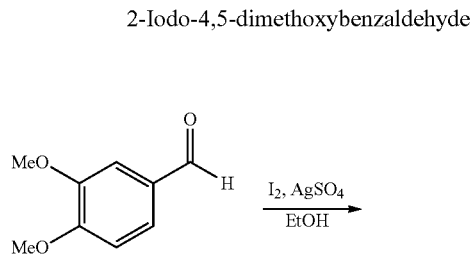

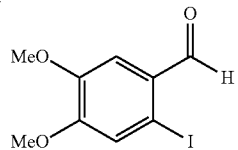

To a solution of 3,4-dimethoxybenzaldehyde (2.00 g, 12.0 mmol) in EtOH (100 mL) under nitrogen was added iodine (3.65 g, 14.4 mmol) and silver sulfate (4.49 g, 14.4 mmol) and the mixture was stirred for 3 hours at room temperature. The solvent was removed, water was added and the mixture was extracted with DCM. The organic extracts were washed with brine, dried over sodium sulfate and the solvent was removed under reduce pressure. The residue was purified by flash chromatography using petroleum ether/ethyl acetate 2:1 (v:v) as eluent to give 2-iodo-4,5-dimethoxybenzaldehyde (2.81 g, 80%). LC-MS (ES-API); rt 8.52 min; m/z calculated for C$_9$H$_9$IO$_3$ [M+H]$^+$ 293.0, found 293.0.

Methyl 5,6-dimethoxy-1H-indene-2-carboxylate

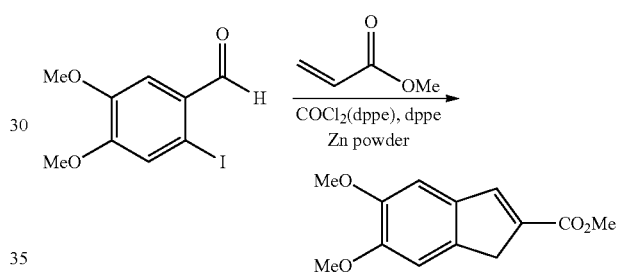

2-Iodo-4,5-dimethoxybenzaldehyde (292 mg, 1.0 mmol), CoCl$_2$ (dppe) complex (26.4 mg, 0.05 mmol), dppe (19.9 mg, 0.05 mmol) and zinc power (179.8 mg, 2.75 mmol) were placed in a vial, which was sealed with a septum and flushed several times with nitrogen. Acetonitrile (3 mL) and methyl acrylate (172 mg, 2.0 mmol) were then sequentially added and the mixture was heated at 80° C. overnight. Water was then added and the mixture was extracted with ethyl acetate. The organic extracts were concentrated under reduced pressure and the residue was purified by flash chromatography using petroleum ether/ethyl acetate 8:1 (v:v) as eluent to give methyl 5,6-dimethoxy-1H-indene-2-carboxylate (50 mg, 21%). LC-MS (ES-API); rt 7.89 min; m/z calculated for C$_{13}$H$_{14}$O$_4$ [M+H]$^+$ 235.1, found 235.1.

5,6-Dimethoxy-1H-indene-2-carboxylic acid

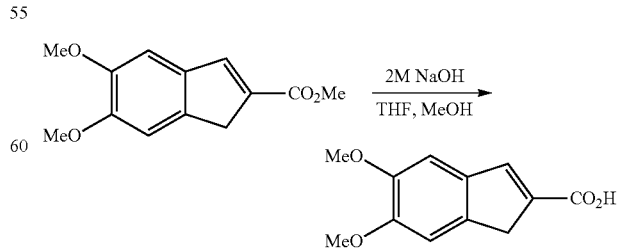

To a stirred solution of methyl 5,6-dimethoxy-1H-indene-2-carboxylate (330 mg, 1.41 mmol) in THF (8 mL) and MeOH (4 mL) was added 2 N NaOH solution (3.5 mL) dropwise at room temperature. The resulting mixture was stirred at room temperature for 2 hours and the reaction was quenched with 1N HCl solution. Then mixture was diluted with water and the resulting suspension was filtered and the solid was dried under vacuum to give 5,6-dimethoxy-1H-indene-2-carboxylic acid (150 mg, 48%). LC-MS (ES-API); rt 8.44 min; m/z calculated for $C_{12}H_{12}O_4$ [M−H]⁻ 219.1, found 219.1.

Methyl 2-(5,6-dimethoxy-1H-indene-2-carboxamido)benzoate

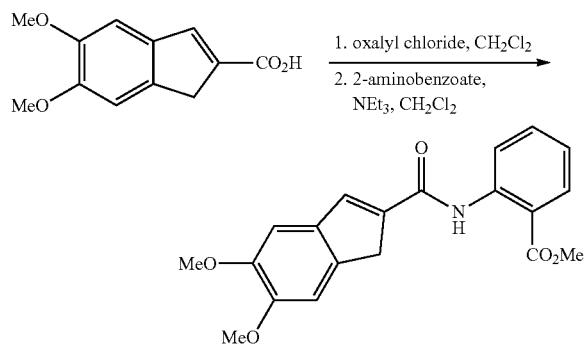

To a stirred mixture of 5,6-dimethoxy-1H-indene-2-carboxylic acid (230 mg, 1.05 mmol) and DMF (20 μL) in DCM (10 mL) was added oxalyl chloride (267 mg, 2.10 mmol) dropwise at room temperature. The resulting mixture was stirred for 2 hours then concentrated and dried under high vacuum. The resulting acid chloride was then taken up into DCM (10 mL) and added dropwise to a stirred mixture of methyl 2-aminobenzoate (174 mg, 1.16 mmol) and triethylamine (159.1 mg, 1.58 mmol) in DCM (10 mL) 0° C. The mixture was then stirred overnight at room temperature before adding water and extracting with DCM. The organic extracts were dried over sodium sulfate and the solvent was removed under reduced pressure. The residue was purified by silica gel chromatography with petroleum ether/ethyl acetate 5:1 (v:v) as eluent to give methyl 2-(5,6-dimethoxy-1H-indene-2-carboxamido)benzoate (140 mg, 38%). LC-MS (ES-API); rt 9.35 min; m/z calculated for $C_{20}H_{19}NO_5$ [M+H]⁺ 354.1, found 354.1.

2-(5,6-Dimethoxy-1H-indene-2-carboxamido)benzoic acid (FT126)

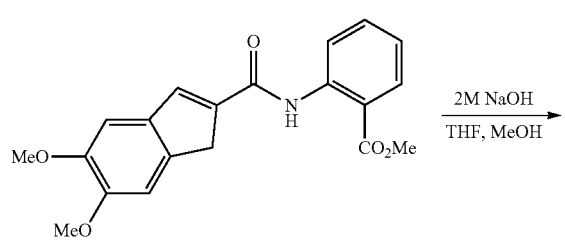

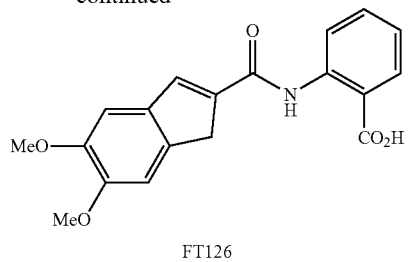

FT126

To a stirred solution of methyl 2-(5,6-dimethoxy-1H-indene-2-carboxamido)benzoate (120 mg, 0.34 mmol) in THF (6 mL) and MeOH (3 mL) was added 2 N NaOH solution (0.85 mL) dropwise. The resulting mixture was stirred at room temperature for 2 h, then quenched with 1N HCl solution and extracted with DCM. The organic extracts were washed with a saturated aqueous NaCl solution and dried over sodium sulfate. The solvent was then removed under reduced pressure to give 2-(5,6-dimethoxy-1H-indene-2-carboxamido)benzoic acid (100 mg, 87%). ¹H-NMR (400 MHz, DMSO-$d_6$) δ 3.72 (br s, 2H), 3.79 (s, 3H), 3.81 (s, 3H), 7.15 (m, 1H), 7.24 (s, 1H), 7.26 (s, 1H), 7.55-7.66 (m, 2H), 8.04 (dd, J=8.0, 1.6 Hz, 1H), 8.70 (dd, J=8.4, 1.2 Hz, 1H), 11.91 (s, 1H); LC-MS (ES-API); rt 9.23 min; m/z calculated for $C_{19}H_{17}NO_5$ [M−H]⁻ 338.1, found 338.1.

2-(5,6-Dimethoxy-1H-benzo[d]imidazole-2-carboxamido)benzoic acid (FT127)

Methyl 2-aminobenzoate

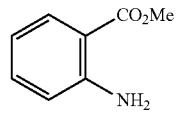

To a stirred solution of 2-aminobenzoic acid (2.0 g, 14.59 mmol) in MeOH (70 mL) at 0° C. was added $SOCl_2$ (7.4 g, 145.9 mmol) dropwise. The mixture was heated at reflux overnight and was then concentrated under reduced pressure. DCM and saturated aqueous $NaHCO_3$ were added and the aqueous phase extracted with DCM. The combined organic layers were washed with brine, dried over sodium sulfate and concentrated to afford methyl 2-aminobenzoate (2.05 g, 93%). LC-MS (ES-API); rt 8.46 min; m/z calculated for $C_8H_9NO_2$[M+H]⁺ 152.0, found 152.1.

Methyl 2-(2-chloroacetamido)benzoate

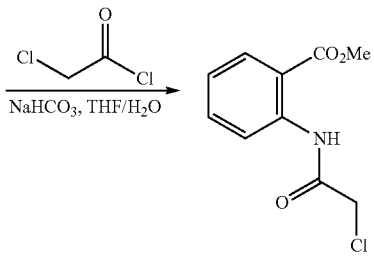

To a stirred solution of methyl 2-aminobenzoate (906 mg, 6.0 mmol) and NaHCO$_3$ (554.4 mg, 6.6 mmol) in THF (12 mL) and water (12 mL) at 0° C. was added 2-chloroacetyl chloride (806 mg, 7.2 mmol) dropwise. After 2 hours, the mixture was diluted with water and extracted with ethyl acetate. The organic layer was washed with brine, dried over sodium sulfate and concentrated under reduced pressure to afford the crude product. The residue was purified by flash chromatography to give methyl 2-(2-chloroacetamido)benzoate (1.31 g, 96%). LC-MS (ES-API); rt 8.65 min; m/z calculated for C$_{10}$H$_{10}$ClNO$_3$ [M+Na]$^+$ 250.0, found 250.0.

Methyl 2-(5,6-dimethoxy-1H-benzo[d]imidazole-2-carboxamido)benzoate

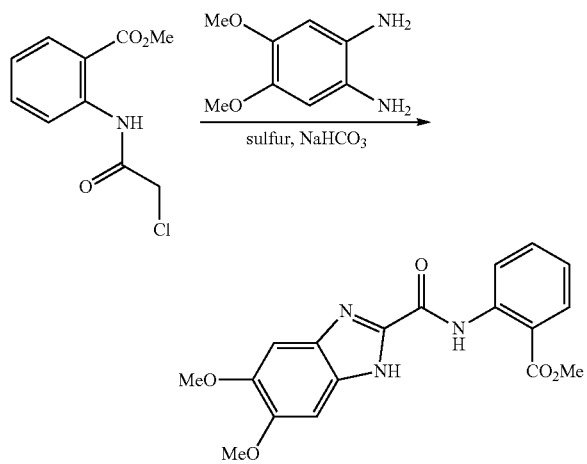

A mixture of 4,5-dimethoxybenzene-1,2-diamine (1.08 g, 4.5 mmol), NaHCO$_3$ (756 mg, 9.0 mmol) methyl 2-(2-chloroacetamido)benzoate (1.03 g, 4.5 mmol) and sulfur (216 mg, 6.75 mmol) in CH$_3$CN (27 mL) was stirred in a microwave reactor for 2 hours at 140° C. The mixture was concentrated and purified by flash column chromatography to give the desired methyl 2-(5,6-dimethoxy-1H-benzo[d]imidazole-2-carboxamido)benzoate (190 mg, 12%). LC-MS (ES-API); rt 9.12 min; m/z calculated for C$_{18}$H$_{17}$N$_3$O$_5$ [M+Na]$^+$ 378.1, found 378.1.

2-(5,6-Dimethoxy-1H-benzo[d]imidazole-2-carboxamido)benzoic acid

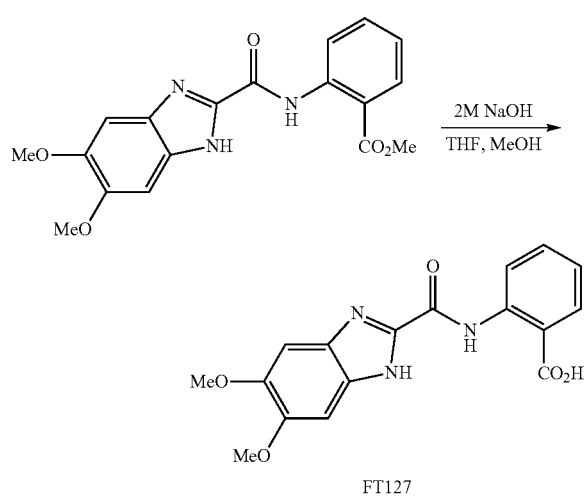

FT127

To a stirred solution of methyl 2-(5,6-dimethoxy-1H-benzo[d]imidazole-2-carboxamido)benzoate (200 mg, 0.56 mmol) in THF (10 mL) and MeOH (5 mL) was added 2N NaOH solution (1.4 mL) dropwise. The resulting mixture was stirred at room temperature for 2 hours. The reaction was quenched by addition of 1N HCl solution and extracted with DCM. The organic layer was washed with brine, dried over sodium sulfate and concentrated to give 2-(5,6-dimethoxy-1H-benzo[d]imidazole-2-carboxamido)benzoic acid (90 mg, 47.1%). $^1$H-NMR (400 MHz, DMSO-d$_6$) δ 3.82 (s, 6H), 6.97 (s, 1H), 7.13-7.34 (m, 2H), 7.64 (m, 1H), 8.08 (d, J=9.6 Hz, 1H), 8.78 (d, J=7.6 Hz; 1H), 12.90 (s, 1H), 13.27 (s, 1H); LC-MS (ES-API); rt 8.74 min; m/z calculated for C$_{17}$H$_{15}$N$_3$O$_5$ [M–H]$^-$ 340.1, found 340.1.

2-(1,1-Dioxo-5,6-dimethoxybenzo[b]thiophene-2-carboxamido)benzoic acid (FT128)

Methyl 5,6-dimethoxybenzo[b]thiophene-2-carboxylate

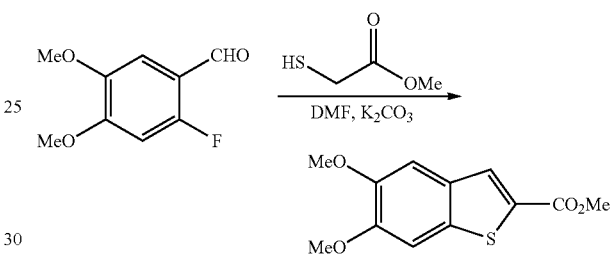

To a stirred solution of 2-fluoro-4,5-dimethoxybenzaldehyde (1.10 g, 6 mmol) in DMF (50 mL) was added methyl 2-mercaptoacetate (0.58 mL, 6.6 mmol) and potassium carbonate (2.48 g, 18 mmol). The resulting mixture was then heated at 60° C. for 15 hours. The DMF was removed via rotary evaporation and the residue was diluted with water and extracted with DCM. The organic phase was dried over sodium sulfate and the solvent was removed under reduced pressure to afford methyl 5,6-dimethoxybenzo[b]thiophene-2-carboxylate as a light yellow solid (1.0 g, 67%). LC-MS (ES-API); rt 8.48 min; m/z calculated for C$_{12}$H$_{12}$O$_4$S [M+Na]$^+$ 275.0, found 275.0.

5,6-Dimethoxybenzo[b]thiophene-2-carboxylic acid

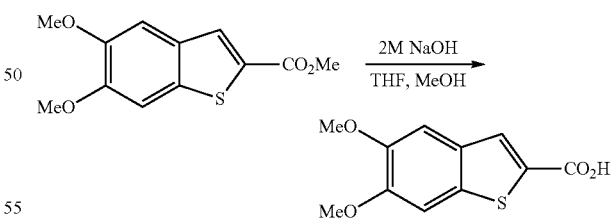

To a stirred solution of methyl 5,6-dimethoxybenzo[b]thiophene-2-carboxylate (1.0 g, 4 mmol) in MeOH (20 mL) and THF (10 mL) was added 2N NaOH (10 mL) dropwise at room temperature. The resulting mixture was stirred at room temperature for 2 hours before adjusting the pH value to 3 with 1 N HCl and diluting with water. The resulting suspension was filtered and the solid was dried under vacuum to afford 5,6-dimethoxybenzo[b]thiophene-2-carboxylic acid as a white solid (890 mg, 94%). LC-MS (ES-API); rt 8.17 min; m/z calculated for C$_{11}$H$_{10}$O$_4$S [M+Na]$^+$ 261.0, found 260.9.

101

Methyl 2-(5,6-dimethoxybenzo[b]thiophene-2-carboxamido)benzoate

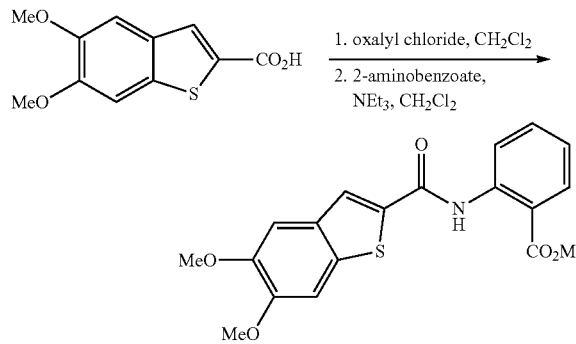

To a stirred solution of 5,6-dimethoxybenzo[b]thiophene-2-carboxylic acid (714 mg, 3 mmol) and DMF (20 μl) in anhydrous DCM (20 mL) was added oxalyl chloride (0.5 mL, 6 mmol) dropwise at 0° C. The mixture was then allowed to warm to room temperature and stirring was continued until the acid was consumed completely (about 1 h). The solvent was removed under reduced pressure and the crude 5,6-dimethoxybenzo[b]thiophene-2-carbonyl chloride was used directly in the next step. To a stirred solution of methyl 2-aminobenzoate (500 mg, 3.3 mmol) and $Et_3N$ (1.25 mL, 9 mmol) in anhydrous DCM (20 mL) was added 5,6-dimethoxybenzo[b]thiophene-2-carbonyl chloride in anhydrous DCM (2 mL) dropwise at 0° C. The resulting mixture was stirred at room temperature overnight. The reaction was quenched with water and extracted with DCM. The organic extract was dried over sodium sulfate, the solvent was removed under reduced pressure and the crude product was purified by re-crystallization from EtOH to give methyl 2-(5,6-dimethoxybenzo[b]thiophene-2-carboxamido)benzoate as a white solid (650 mg, 55%). LC-MS (ES-API); rt 9.38 min; m/z calculated for $C_{19}H_{17}NO_5S$ [M+H]$^+$ 372.1, found 372.1.

2-(5,6-Dimethoxybenzo[b]thiophene-2-carboxamido)benzoic acid

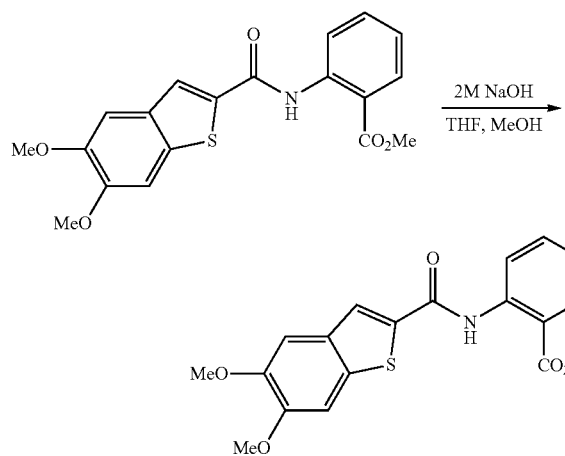

To a stirred solution of methyl 2-(5,6-dimethoxybenzo[b]thiophene-2-carboxamido)benzoate (650 mg, 1.75 mmol) in MeOH (9 mL) and THF (20 mL) was added 2N NaOH (9 mL) dropwise at room temperature. The resulting solution was stirred at room temperature for 2 hours. The reaction was quenched with 1N HCl and diluted with water. The resulting suspension was filtered and the solid was dried under vacuum to afford 2-(5,6-dimethoxybenzo[b]thiophene-2-carboxamido)benzoic acid (550 mg, 88%). LC-MS (ES-API); rt 9.22 min; m/z calculated for $C_{18}H_{15}NO_5S$ [M+Na]$^+$ 380.1, found 380.0.

2-(1,1-Dioxo-5,6-dimethoxybenzo[b]thiophene-2-carboxamido)benzoic acid

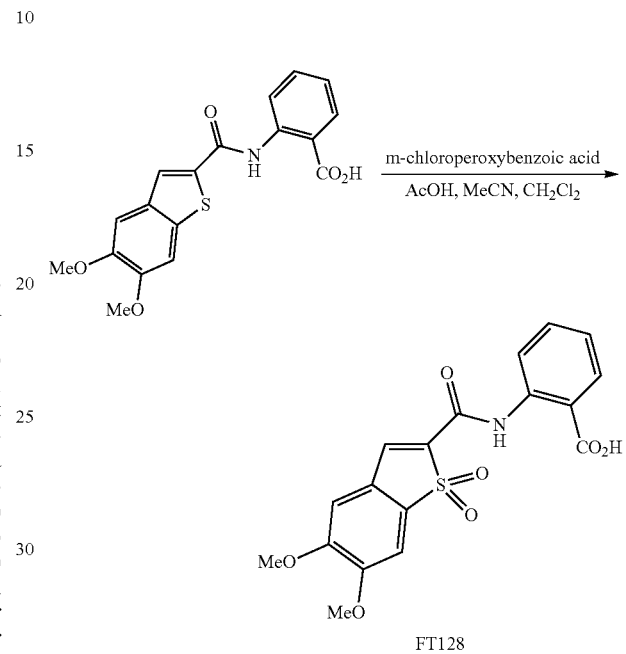

FT128

To a stirred solution of 2-(5,6-dimethoxybenzo[b]thiophene-2-carboxamido)benzoic acid (500 mg, 1.4 mmol) in $CH_3COOH$ (100 mL), $CH_3CN$ (50 mL) and DCM (50 mL) was added m-Chloroperoxybenzoic acid (1.2 g, 7 mmol) at room temperature. The resulting solution was stirred at room temperature for 48 hours until the starting material was consumed completely by TLC analysis. The reaction was quenched with water and extracted with DCM. The combined organic phase was washed with water, brine and dried over sodium sulfate. The solvent was removed under reduced pressure and the residue was purified by flash column using DCM/MeOH (from 30:1 to 10:1) as eluent. Further purification by re-crystallization from $CH_3CN$ provided 2-(1,1-dioxo-5,6-dimethoxybenzo[b]thiophene-2-carboxamido)benzoic acid (220 mg, 40%). $^1$H-NMR (400 MHz, DMSO-$d_6$) δ 3.89 (s, 3H), 3.92 (s, 3H), 7.26 (app t, J=7.6 Hz, 1H), 7.48 (s, 1H), 7.61 (s, 1H), 7.67 (m, 1H), 8.05 (dd, J=8.0, 1.2 Hz, 1H), 8.14 (s, 1H), 8.47 (d, J=8.4 Hz, 1H), 11.87 (s, 1H); LC-MS (ES-API); rt 8.91 min; m/z calculated for $C_{18}H_{15}NO_7S$ [M+H]$^+$ 390.1, found 390.1.

2-(6,7-Dimethoxy-1,2-dihydronaphthalene-3-carboxamido)benzoic acid (FT129)

6,7-Dimethoxy-1,2,3,4-tetrahydronaphthalen-1-ol

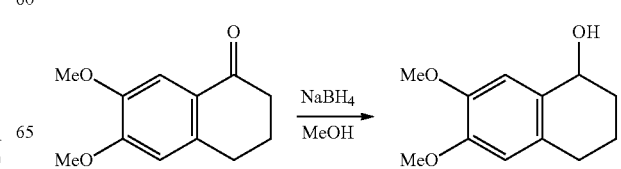

To a stirred solution of 6,7-dimethoxy-3,4-dihydronaphthalen-1(2H)-one (3.09 g, mmol) in MeOH (50 mL) was added NaBH₄ (680 mg, 18 mmol) portion wise over 0.5 hour. The resulting mixture was stirred at room temperature overnight. The reaction was quenched with 1N HCl, diluted with water and extracted with DCM. The combined organic phase was washed with brine, dried over sodium sulfate and the solvent was removed under reduced pressure to afford 6,7-dimethoxy-1,2,3,4-tetrahydronaphthalen-1-ol as a yellow oil (2.9 g, 93%). LC-MS (ES-API); rt 7.96 min; m/z calculated for $C_{12}H_{16}O_3$ [M+Na]⁺ 231.1, found 231.1.

6,7-Dimethoxy-3,4-dihydronaphthalene-2-carbaldehyde

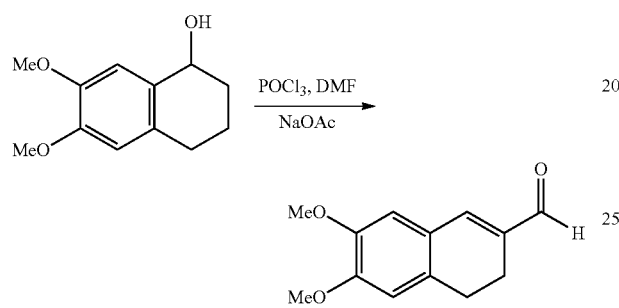

A solution of 6,7-dimethoxy-1,2,3,4-tetrahydronaphthalen-1-ol (208 mg, 1 mmol) in dry DMF (5 mL) was cooled in an ice bath and phosphoryl chloride (0.2 mL, 2.3 mmol) was added dropwise. The reaction mixture was heated at 90° C. for 3 hours, then cooled and treated with a cold saturated aqueous solution of sodium acetate (2 mL) and stirred at room temperature for 10 min. Water was added and the mixture was extracted with DCM. The combined organic phase was washed with brine and dried over sodium sulfate. The solvent was then removed under reduced pressure to afford 6,7-dimethoxy-3,4-dihydronaphthalene-2-carbaldehyde as white solid (160 mg, 46%). LC-MS (ES-API); rt 8.23 min; m/z calculated for $C_{13}H_{14}O_3$ [M+H]⁺ 219.1, found 219.0.

6,7-Dimethoxy-3,4-dihydronaphthalene-2-carboxylic acid

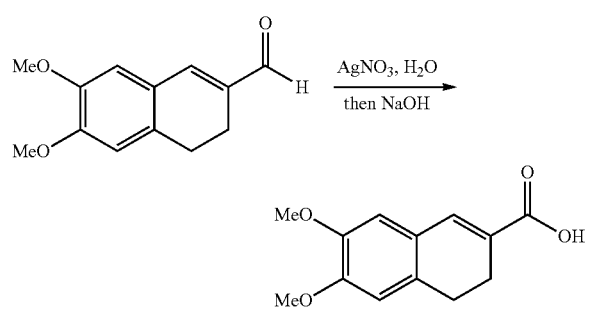

A mixture of 6,7-dimethoxy-3,4-dihydronaphthalene-2-carbaldehyde (2.2 g, 10 mmol) in EtOH (30 mL) was treated with a solution of silver nitrate (5.0 g, 30 mmol) in water (16 mL). A solution of NaOH (6.0 g, 150 mmol) in water (50 mL) was then added with continuous stirring and the resulting mixture was stirred at room temperature overnight. The reaction mixture was then extracted with DCM and combined organic phase was washed with brine and dried over sodium sulfate. The solvent was removed under reduced pressure and the residue was purified by flash column using petroleum ether/ethyl acetate (from 6:1 to 3:1, v:v) as the eluent to give 6,7-dimethoxy-3,4-dihydronaphthalene-2-carboxylic acid (1.8 g, 77%). LC-MS (ES-API); rt 8.23 min; m/z calculated for $C_{13}H_{14}O_4$ [M+H]⁺ 235.1, found 235.0.

Methyl 2-(6,7-dimethoxy-1,2-dihydronaphthalene-3-carboxamido)benzoate

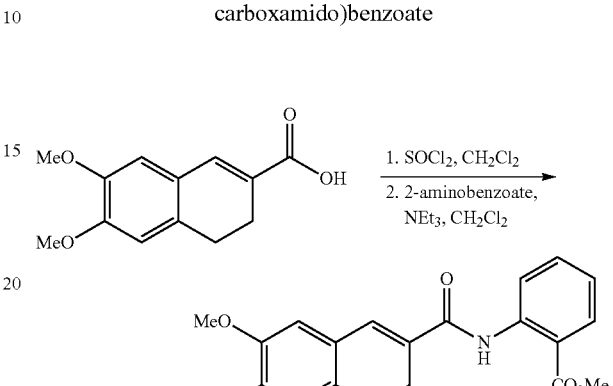

A mixture of 6,7-dimethoxy-3,4-dihydronaphthalene-2-carboxylic acid (476 mg, 2 mmol) and SOCl₂ (1.5 mL, 20 mmol) in toluene (20 mL) was heated at 50° C. for 1 hour. The solvent was then removed under reduced pressure to give 6,7-dimethoxy-3,4-dihydronaphthalene-2-carbonyl chloride which was used directly in the next step without further purification. To a stirred solution of methyl 2-aminobenzoate (332 mg, 2.2 mmol) and Et₃N (0.8 mL, 6 mmol) in anhydrous DCM (20 mL) was added 6,7-dimethoxy-3,4-dihydronaphthalene-2-carbonyl chloride in anhydrous DCM (2 mL) dropwise at 0° C. The resulting mixture was stirred at room temperature overnight. The reaction was quenched with water and extracted with DCM. The combined organic phase was dried over sodium sulfate, the solvent was removed under reduced pressure and the residue was purified by flash column, eluting with petroleum ether/ethyl acetate (10:1) to give methyl 2-(6,7-dimethoxy-1,2-dihydronaphthalene-3-carboxamido)benzoate (330 mg, 45%). LC-MS (ES-API); rt 9.27 min; m/z calculated for $C_{21}H_{21}NO_5$ [M+Na]⁺ 390.1, found 390.1.

2-(6,7-Dimethoxy-1,2-dihydronaphthalene-3-carboxamido)benzoic acid (FT129)

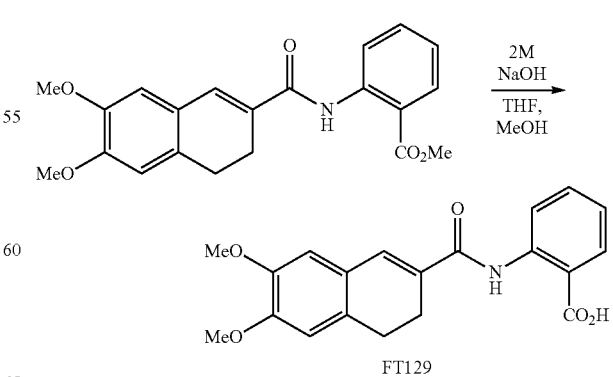

FT129

To a stirred solution of methyl 2-(6,7-dimethoxy-3,4-dihydronaphthalene-2-carboxamido)benzoate (440 mg, 1.2 mmol) in MeOH (6 mL) and THF (3 mL) was added 2N NaOH (3 mL) dropwise at room temperature. The resulting solution was stirred at room temperature for 2 hours, then quenched with 1N HCl and diluted with water. The resulting suspension was filtered and the solid was dried under vacuum to give 2-(6,7-dimethoxy-1,2-dihydronaphthalene-3-carboxamido)benzoic acid (350 mg, 83%). $^1$H-NMR (400 MHz, DMSO-d$_6$) δ 2.59 (t, J=8.4 Hz, 2H), 2.83 (t, J=8.4 Hz, 2H), 3.75 (s, 3H), 3.79 (s, 3H), 6.90 (s, 1H), 6.97 (s, 1H), 7.15 (app t, J=7.6 Hz, 1H), 7.39 (s, 1H), 7.62 (m, 1H), 8.03 (dd, J=8.0, 1.6 Hz, 1H), 8.69 (d, J=8.4 Hz, 1H), 11.89 (s, 1H); LC-MS (ES-API); rt 9.22 min; m/z calculated for C$_{20}$H$_{19}$NO$_5$ [M+Na]$^+$ 376.1, found 376.1.

2-(6,7-Dimethoxy-1,2,3,4-tetrahydronaphthalene-3-carboxamido)benzoic acid (FT130)

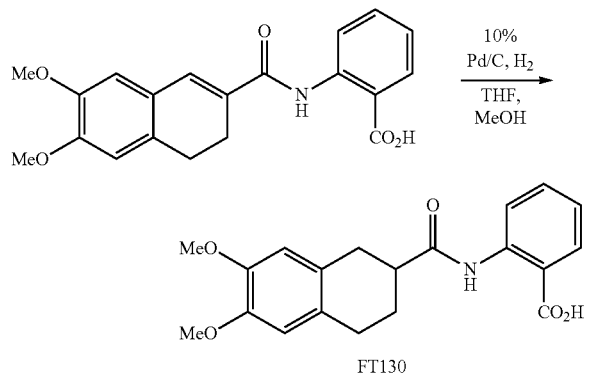

A mixture of 2-(6,7-dimethoxy-3,4-dihydronaphthalene-2-carboxamido)benzoic acid (350 mg, 1 mmol) and 10% Pd/C (35 mg) in MeOH (50 mL) and THF (50 mL) was stirred at room temperature under H$_2$ overnight. The mixture was filtered and the filtrate was concentrated under reduced pressure to afford 2-(6,7-dimethoxy-1,2,3,4-tetrahydronaphthalene-3-carboxamido)benzoic acid (250 mg, 71%). $^1$H-NMR (400 MHz, DMSO-d$_6$) δ 1.70-1.85 (m, 1H), 2.10-2.21 (m, 1H), 2.64-2.82 (m, 3H), 2.82-3.00 (m, 2H), 3.71 (s, 6H), 6.66 (s, 1H), 6.68 (s, 1H), 7.16 (app t, J=7.6 Hz, 1H), 7.60 (app t, J=8.0 Hz, 1H), 8.00 (d, J=7.2 Hz, 1H), 8.53 (d, J=8.4 Hz, 1H), 11.32 (s, 1H); LC-MS (ES-API); rt 8.96 min; m/z calculated for C$_{20}$H$_{21}$NO$_5$ [M+H]$^+$ 356.1, found 356.1.

(Z)-2-(2-(6,7-Dimethoxy-1-oxo-2,3-dihydroisoquinolin-4(1H)-ylidene)acetamido)benzoic acid (FT131)

2-Iodo-4,5-dimethoxybenzoic acid

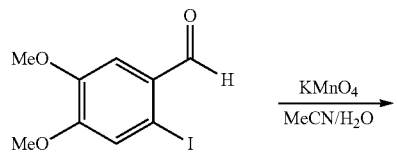

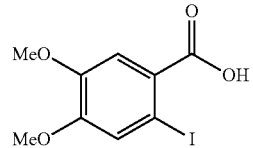

To a stirred solution of 2-iodo-4,5-dimethoxybenzaldehyde (1.0 g, 3.42 mmol) in CH$_3$CN (25 mL) was added a solution of KMnO$_4$ (0.76 g, 4.79 mmol) in water (15 mL) dropwise at 0° C. The resulting mixture was stirred at room temperature overnight. After the reaction was complete, the pH was adjusted to <7 with 1N HCl. The mixture was extracted with DCM and the organic layers combined, washed with brine, dried over sodium sulfate, and evaporated to give 2-Iodo-4,5-dimethoxybenzoic acid (0.89 g, 85%).

Ethyl 2-(2-iodo-4,5-dimethoxybenzamido)acetate

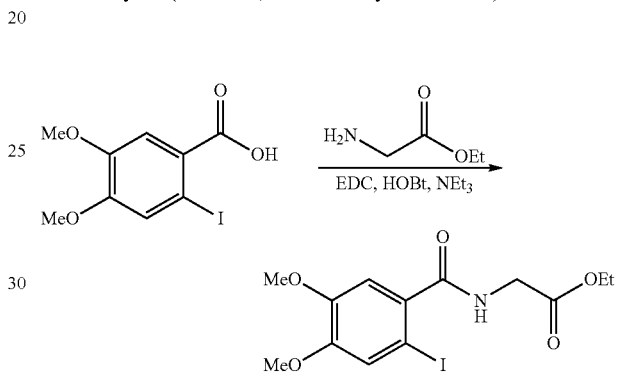

To a stirred solution of 2-iodo-4,5-dimethoxybenzoic acid (24.6 g, 80 mmol), ethyl 2-aminoacetate hydrochloride (11 g, 88 mmol), EDCl (17 g, 88 mmol) and HOBt (14 g, 88 mmol) in dry DCM (500 mL) was added Et$_3$N (55 mL, 400 mmol) dropwise at rt. The resulting mixture was stirred at room temperature overnight then the reaction was quenched with water, and thoroughly extracted with DCM. The combined organic phases were washed with brine and dried over sodium sulfate. The solvent was removed under reduced pressure and the residue was purified by flash chromatography using petroleum ether/ethyl acetate 3:1 (v:v) as eluent to give ethyl 2-(2-iodo-4,5-dimethoxybenzamido)acetate (29 g, 95%).

N-(2-Hydroxyethyl)-2-iodo-4,5-dimethoxybenzamide

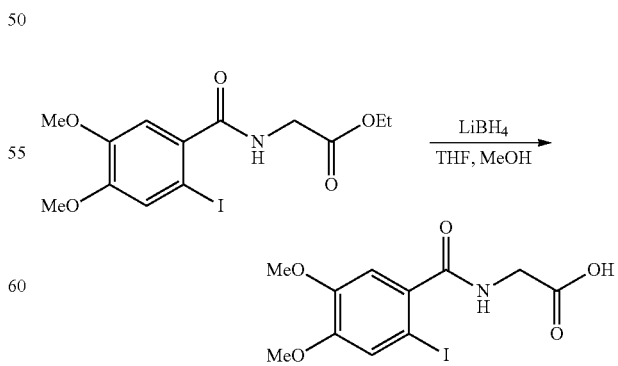

LiBH$_4$ (63 mg, 3 mmol) was added to a stirred solution of ethyl 2-(2-iodo-4,5-dimethoxybenzamido)acetate (379 mg, 1 mmol) in THF (2 mL) at −10° C. The reaction was stirred for 5 min then methanol (0.22 mL) was added dropwise. The reaction mixture was warmed to room temperature, stirred for 30 minutes and quenched by addition of water. The THF was removed under reduced pressure and the aqueous residue was thoroughly extracted with DCM. The combined organic phases were washed with brine, dried over sodium sulphate and evaporated to give the crude product which was purified by re-crystallization from EtOAc and hexane to give N-(2-hydroxyethyl)-2-iodo-4,5-dimethoxybenzamide (280 mg, 80%) LC-MS (ES-API); rt 7.60 min; m/z calculated for $C_{11}H_{14}NO_4$ [M+H]$^+$ 352.0, found 352.0.

(Z)-Ethyl 4-(2-iodo-4,5-dimethoxybenzamido)but-2-enoate

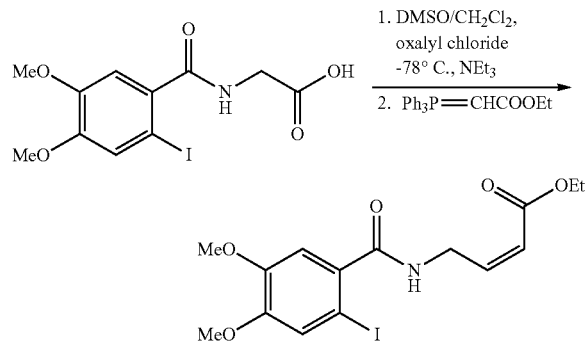

A solution of dry DMSO (0.453 mL, 6.4 mmol) in DCM (2 mL) was added dropwise to a solution of oxalyl chloride (0.338 mL, 4 mmol) in DCM (5 mL) at −78° C. The reaction was stirred for 30 min at −78° C. then a solution of N-(2-hydroxyethyl)-2-iodo-4,5-dimethoxybenzamide (702 mg, 2 mmol) in DCM (3 mL) was added via cannula. The mixture was stirred at −78° C. for 1 hour then dry Et$_3$N (1.7 mL, 12 mmol) was added slowly. Stirring was continued at −78° C. for 1 hour by which time the formation of the aldehyde was complete (monitored by TLC). Solid Ph$_3$P═CHCOOEt (1.0 g, 3 mmol) was then added and the reaction was allowed to warm slowly to room temperature overnight. The solvent was removed under reduced pressure and the crude product was purified by flash column using petroleum ether/ethyl acetate (from 6:1 to 3:1) as eluent to give (Z)-ethyl 4-(2-iodo-4,5-dimethoxybenzamido)but-2-enoate (280 mg, 34%). LC-MS (ES-API); rt 8.46 min; m/z calculated for $C_{15}H_{18}INO_5$ [M+H]$^+$ 420.0, found 420.0.

(Z)-Ethyl 2-(6,7-dimethoxy-1-oxo-2,3-dihydroiso-quinolin-4(1H)-ylidene)acetate

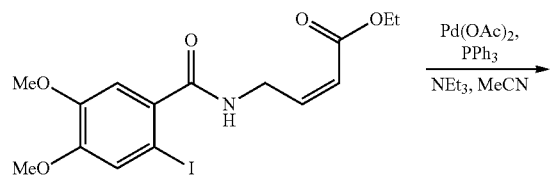

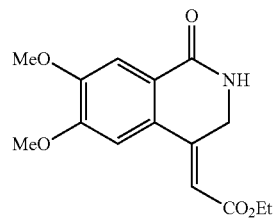

A stirred solution of Pd(OAc)$_2$ (16 mg, 0.07 mmol), PPh$_3$ (61 mg, 0.23 mmol), Et$_3$N (0.58 mL, 4.2 mmol) and (Z)-ethyl 4-(2-iodo-4,5-dimethoxybenzamido)but-2-enoate (860 mg, 2.1 mmol) in dry CH$_3$CN (20 mL) was heated at 70° C. overnight under an argon atmosphere. The reaction was allowed to cool to room temperature and then concentrated under reduced pressure. The residue was purified by flash chromatography using DCM/MeOH 100:1 (v:v) as eluent to give (Z)-ethyl 2-(6,7-dimethoxy-1-oxo-2,3-dihydroiso-quinolin-4(1H)-ylidene)acetate (510 mg, 83%). LC-MS (ES-API); rt 7.56 min; m/z calculated for $C_{15}H_{17}NO_5$ [M+H]$^+$ 292.1, found 292.1.

(Z)-2-(6,7-Dimethoxy-1-oxo-2,3-dihydroisoquino-lin-4(1H)-ylidene)acetic acid

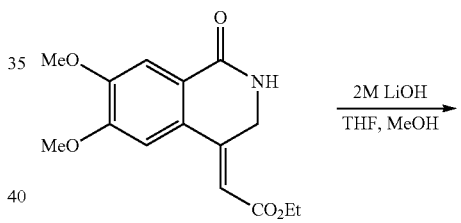

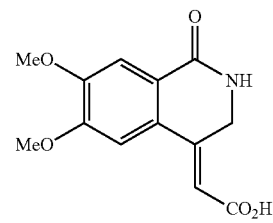

To a stirred solution of (Z)-ethyl 2-(6,7-dimethoxy-1-oxo-2,3-dihydroisoquinolin-4(1H)-ylidene)acetate (1.45 g, 5 mmol) in MeOH (20 mL) and THF (40 mL) was added 2N LiOH (5 mL) dropwise at room temperature and the resulting mixture was stirred at room temperature overnight. The reaction was quenched by addition of 1N HCl and the solvents were removed under reduced pressure. The mixture was diluted with water and cooled and the precipitate collected by filtration to afford (Z)-2-(6,7-dimethoxy-1-oxo-2,3-dihydroisoquinolin-4(1H)-ylidene)acetic acid (1.0 g, 77%). LC-MS (ES-API); rt 7.21 min; m/z calculated for $C_{13}H_{13}NO_5$ [M−H]$^-$ 262.0, found 262.1.

(Z)-Methyl 2-(2-(6,7-dimethoxy-1-oxo-2,3-dihydroisoquinolin-4(1H)-ylidene)acetamido)benzoate

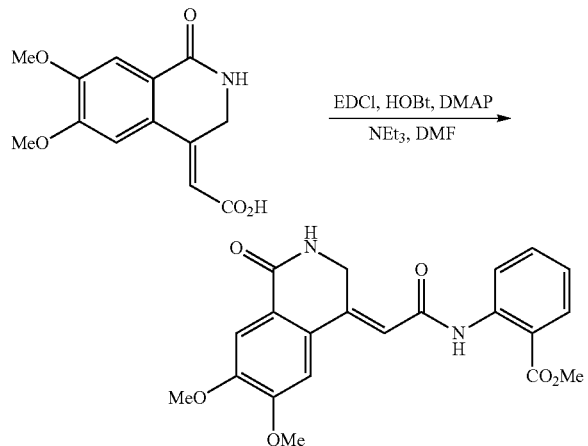

To a stirred solution of (Z)-2-(2-(6,7-dimethoxy-1-oxo-2,3-dihydroisoquinolin-4(1H)-ylidene)acetic acid (789 mg, 3 mmol), methyl 2-aminobenzoate (544 mg, 3.6 mmol), HOBt (587 mg, 3.6 mmol), EDCl (688 mg, 3.6 mmol) and DMAP (439 mg, 3.6 mmol) in dry DMF (30 mL) was added Et$_3$N (2 mL, 15 mmol) dropwise at room temperature. The resulting mixture was stirred at room temperature overnight then the reaction was quenched with water and extracted with DCM. The combined organic phases were washed with brine, dried over sodium sulfate and evaporated to give the crude product which was purified by flash chromatography using DCM/MeOH 40:1 (v:v) as eluent to give (Z)-methyl 2-(2-(6,7-dimethoxy-1-oxo-2,3-dihydroisoquinolin-4(1H)-ylidene)acetamido)benzoate (280 mg, 80%) LC-MS (ES-API); rt 8.39 min; m/z calculated for C$_{21}$H$_{20}$N$_2$O$_6$ [M+Na]$^+$ 419.1, found 419.1.

(Z)-2-(2-(6,7-Dimethoxy-1-oxo-2,3-dihydroisoquinolin-4(1H)-ylidene)acetamido)benzoic acid (FT131)

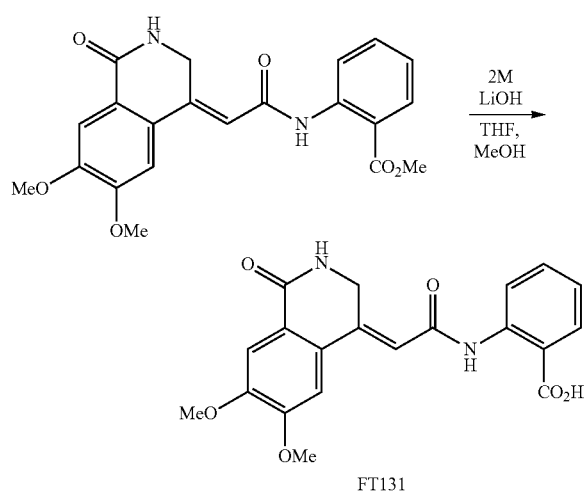

To a stirred solution of (Z)-methyl 2-(2-(6,7-dimethoxy-1-oxo-2,3-dihydroisoquinolin-4(1H)-ylidene)acetamido)benzoate (140 mg, 0.35 mmol) in MeOH (4 mL) and THF (8 mL) was added 2N LiOH (0.7 mL) dropwise at room temperature. The resulting mixture was stirred at room temperature overnight then the reaction was quenched by addition of 1N HCl and the solvent was removed under reduced pressure. The mixture was diluted with water, cooled and the precipitate collected by filtration to afford (Z)-2-(2-(6,7-dimethoxy-1-oxo-2,3-dihydroisoquinolin-4(1H)-ylidene)acetamido)benzoic acid (125 mg, 93%). $^1$H-NMR (400 MHz, DMSO-d$_6$) δ 3.80, (s, 3H), 3.84 (s, 2H), 3.85 (s, 3H), 7.00 (s, 1H), 7.10 (m, 1H), 7.22 (d, J=6.0 Hz, 1H), 7.56 (m, 1H), 7.61 (s, 1H), 7.90 (dd, J=8.0, 1.6 Hz, 1H), 8.57 (dd, J=8.4, 0.8 Hz, 1H), 11.38 (d, J=5.6 Hz, 1H), 13.54 (br s, 1H); LC-MS (ES-API); rt 8.27 min; m/z calculated for C$_{20}$H$_{18}$N$_2$O$_6$[M+H]$^+$ 383.1, found 383.1.

(E)-2-(3,4-Dimethoxystyryl)benzo[d]oxazole-4-carboxylic acid (FT132)

Methyl 2-amino-3-hydroxybenzoate

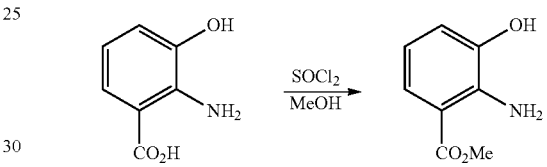

To a stirred solution of 2-amino-3-hydroxybenzoic acid (1.22 g, 8.0 mmol) in MeOH (80 mL) was added SOCl$_2$ (9.52 g, 80.0 mmol) dropwise at 0° C. The mixture was then heated at reflux overnight. Most of the methanol was removed and the residue was partitioned between DCM and saturated aqueous NaHCO$_3$. The organic phase was washed with brine, dried over sodium sulfate and the solvent was removed under reduced pressure to give methyl 2-amino-3-hydroxybenzoate (1.27 g, 95%). LC-MS (ES-API); rt 8.09 min; m/z calculated for C$_8$H$_9$NO$_3$ [M+H]$^+$ 168.1, found 168.1.

Methyl 2-methylbenzo[d]oxazole-4-carboxylate

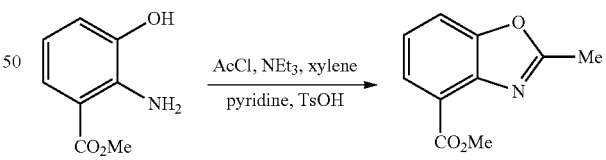

A solution of methyl 2-amino-3-hydroxybenzoate (167 mg, 1.0 mmol), acetyl chloride (86 mg, 1.1 mmol) and triethylamine (101 mg, 1.1 mmol) in xylene (10 mL) was stirred at 0° C. for 2 h. Pyridine (20 mg, 0.25 mmol) and TsOH (43 mg, 0.25 mmol) were then added and the mixture was heated at reflux overnight. The mixture was then cooled to room temperature, diluted with water and extracted with ethyl acetate. The combined organic extracts were washed with water, brine, then dried over sodium sulfate and the solvent was removed under reduced pressure. The residue was purified by flash chromatography using petroleum ether/ethyl acetate 5:1 (v:v) as eluent to give methyl 2-methylbenzo[d]

oxazole-4-carboxylate (151 mg, 79%). LC-MS (ES-API); rt 8.08 min; m/z calculated for $C_{10}H_9NO_3$ [M+H]$^+$ 192.1, found 192.1.

(E)-Methyl 2-(3,4-dimethoxystyryl)benzo[d]oxazole-4-carboxylate

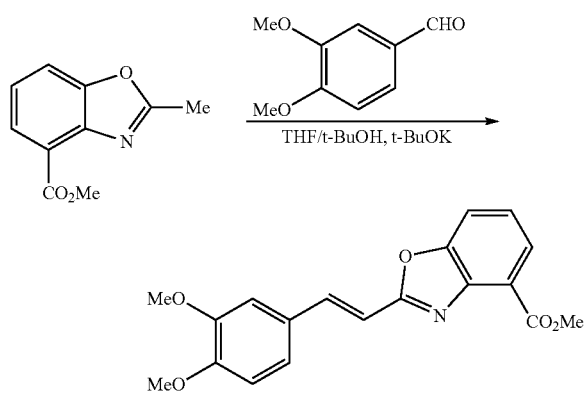

A solution of methyl 2-methylbenzo[d]oxazole-4-carboxylate (0.63 g, 4.12 mmol) and 3,4-dimethoxybenzaldehyde (0.68 g, 4.12 mmol) in THF (25 mL) and t-BuOH (5 mL) was cooled to −50° C. under nitrogen and treated with a solution of t-BuOK in THF (1.0 mol/L, 4.94 mL, 4.94 mmol) at such a rate that the internal reaction temperature did not exceed −46° C. After 2 hours at −50° C., the cooling bath was removed and the mixture was stirred at room temperature for 12 h in the dark. Water was added and the mixture was made slightly acidic by addition of a 1N HCl solution then extracted with DCM. The organic layers were combined, washed with water and brine then dried over sodium sulfate and the solvent was removed under reduced pressure. The residue was purified by flash chromatography using petroleum ether: ethyl acetate 2:1 (v:v) as eluent to give (E)-methyl 2-(3,4-dimethoxystyryl)benzo[d]oxazole-4-carboxylate (0.30 g, 27%). LC-MS (ES-API); rt 9.25 min; m/z calculated for $C_{19}H_{17}NO_5$ [M+H]$^+$ 340.1, found 340.1.

(E)-2-(3,4-Dimethoxystyryl)benzo[d]oxazole-4-carboxylic acid (FT132)

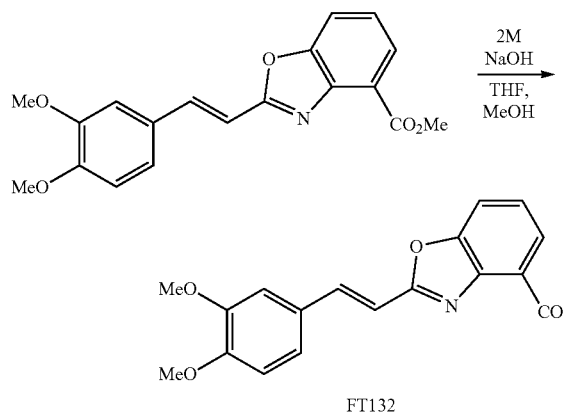

To a stirred solution of (E)-methyl 2-(3,4-dimethoxystyryl) benzo[d]oxazole-4-carboxylate (240 mg, 0.71 mmol) in THF (10 mL) and MeOH (5 mL) was added 2 N NaOH solution (1.77 mL) dropwise at room temperature. The resulting mixture was stirred at room temperature for two hours then quenched with a 1N HCl solution. The mixture was then extracted with DCM and the organic phase was washed with saturated aqueous NaCl solution and dried over sodium sulfate. The solvent was then removed under reduced pressure to give (E)-2-(3,4-Dimethoxystyryl)benzo[d]oxazole-4-carboxylic acid (170 mg, 74%). $^1$H-NMR (400 MHz, DMSO-$d_6$) δ 3.81 (s, 3H), 3.85 (s, 3H), 7.03 (d, J=8.0 Hz, 1H), 7.33-7.39 (m, 2H), 7.46 (app t, J=8.0 Hz, 1H), 7.50 (d, J=2.0 Hz, 1H), 7.80 (d, J=16.0 Hz, 1H), 7.87 (dd, J=8.0, 1.2 Hz, 1H), 7.93 (dd, J=8.0, 1.2 Hz, 1H); LC-MS (ES-API): rt 8.88 min; m/z calculated for $C_{18}H_{15}NO_5$ [M−H]$^-$ 324.1, found 324.1.

1097 Rat Mesangial Cells

A well-characterised cloned rat mesangial cell line (Kakizaki Y, Kraft N, Atkins R C: Differential control of mesangial cell proliferation by interferon-gamma. Clin Exp Immunol 85:157-163, 1991) was cultured in DMEM (5 mM glucose) with 5% FBS, 100 U/mL penicillin, and 100 ug/mL streptomycin in humidified 5% CO2 atmosphere at 37 C. Cells were used up to passage 40.

Proline Incorporation Assay

Cells were plated into 24-well culture dishes in DMEM/5% FBS and allowed to adhere overnight. The subconfluent cells were then starved overnight in DMEM/0.1% FBS and 150 uM L-ascorbic acid, prior to pre-treatment with or without FibroTech compounds for 4 hours at 10, 30 or 100 uM in 0.1% DMSO, final concentration. TGF-beta 1 at 5 ng/mL (Peprotech) and tritiated proline (Perkin-Elmer, (2,3,4,5-$^3$H)-proline) at 1 uCi/mL were added and the incubation continued for a further 44 hours. Treatments were performed in triplicate.

After the incubation, cells were placed on ice and washed three times with ice cold PBS. They were then incubated on ice with 10% TCA for 30 minutes, followed by a final wash in cold 10% TCA. The cells were solubilized in 0.75 mL of 1M NaOH at 37 C for 45 minutes, or overnight at 4 C. Aliquots of the solubilized cells were neutralized in an equal amount of 1M HCl and counted in scintillant in a beta counter. Aliquots of neutralized solubilized cells were assayed for protein using the BioRad Bradford Protein Assay. Proline incorporation was normalized for protein content (cpm $^3$H-proline incorporated per ug protein).

In order to compare the results of experiments performed on different days, the percentage inhibition of proline incorporation was calculated for each treatment by setting the TGF treatment at 0% inhibition and the control (incubation with media alone) at 100% inhibition.

Mesangial Cells
Percentage Reduction of TGF-Beta 1 Stimulated Proli Incorporation:

| FT | 10 μM | 30 μM | 100 μM | Tox. Rank (4 = non-toxic) |
|---|---|---|---|---|
| 98 | 30% | 70% | 70% | 4 |
| 102 | 0 | 0 | 10%, ppt | 4 |
| 106 | 0 | 0, sick | dead | 1@100 uM 2@30 uM |
| 107 | 0 | 0 | 0, ppt | 4 (yellow floating patches @ 30 & 100 uM) |
| 108 | 75% | 95% | 100+% | 4 (yellow jellylike patches @ 30 & 100 uM) |
| 109 | 3% | 16% | 75%, ppt | 4 |
| 110 | 0 | 0 | 0, ppt | 3@100 uM (cells elongated) |
| 113 | 20% | 67% | 44% | 4 |

-continued

| FT | 10 μM | 30 μM | 100 μM | Tox. Rank (4 = non-toxic) |
|---|---|---|---|---|
| 121 | ~60% | 100+% | dead | 1@100 uM 3@30 uM |
| 122 | ~25% | ~80% | dead | 1@100 uM 4@30 uM |
| 123 | 0 | 0, ppt, sick | 0, ppt, dead | 1 to 2 |
| 124 | 0, ppt | 0, ppt, sick | 0, ppt, sick | 2 |
| 125 | 0 | 0, sick | 0, sick | 2 |
| 126 | ~55% | ~75% | ~100% | 4 |
| 127 | 0 | 0 | ~50% | 4 |
| 128 | ~20% | ~20% | ~40% | 3@100 uM (some death) |
| 129 | ~10% | ~75% | dead | 1@100 uM 2@30 uM |
| 130 | ~10% | ~30% | ~50% | 2@100 uM |
| 131 | ~20% | ~10% | ~10% | 4 |
| 132 | ~2% | ~75%, ppt | ~75%, ppt | 3@100 uM (some death) | ppt indicates compound precipitated during assay.

The details of specific embodiments described in this invention are not to be construed as limitations. Various equivalents and modifications may be made without departing from the essence and scope of this invention, and it is understood that such equivalent embodiments are part of this invention.

What is claimed is:

1. A compound of Formula (IV)

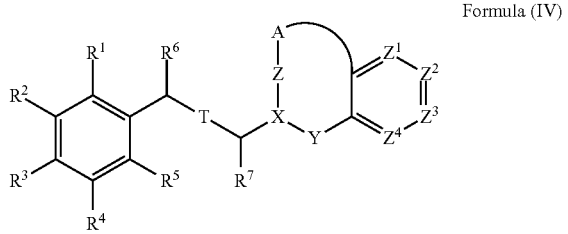

Formula (IV)

or a pharmaceutically acceptable salt thereof, wherein:
Z—X—Y is selected from the group consisting of: O—C=N, S—C=N, N=C—O, N=C—S, C=C—NH, C=C—O, C=C—S, and C(O)—C=N;
A is selected from the group consisting of: a bond, $SO_2$, C, C=S, C=O, C=$NR^9$, and $NR^9$;
T is selected from the group consisting of: a double bond and

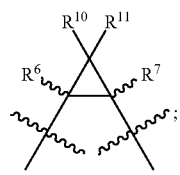

;

$Z^1, Z^2, Z^3$, and $Z^4$ are each independently selected from the group consisting of: $CR^8$ and N;
$R^1$ is selected from the group consisting of: H and $C_1$-$C_6$ alkoxy;
$R^2$ is selected from the group consisting of: $C_1$-$C_{12}$ alkyloxy optionally substituted with one or more non-hydrogen substituent groups; $C_2$-$C_{12}$ alkynyloxy;
$R^3$ is selected from the group consisting of: $F_2HCF_2CO$, $F_2HCO$, $F_3CO$, and $CHCCH_2O$;
$R^4$ is selected from the group consisting of: H and $C_1$-$C_6$ alkoxy;
$R^5$ is H;
$R^6$ is selected from the group consisting of: H and $C_1$-$C_6$ alkyl;
$R^7$ is selected from the group consisting of: H, CN, $NO_2$, and $C_1$-$C_6$alkyl;
$R^8$ is selected from the group consisting of: H, halogen, COOH, $CONH_2$, CONHOH, $CONHCH_3$, $NH_2$, $SO_2CH_3$, $SO_2NH_2$, $SONHCH_3$, and $SON(CH_3)_2$;
$R^{10}$ and $R^{11}$ are each independently selected from the group consisting of: H, halogen, OH, $NO_2$, CN, $NH_2$, $C_1$-$C_{12}$ alkyl, $C_2$-$C_{12}$ alkenyl, $C_2$-$C_{12}$ alkynyl, $C_1$-$C_{10}$ heteroalkyl, $C_3$-$C_{12}$ cycloalkyl, $C_3$-$C_{12}$ cycloalkenyl, $C_2$-$C_{12}$ heterocycloalkyl, $C_2$-$C_{12}$ heterocycloalkenyl, $C_6$-$C_{18}$ aryl, $C_1$-$C_{18}$ heteroaryl, $C_1$-$C_{12}$ alkyloxy, $C_2$-$C_{12}$ alkenyloxy, $C_2$-$C_{12}$ alkynyloxy, $C_1$-$C_{10}$ heteroalkyloxy, $C_3$-$C_{12}$ cycloalkyloxy, $C_3$-$C_{12}$ cycloalkenyloxy, $C_1$-$C_{12}$ heterocycloalkyloxy, $C_1$-$C_{12}$ heterocycloalkenyloxy, $C_6$-$C_{18}$ aryloxy, $C_1$-$C_{18}$ heteroaryloxy, $C_1$-$C_{12}$ alkylamino, $SR^{12}$, $SO_3H$, $SO_2NR^{13}R^{14}$, $SO_2R^{12}$, $SONR^{13}R^{14}$, $SOR^{12}$, $COR^{12}$, COOH, $COOR^{12}$, $CONR^{13}R^{14}$, $NR^{13}COR^{12}$, $NR^{13}COOR^{12}$, $NR^{13}SO_2R^{12}$, $NR^{13}CONR^{14}R^{15}$, $NR^{14}R^{15}$, and acyl;
$R^9, R^{13}, R^{14}$, and $R^{15}$ are each independently selected from the group consisting of: H, an N-protecting group, $C_1$-$C_{12}$ alkyl, $C_2$-$C_{12}$ alkenyl, $C_2$-$C_{12}$ alkynyl, $C_1$-$C_{10}$ heteroalkyl, $C_3$-$C_{12}$ cycloalkyl, $C_3$-$C_{12}$ cycloalkenyl, $C_1$-$C_{12}$ heterocycloalkyl, $C_1$-$C_{12}$ heterocycloalkenyl, $C_6$-$C_{18}$ aryl, and $C_1$-$C_{18}$ heteroaryl; and
$R^{12}$ is selected from the group consisting of H, $C_1$-$C_{12}$ alkyl, $C_2$-$C_{12}$ alkenyl, $C_2$-$C_{12}$ alkynyl, $C_1$-$C_{10}$ heteroalkyl, $C_3$-$C_{12}$ cycloalkyl, $C_3$-$C_{12}$cycloalkenyl, $C_1$-$C_{12}$ heterocycloalkyl, $C_1$-$C_{12}$ heterocycloalkenyl, $C_6$-$C_{18}$ aryl, and $C_1$-$C_{18}$ heteroaryl.

2. A compound as claimed in claim 1 selected from the group consisting of:

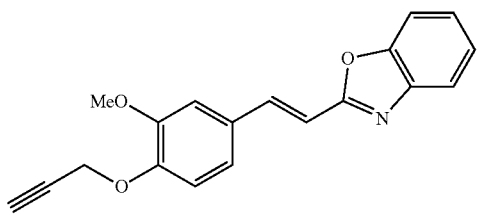

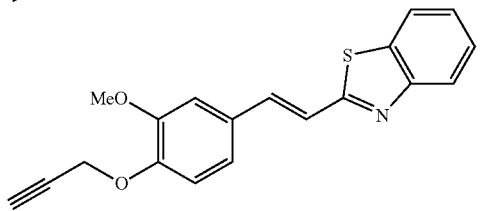

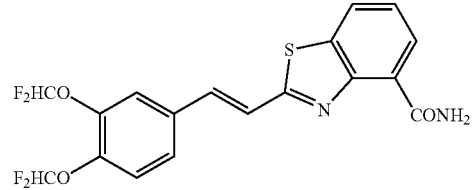

-continued

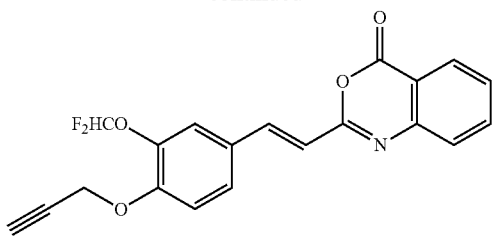

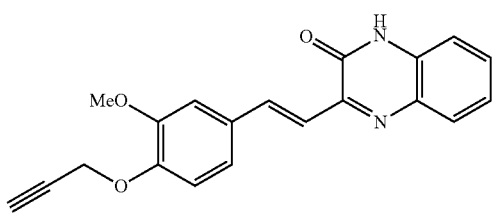

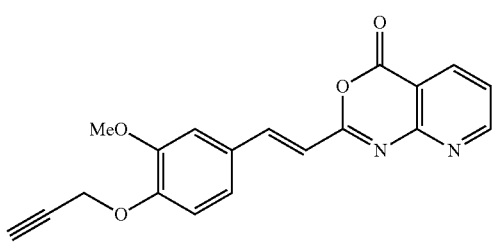

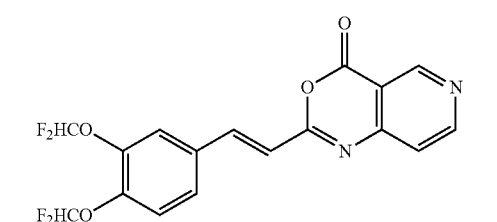

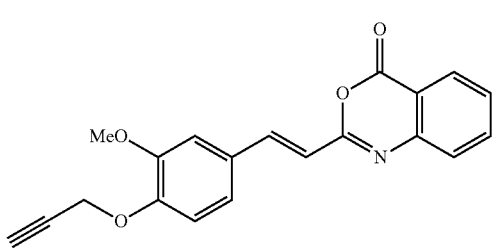 [SMILES: C#CCOc1ccc(/C=C/c2nc3ccccc3c(=O)o2)cc1OC]

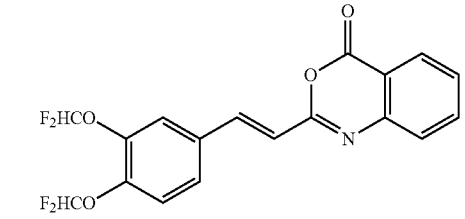 [SMILES: O=c1oc(/C=C/c2ccc(OC(F)F)c(OC(F)F)c2)nc2ccccc12]

or a pharmaceutically acceptable salt thereof.

3. A pharmaceutical composition including a compound as claimed in claim 1, and a pharmaceutically acceptable diluent, excipient or carrier.

4. A method of inhibiting fibrosis in a subject, the method including administering to the subject a therapeutically effective amount of a compound as claimed in claim 1.

5. A compound selected from the group consisting of:

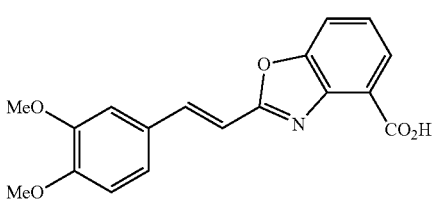

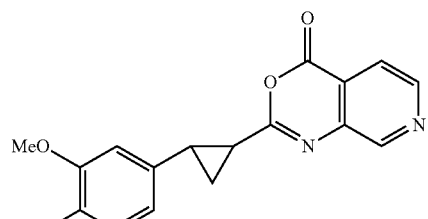

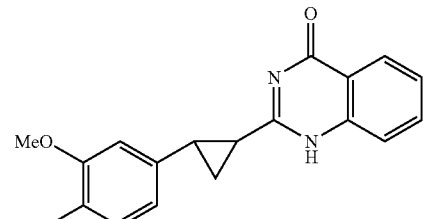

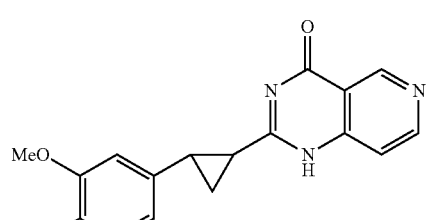

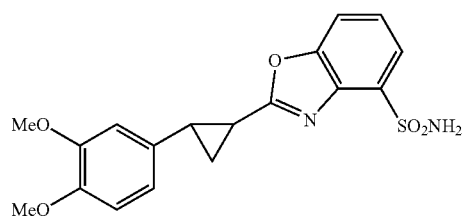

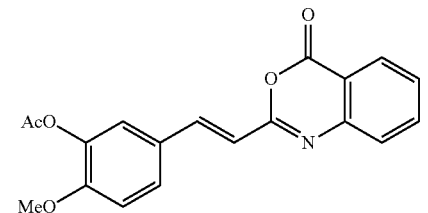

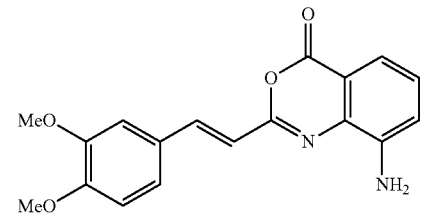

-continued
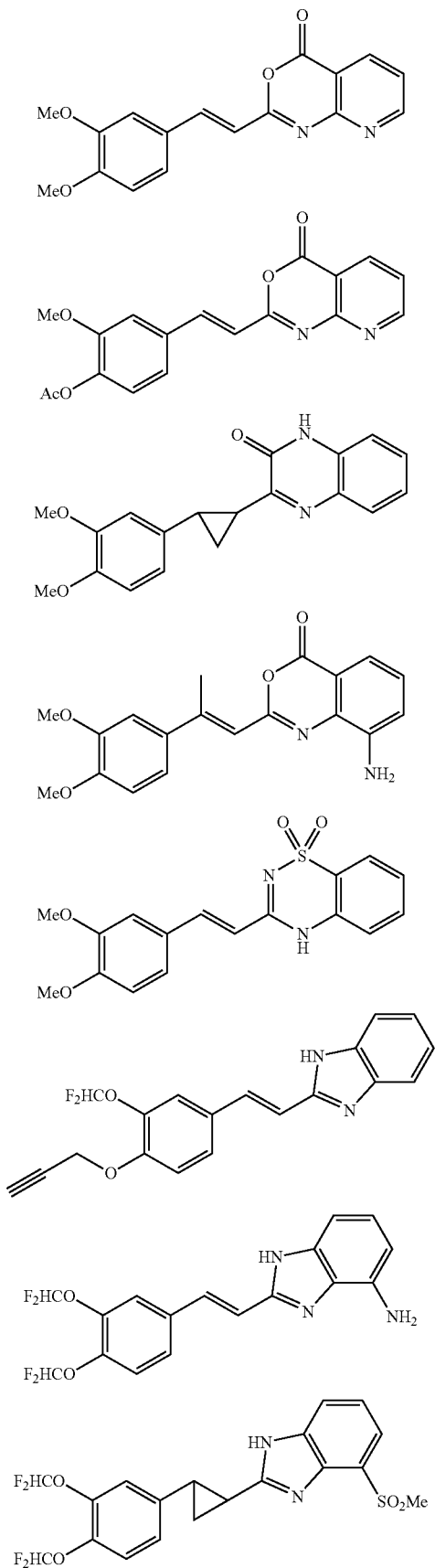
-continued
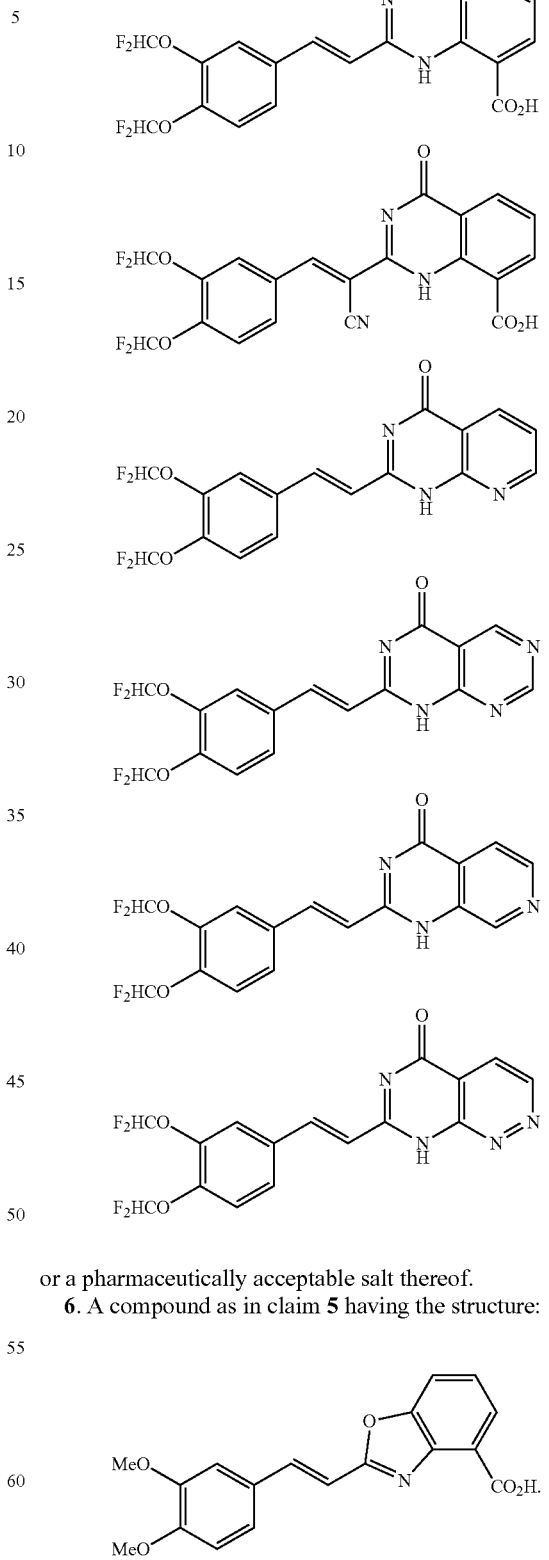
or a pharmaceutically acceptable salt thereof.
6. A compound as in claim 5 having the structure:
7. A method of inhibiting fibrosis in a subject, the method including administering to the subject a therapeutically effective amount of a compound as claimed in claim 5.

8. A method of inhibiting fibrosis in a subject, the method including administering to the subject a therapeutically effective amount of a compound as claimed in claim 6.

* * * * *

UNITED STATES PATENT AND TRADEMARK OFFICE
CERTIFICATE OF CORRECTION

PATENT NO. : 9,062,076 B2
APPLICATION NO. : 13/503160
DATED : June 23, 2015
INVENTOR(S) : Spencer John Williams et al.

Page 1 of 1

It is certified that error appears in the above-identified patent and that said Letters Patent is hereby corrected as shown below:

*In the Claims*

In claim 5, at column 117, lines 10-17, the formula:

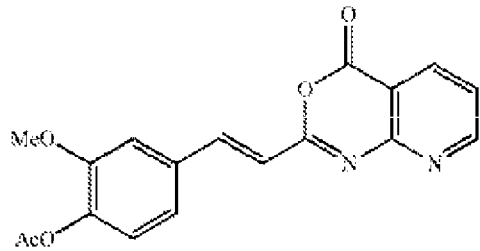

should be changed to the formula:

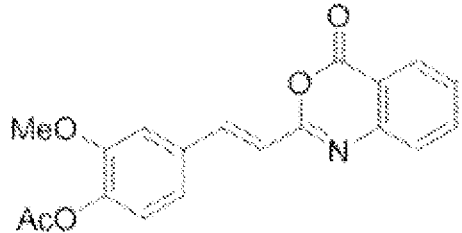

Signed and Sealed this
Twenty-eighth Day of June, 2016

Michelle K. Lee
*Director of the United States Patent and Trademark Office*